United States Patent
Cowen

(10) Patent No.: US 9,782,416 B2
(45) Date of Patent: Oct. 10, 2017

(54) PHARMACEUTICAL FORMULATIONS OF POTASSIUM ATP CHANNEL OPENERS AND USES THEREOF

(71) Applicant: Essentialis, Inc., Carlsbad, CA (US)

(72) Inventor: Neil Madison Cowen, Carlsbad, CA (US)

(73) Assignee: Essentialis, Inc., Redwood City, CA (US)

( * ) Notice: Subject to any disclaimer, the term of this patent is extended or adjusted under 35 U.S.C. 154(b) by 0 days.

(21) Appl. No.: 14/458,032

(22) Filed: Aug. 12, 2014

(65) Prior Publication Data
US 2014/0350001 A1   Nov. 27, 2014

Related U.S. Application Data

(62) Division of application No. 12/370,456, filed on Feb. 12, 2009, now abandoned, which is a division of application No. 11/212,130, filed on Aug. 25, 2005, now abandoned.

(60) Provisional application No. 60/668,912, filed on Apr. 6, 2005, provisional application No. 60/654,571, filed on Feb. 22, 2005, provisional application No. 60/624,219, filed on Nov. 3, 2004, provisional application No. 60/604,085, filed on Aug. 25, 2004.

(51) Int. Cl.
| | | |
|---|---|---|
| A61K 31/549 | (2006.01) | |
| A61K 31/655 | (2006.01) | |
| A61K 9/50 | (2006.01) | |
| A61K 9/00 | (2006.01) | |
| A61K 9/20 | (2006.01) | |
| A61K 9/28 | (2006.01) | |

(52) U.S. Cl.
CPC .......... *A61K 31/549* (2013.01); *A61K 9/0004* (2013.01); *A61K 9/2054* (2013.01); *A61K 9/5026* (2013.01); *A61K 9/5047* (2013.01); *A61K 31/655* (2013.01); *A61K 9/2853* (2013.01)

(58) Field of Classification Search
None
See application file for complete search history.

(56) References Cited

U.S. PATENT DOCUMENTS

| | | | |
|---|---|---|---|
| 2,678,311 | A | 5/1954 | Delmar et al. |
| 2,986,573 | A | 5/1961 | Topliss et al. |
| 3,265,573 | A | 8/1966 | Goldberg |
| 3,269,906 | A | 8/1966 | Topliss et al. |
| 3,304,228 | A | 2/1967 | Topliss |
| 3,345,365 | A | 10/1967 | Topliss et al. |
| 3,431,138 | A | 3/1969 | Zingerman et al. |
| 4,029,780 | A | 6/1977 | Nishimura et al. |
| 4,184,039 | A | 1/1980 | Soldati et al. |
| 4,880,830 | A | 11/1989 | Rhodes |
| 4,894,448 | A | 1/1990 | Pelzer |
| 5,063,208 | A | 11/1991 | Rosenberg et al. |
| 5,284,845 | A | 2/1994 | Paulsen |
| 5,356,775 | A | 10/1994 | Hebert et al. |
| 5,376,384 | A | 12/1994 | Eichel et al. |
| 5,378,704 | A | 1/1995 | Weller, III |
| 5,399,359 | A | 3/1995 | Baichwal |
| 5,415,871 | A | 5/1995 | Pankhania et al. |
| 5,629,045 | A | 5/1997 | Veech |
| 5,733,563 | A | 3/1998 | Fortier |
| 5,744,594 | A | 4/1998 | Adelman et al. |
| 5,965,620 | A | 10/1999 | Sorgente et al. |
| 6,022,562 | A | 2/2000 | Autant et al. |
| 6,140,343 | A | 10/2000 | Deninno et al. |
| 6,146,662 | A | 11/2000 | Jao et al. |
| 6,197,765 | B1 | 3/2001 | Vardi et al. |
| 6,197,976 | B1 | 3/2001 | Harrington et al. |
| 6,225,310 | B1 | 5/2001 | Nielsen et al. |
| 6,255,459 | B1 | 7/2001 | Lester et al. |
| 6,277,366 | B1 | 8/2001 | Goto et al. |
| 6,309,855 | B1 | 10/2001 | Duprat et al. |
| 6,313,112 | B1 | 11/2001 | Busija |
| 6,329,367 | B1 | 12/2001 | Hansen et al. |

(Continued)

FOREIGN PATENT DOCUMENTS

| | | |
|---|---|---|
| CN | 1294519 A | 5/2001 |
| DE | 2757925 | 6/1979 |

(Continued)

OTHER PUBLICATIONS

Lee Expert Opinion in Pharmacotherapy 2002 3(10):1451-1459.*
Ashcroft et al. Diabetologia 1999 42:903-919.*
Ashcroft et al. Trends in Pharmacological Sciences 2000 21:439-445.*
Alemzadeh et al. (Journal of Clinical Endocrinology and Metabolism 1998 83(6):1911-1915.*
Proglycem® reference (Mar. 2003).*
Reddy et al. (AAPS PharmSciTech 2003 4(4):1-9.*
Burman et al. Endocrine Reviews 2001 22(6):787-799.*
Pietrobelli et al. Obesity Research 1998 6(3):196-201.*
Aguilar-Bryan et al., toward Understanding the Assembly and Structure of $K_{ATP}$ Channels, *Physiological Review*, 78(1):227-245 (1998).
Aishima et al., "Actions of ZD0947, a Novel ATP-sensitive K+ Channel Opener, on Membrane Currents in Human Detrusor Myocytes", *British Journal of Pharmacology*, Nov. 2006, vol. 149, No. 5, pp. 542-550.

(Continued)

*Primary Examiner* — Robert A Wax
*Assistant Examiner* — Caralynne Helm

(57) ABSTRACT

Provided are immediate or prolonged administration of certain potassium ATP ($K_{ATP}$) channel openers to a subject to achieve novel pharmacodynamic, pharmacokinetic, therapeutic, physiological, metabolic and compositional outcomes in the treatment of diseases or conditions involving $K_{ATP}$ channels. Also provided are pharmaceutical formulations, methods of administration and dosing of $K_{ATP}$ channel openers that achieve these outcomes and reduce the incidence of adverse effects in treated individuals. Further provided are method of co-administering $K_{ATP}$ channel openers with other drugs to treat diseases of humans and animals.

10 Claims, No Drawings

(56) References Cited

U.S. PATENT DOCUMENTS

| | | |
|---|---|---|
| 6,361,795 B1 | 3/2002 | Kuczynski et al. |
| 6,436,944 B1 | 8/2002 | Maytom |
| 6,635,277 B2 | 10/2003 | Sharma et al. |
| 6,894,043 B1 | 5/2005 | Pirotte et al. |
| 6,939,576 B2 | 9/2005 | Deshpande et al. |
| 7,053,180 B2 | 5/2006 | Johnson et al. |
| 7,091,225 B2 | 8/2006 | Sierra |
| 7,268,130 B2 | 9/2007 | Desos et al. |
| 7,378,414 B2 | 5/2008 | Hutchinson et al. |
| 7,572,789 B2 | 8/2009 | Cowen et al. |
| 7,799,777 B2 | 9/2010 | Cowen et al. |
| 9,381,202 B2 | 7/2016 | Cowen et al. |
| 2001/0001658 A1 | 5/2001 | Chen et al. |
| 2001/0021404 A1 | 9/2001 | Uhlemann et al. |
| 2002/0035106 A1 | 3/2002 | Hansen et al. |
| 2002/0098179 A1 | 7/2002 | Brearley et al. |
| 2002/0173636 A1 | 11/2002 | Chen |
| 2003/0035106 A1 | 2/2003 | Yeh et al. |
| 2003/0068366 A1* | 4/2003 | Chungi et al. ............. 424/452 |
| 2003/0083308 A1 | 5/2003 | Bernstein |
| 2003/0161842 A1 | 8/2003 | Wang et al. |
| 2003/0180352 A1 | 9/2003 | Patel et al. |
| 2003/0185873 A1 | 10/2003 | Chasin |
| 2003/0199492 A1 | 10/2003 | Scott |
| 2003/0211123 A1* | 11/2003 | Shukla et al. ............. 424/400 |
| 2004/0058908 A1 | 3/2004 | Keller et al. |
| 2004/0087515 A1 | 5/2004 | Butler et al. |
| 2004/0097492 A1 | 5/2004 | Pratt et al. |
| 2004/0122104 A1 | 6/2004 | Hirsch et al. |
| 2004/0143213 A1* | 7/2004 | Hunter et al. ............ 604/93.01 |
| 2004/0167123 A1 | 8/2004 | Pratt et al. |
| 2004/0204472 A1 | 10/2004 | Briggs et al. |
| 2004/0225346 A1 | 11/2004 | Mazumder et al. |
| 2004/0229803 A1 | 11/2004 | Stephenson et al. |
| 2004/0266822 A1 | 12/2004 | Wang et al. |
| 2005/0075331 A1 | 4/2005 | Pratt et al. |
| 2005/0089473 A1 | 4/2005 | Black et al. |
| 2005/0203072 A1 | 9/2005 | Rudolph et al. |
| 2005/0203186 A1 | 9/2005 | Kraass |
| 2006/0051418 A1 | 3/2006 | Cowen et al. |
| 2006/0128673 A1* | 6/2006 | Firnges et al. ............. 514/149 |
| 2006/0148037 A1 | 7/2006 | Johnson et al. |
| 2006/0263805 A1 | 11/2006 | Terzic et al. |
| 2007/0191351 A1 | 8/2007 | Cowen et al. |
| 2007/0254863 A1 | 11/2007 | Antel et al. |
| 2007/0254871 A1 | 11/2007 | Gehenne et al. |
| 2009/0062264 A1 | 3/2009 | Cowen et al. |
| 2009/0148525 A1 | 6/2009 | Cowen |
| 2009/0149451 A1 | 6/2009 | Cowen |
| 2010/0028429 A1 | 2/2010 | Cowen et al. |
| 2010/0256360 A1 | 10/2010 | Cowen et al. |
| 2012/0238554 A1 | 9/2012 | Cowen |
| 2013/0040942 A1 | 2/2013 | Cowen et al. |
| 2013/0309301 A1 | 11/2013 | Cowen et al. |
| 2014/0364425 A1 | 12/2014 | Cowen et al. |
| 2016/0136178 A1 | 5/2016 | Cowen |

FOREIGN PATENT DOCUMENTS

| | | |
|---|---|---|
| EP | 327263 | 7/1994 |
| EP | 618209 | 12/1998 |
| GB | 982072 | 2/1965 |
| JP | 52-48889 B2 | 7/1977 |
| JP | 59-95212 | 6/1984 |
| JP | 2002-114779 A | 4/2002 |
| JP | 4220314 B2 | 2/2009 |
| WO | 93/21171 | 10/1993 |
| WO | 94/25033 A1 | 11/1994 |
| WO | 98/10786 | 3/1998 |
| WO | WO-00/48636 A1 | 8/2000 |
| WO | 02/30411 | 4/2002 |
| WO | 02/50085 | 6/2002 |
| WO | 03/074034 | 9/2003 |
| WO | 03/099801 | 12/2003 |
| WO | 03/103606 A2 | 12/2003 |
| WO | 03/105896 | 12/2003 |
| WO | 2004/099217 | 11/2004 |
| WO | 2006/000607 A1 | 1/2006 |
| WO | 2006/026469 | 3/2006 |
| WO | 2006/045799 A2 | 5/2006 |
| WO | 2007/081521 A2 | 7/2007 |
| WO | WO-2009/006483 A1 | 1/2009 |
| WO | WO-2013/130411 A1 | 9/2013 |
| WO | WO-2016/077629 A1 | 5/2016 |

OTHER PUBLICATIONS

Aizawa et al., Proplylaxis of Genetically Determined Diabetes by Diazoxide: A Study in a Rat Model of Naturally Occurring Obese Diabetes, *J of Pharma Exp Ther* 275(1): 194-199 (1995).

Alemzadeh and Tushaus, Diazoxide attenuates insulin secretion and hepatic lipogenesis in zucker diabetic fatty rats, *Med Sci Monit*, 11(12): BR439-448 (2005).

Alemzadeh et al., Antiobesity Effect of Diazoxide in Obese Zucker Rats, *Metabolism* 45:334-341 (1996).

Alemzadeh et al., Beneficial Effect of Diazoxide in Obese Hyperinsulinemic Adults, *J Clin Endocr Metab* 83:1911-1915 (1998).

Alemzadeh et al., Chronic suppression of insulin by diazoxide alters the activities of key enzymes regulating hepatic gluconeogenisis in Zucker rats, *European Journal of Endocrinology* 146:871-879 (2002).

Alemzadeh et al., Diazoxide enhances adipose tissue protein kinase B activation and glucose transporter-4 expression in obese Zucker rats, *Med Sci Monit* 10(3): BR53-60 (2004).

Alemzadeh et al., Effect of Diazoxide on Brain Capilary Insulin Receptor Binding and food Intake in Hyperphagic Obese Zucker Rats, *Endocrinology* 140:3197-3202 (1999).

Alemzadeh et al., Modification of Insulin Resistance by Diazoxide in Obese Zucker Rats, *Endocrinology* 133:705-712 (1993).

Alemzadeh et al., Modulation of Adipoinsular Axis in Prediabetic Zucker Diabetic Fatty Rats by Diazoxide, Endrocrinology, 145(12): 5476-5484, (2004).

Babenko et al., A View of Sur/$K_{IR}$6.X, $K_{ATP}$ Channels, Annu. Rev. Physiol., pp. 667-687, vol. 60 (1998).

Babenko et al., Pharmaco-topology of Sulfonylurea Receptors, Separate Domains of the Regulatory Subunits of $K_{ATP}$ Channel Isoforms are Required for Selective Interaction with $K^+$ Channel Openers, *J Biol Chem*, 275(2), 717-720 (2000).

Ball et al., "Alterations of Insulin Secretion Following Long-Term Manipulation of ATP-sensitive Potassium Channels by Diazoxide and Nateglinide", *Biochemical Pharmacology*, Jan. 1, 2005, vol. 69, No. 1, pp. 59-63.

Barse, et al., Evidence for the Role of Insulin Secretion in the Production of Endogenous Hypertriglyceridemia, *J Clin Invest* 47(6):6a (1968).

Beaumont et al., Classification of Hyperlipidaemias and Hyperlipoproteinaemias, *Bull World Health Org.* 43(6):891-915 (1970).

Berge et al., Pharmaceutical Salts. Journal of Pharmaceutical Sciences, 66(1): 1-19, 1977.

Bertolino et al., Modulation of AMPA/Kainate receptors by Analogues of Diazoxide and Cyclothiazide in Thin Slices of Rat Hippocampus, *Receptors and Channels*, 1, 267-278 (1993).

Bjork et al, Diazoxide treatment at onset preserves residual insulin secretion in adults with autoimmune diabetes, Diabetes, American Diabetes Association, 1996, 45(10):1427-1430.

Bjork et al., Diazoxide Treatment at Onset Preserves Residual Insulin Secretion in Adults with Autoimmune Diabetes, *Diabetes Care* 21(3):427-430 (1998).

Bjork et al., Induction of β-Cell Rest in Type 1 Diabetes, Diabetes, 45:1427-1430, (1996).

Björklund et al., Glucose-Induced $[Ca^{2+}]_i$ Abnormalities in Human Pancreatic Islets, Important Role of Overstimulation, *Diabetes*, 49:1840-1848 (2000).

Bombieri et al., "Structural Studies on Benzothiadiazine Derivatives: 3-aminomethy1-1,2,4-benzothiadiazine 1,1-dioxide and 6-aminomethyl-3-methyl-1,2,4-benzothiadiazine 1,1-dioxide

(56) References Cited

OTHER PUBLICATIONS

Hydrochloride Monohydrate", *Journal of Crystallographic and Spectroscopic Research*, vol. 20, No. 5, pp. 457-463 (1990).
Bookman et al. Liver International 2006, 26, 566-571.
Braghiroli et al., "Rigid Analogs of Taurine as Potential Taurine Antagonists", *Farmaco*, vol. 45, No. 6, pp. 631-645 (1990).
Canadian Office Action dated Mar. 9, 2012 for CA Application No. 2,636,274.
Chait, et al., Lipodystrophy with Hyperlipidaemia: The Role of Insulin in Very Low Density Lipoprotein over-synthesis, Clin Endocrin, 10:173-178 (1979).
Chan et al., Reversibility of primary pulmonary hypertension during six years of treatment with oral diazoxide, Br Heart J 57(2):207-209 (1987).
Chinese Office Action dated Jun. 26, 2012 for CN Application No. 200580035520.5 (169560-CN-1).
Cosgrove et al., BPDZ 154 Activates Adenosine 5'-Triphosphate-Sensitive Potassium Channels: In Vitro Studies Using Rodent Insulin-Secreting Cells and Islets Isolated from Patients with Hyperinsulinism, *J. Clin. Endocrinol. Metab.*, 87, 4860-4868 (2002).
Cowen et al., Salts of Potassium ATP (KATO) channel openers and uses thereof, CA 150:114355 (2009).
Cryer, P.E., Mechanisms of hypoglycemia-associated autonomic failure and its component syndromes in diabetes, Diabetes, 2005, 54(12):3592-3601.
D'Hahan et al., *Pharmacological plasticity of cardiac ATP-sensitive potassium channels toward diazoxide revealed by ADP*, PNAS, Oct. 12, 1999, pp. 12162-12167, vol. 96, No. 21 (1999).
Dabrowski et al., "A Novel SUR1/Kir6.2 Specific KATP Channel Opener", Proceedings of the Scientific Meeting of the Physiological Society Mar. 19-21, 2001, *Journal of Physiology (Cambridge)*, Reprint May 2001, No. 533P., p. 115P (2001).
Dabrowski et al., The Novel Diazoxide Analog 3-Isopropylamino-7-Methoxy-4H-1,2,4-Benzothiadiazine 1,1-Dioxide Is a Selective Kir6.2/SUR1 Channel Opener, *Diabetes*, 51, 1896-1906 (2002).
De Tullio et al., Toward Tissue-Selective Pancreatic B-Cells $K_{ATP}$ Channel Openers Belonging to 3-Alkylamino-7-halo-4H-1,2,4-benzothiadiazine 1,1-Dioxides, *J. Med. Chem.*, 46:3342-3353 (2003).
Delmar et al., Theophylline Salts, CAPLUS 49: 32579, 1955.
Dong et al., "L-OROS® SOFTCAP™ for Controlled Release of Non-Aqueous Liquid Formulations", Drug Delivery Technologies online article.
Drogovoz et al., "Relation Between the Structure and Diuretic Activity of 2H-1,2,4-benzothiadiazine-1,1-dioxide-3-carboxylic Acid Derivatives", *Farmzkologiya I Toksikologiya (Pharmacology & Toxicology)*, vol. 40, No. 1, pp. 73-76 (1977). (English Translation provided).
Eaton, RP and Schade, DS, The Effect of Diazoxide-induced Hormonal Secretion on Plasma Triglyceride Concentration in the Rat, *Diabetologia* 18:301-306 (1980).
Eaton, RP, and Nye, WH., The relationship between insulin secretion and triglyceride concentration in endogenous lipemia, *J Lab Clin Med* 81(5):682-695 (1973).
Escande et al., The Potassium Channel Opener Cromakalim (BRL 34915) Activates ATP-Dependent $K^+$ Channels in Isolated Cardiac Myocytes, *Biochem Biophys Res Commun*, 154, 620-625 (1988).
European Office Action dated Aug. 9, 2012 for EP Application No. 11184345.4-2123 (169259-EP-2).
European Office Action dated Dec. 10, 2009 for EP Application No. 06847875.9.
European Search Report dated Jun. 14, 2010 for EP Application No. 10159141.0 (059599-0213).
European Search Report dated Oct. 28, 2010 for EP Application No. 08772317.7 (059599-0407).
European Supplementary Partial Search Report dated Jun. 15, 2009 for EP Application No. 05791600.9.
Examination Report dated Nov. 24, 2011 for EP Application No. 10159141.0 (059599-0213).
Extended European Search Report dated Dec. 9, 2011 for EP Application No. 11184345.4.
Foreign Search Report dated Nov. 24, 2011 for EP Application No. 11184285.2 (059599-0228).
Fozard et al., *Potassium Channel Openers*, New Drugs for Asthma, Allergy and COPD, Progress in Respiratory Research, pp. 77-80, vol. 31 (2001).
Fredrickson, D.S. and Lees, R.S., Editorial: A System for Phenotyping Hyperlipoproteinemia, *Circulation* 31:321-327 (1965).
Gennaro ed, Remington's Pharmaceutical Sciences, Easton:Mack Publishing Company, 1985 p. 1604.
Girard et al., "Aminomethyl-1,2,4-benzothiadiazines as Potential Analogs of γ-aminobutyric Acid. Unexpected discovery of a Taurine Antagonist", *Journal of Medicinal Chemistry*, vol. 25, No. 2, pp. 113-116 (1982).
Guldstrand et al., Improved Beta Cell Function After Short-Term Treatment with Diazoxide in Obese Subjects with Type 2 Diabetes, *Diabetes and Metabolism* 28:448-456 (2002).
Hanley et al., "KATP Channel Opener Diazoxide Inhibits Succinate Dehydrogenase in the Mammalian Heart", Proceedings of the Scientific Meeting of the Physiological Society Mar. 19-21, 2001, *Journal of Physiology*, Reprint May 2001, No. 533P, pp. 33P-34P (2001).
Hanley et al., "KATP Channel-independent Targets of Diazoxide and 5-Hydroxydecanoate in the Heart," *Journal of Physiology*, August, vol. 542, No. 3, pp. 735-741 (2002).
Harvard Health Publications, "Should you worry about high triglycerides?" Apr. 2006, obtained from http://health.harvard.edu/fhg/updates/update0406b.shtml.
International Search report for PCT Application PCT/US2006/048711.
International Search Report for PCT Patent Application No. PCT/US2008/068936.
Isomoto et al., A Novel Sulfonylurea Receptor Forms with BIR (Kir6.2) a Smooth Muscle Type ATP-sensitive $K^+$ Channel, *J. Biol. Chem.*, 271 (40)24321-24324 (1996).
Japanese Office Action dated May 15, 2012 for JP Application No. 2007-530177 (169560-JP-1).
Johnson et al., The effect of Once-Daily Minoxidil on Blood Pressure and Plasma Lipids, J. Clin Pharmacol, 1986; 26, pp. 534-538.
Kratzl et al., "Tetracyclic 1,2,4-benzothiadiazines. II. Nitro and chloro Derivatives", *Monatshefte fuer Chemie*, vol. 96, No. 5, pp. 1592-1595 (1965). (German only—no English translation provided).
Lawrence et al., "The KATP Channel Opener Diazoxide Protects Cardiac Myocytes During Metabolic Inhibition Without Causing Mitochondrial Depolarization or Flavoprotein Oxidation", *British Journal of Pharmacology*, October, vol. 34, No. 3, pp. 535-542 (2001).
Lebrun et al., "A Potent Diazoxide Analogue Activating ATP-Sensitive K+ Channels and Inhibiting Insulin Release", *Diabetologia*, June, vol. 43, No. 6, pp. 723-732 (2000).
Leonard, "Effects of Digitalis on Intracellular Potassium", *Cardiovascular Drug Therapy*, pp. 419-423 (1965).
Loubatiérés et al., "Etude Experimentale d'un Sulfamide Hyperglycéemiant, le Diazoxide (Experimental Study of Diazoxide, a Hyperglycemic Sulfonamide" *Societe de Biologie*, Jan. 17, 1996, vol. 160, pp. 165-168 (1996). (English Translation provided).
Marchesini et al. Hepatology 2003, 37, 917-923.
Matzno et al., A Possible Mechanism of Action of a New Potassium Channel Opener, AL0671, on Lipid Metabolism in Obese Zucker Rats, *J Pharmacol Exp Ther* 271(3):1666-71 (1994).
Notice of Allowance dated May 24, 2010 for U.S. Appl. No. 11/614,044 (059599-0303).
Office Action dated Mar. 24, 2010 for U.S. Appl. No. 11/212,130 (059599-0202).
Office Action dated Apr. 17, 2009 for U.S. Appl. No. 12/391,990 (059599-0601).
Office Action dated Apr. 24, 2009 for Chinese Application No. 200580035520.5 (with English Translation) (059599-0209).
Office Action dated Jun. 9, 2010 for U.S. Appl. No. 12/368,215 (059599-0212).

(56) References Cited

OTHER PUBLICATIONS

Office Action dated Sep. 17, 2009 for U.S. Appl. No. 11/212,130 (059599-0202).
Office Action dated Dec. 8, 2009 for U.S. Appl. No. 12/368,215 (059599-0212).
Office Action dated Feb. 28, 2012 for CN Application No. 200680050425.7 (059599-0306).
Office Action dated Feb. 11, 2013 for AU Application 2012203517.
Office Action dated Dec. 7, 2012 for CA Application No. 2,636,274.
Office Action dated Jan. 18, 2013 for EP Application 08 772 317.7-2123.
Office Action dated Sep. 13, 2011 for JP Application No. 2007-530177 (059599-0207) (Japanese language with English translation).
Okada et al., Effects of the $K^+$ Channel Opener KRN4884 on the Cardiovascular Metabolic Syndrome Model in Rats, *Cardiovasc Pharmacol* 35(2):287-293 (2000).
Ortqvist et al., Temporary Preservation of β-Cell Function by Diazoxide Treatment in Childhood Type 1 Diabetes, *Diabetes Care* 27(9):2191-2197 (2004).
Ouedraogo et al., 2-Alkyl-3-Alkylamino-2H-Benzo- and Pyridothiadiazine 1,1-Dioxides: From $K+_{ATP}$ Channel Openers to Ca++ Channel Blockers?, *Bol. Chem.*, 383, 1759-1768 (2002).
Patent Examination Report dated Nov. 28, 2012 for AU Application No. 2008272923.
Petegnief et al., "Taurine Analog Modulation of Taurine Uptake by Two Different Mechanisms in Cultured Glial Cells", *Biochemical Pharmacology*, vol. 49, No. 3, pp. 399-410 (1995).
Petyunin et al., "Use of 2-Sulphamoyl Oxanilic Acid Esters as a Basis for the Synthesis of Derivatives of 2-H-1,2,3-Benzothiadiazine-1,1-dioxo-3-carboxylic acid Derivatives", *Khimiya Geterotsiklicheskikh Soedineii (Chemistry of Heterocyclic Compounds), Report LVII from Heterocyclic Chemistry Research series*, vol. 8, pp. 1056-0159 (1976). (English Translation provided).
Pruitt et al., "Metabolism of Diazoxide in Man and Experimental Analysis", *Journal of Pharmacology and Experimental Therapeutics*, vol. 188, No. 1, pp. 248-256 (1974).
Qvigstad et al., Nine weeks of bedtime diazoxide is well tolerated and improves β-cell function in subjects with Type 2 diabetes, *Diabetic Medicine* 21:73-76 (2004).
Raffa et al., "1,2,4-Benzothiadiazine Derivatives Research. Note XIII. Reaction Between 3-chloroalkyl-1,2,4-benzothiadiazine ,1-dioxide and Amines," *Farmaco Edizione Scientifica*, vol. 15, pp. 700-715 (1960). (English Translation provided).
Raffa et al., "1,2,4-Benzothiadiazine Derivatives Research. Note XIV. Relation Between Chemistry and Flavor", *Farmaco Edizione Scientifica*, vol. 15, pp. 716-725 (1960). (English Translation provided).
Raffa et al., "1,2,4-Benzothiadiazine Derivatives Research: Note XV. Relation Between 3-chloroalkyl-1,2,4-benzothiadiazine 1,1-dioxide and Tertiary Amines", *Farmaco Edizione Scientifica*, vol. 15, pp. 842-855 (1960). (English Translation provided).
Raju et al, Loss of the decrement in intraislet insulin plausibly explains loss of the glucagon response to hypoglycemia in insulin-deficient diabetes: Documentation of the intraislet insulin hypothesis in humans, Diabetes, 2005, 54(3):757-764.
Ratzmann et al., Effect of Pharmacological Suppression of Insulin Secretion on Tissue Sensitivity to Insulin in Subjects with Moderate Obesity, *Int J Obesity* 7(5):453-458 (1983).
Reddy et al., Once-Daily Sustained-Released Matrix Tablets of Nicorandil: Foundation and In Vitro Evaluation, *AAPS Pharm Sci Tech* 4(4):1-98, 9 (2003).
*Remington's Pharmaceutical Sciences*, 19th ed., Preformation, Mack Publishing Co., Easton, PA, vol. 2, p. 1457, (1995).
Saku, et al., Effects of Pinacidil on Serum Lipid, Lipoprotein, and Apolipoprotein Levels in Patients with Mild to Moderate Hypertension, Clin Ther 12(2):132-138 (1990).
Sanbar, Metabolism of Plasma Glucose and Lipids following Diazoxide Administration in Dogs, SS *Metabolism* 16(3):259-270 (1967).

Sasaki et al. Clinical Therapeutics, 2002, 24, 1614-1626.
Schou et al., Synthesis and pharmacological evaluation of 4H-1,4-benzothiazine-2-carbonitrile 1,1-dioxide and N-(2-cyanomethylsulfonylphenyl)acylamide derivatives as potential activators of ATP sensitive potassium channels, *Bioorg. Med. Chem.*, 13:141-155 (2005).
Schwanstecher et al., Potassium channel openers require ATP to bind to and act through sulfonylurea receptors, *EMBO J.*, 17:5529-5535 (1998).
Schwartz et al., Cardioprotection by multiple preconditioning cycles does not require mitochondrial KATP channels in pigs, *Am J Physiol Heart Circ Physiol* 283:H1538-H1544 (2002).
Squarcia et al., Primary pulmonary hypertension in childhood: familial aspects, *Pediatr Med Chir* 3(6):467-472 (1981), abstract only.
Stadnicka et al., "Isoflurane Sensitizes the Cloned Pancreatic KATP Channel to Diazoxide", Anesthesiology Abstracts of Scientific Papers Annual Meeting Oct. 16-18, 2000, *American Society of Anesthiologists*, Reprint 2002, Abstract No. 683.
Stanridge et al., Diazoxide down-regulates leptin and lipid metabolizing enzymes in adipose tissue of Zucker rats, *FASEB J* 14:455-460 (2000).
Supplemental Accelerated Examination Support Document filed Apr. 7, 2009 in U.S. Appl. No. 12/391,990 (059599-0601).
Supplementary European Search Report for EPO Patent Application No. 06 84 7875.
Supuran et al., "Complexes with Biologically Active Ligands. Part 1. Synthesis of Coordination Compounds of Diazoxide with Transition- and Main-group Cations", *Metal Based Drugs*, vol. 3, No. 1, pp. 25-30 (1996).
Surwit et al., Diazoxide Restores $β_3$-Adrenergic Receptor Function in Diet-Induced Obesity and Diabetes, *Endocrinology* 141:3630-3637 (2000).
Tait et al., "1,2,4-Benzothiadiazine Derivatives as $α_1$ and $5-HT_{1A}$ Receptor Ligands," *Bioorganic & Medicinal Chemistry Letters*, vol. 15, No. 4, pp. 1185-1188 (2005).
Tavares et al., Expression and function of ATP-dependent potassium channels in late post-infarction remodeling, *J Mol Cell Cardiol* 42:1016-1025 (2007).
Trube et al., Opposite effects of tolbutamide and diazoxide on the ATP-dependent $K^+$ channel in mouse pancreatic β-cells, *Pfluegers Arch Eur J Physiol*, 407, 493-99 (1986).
U.S. Pharmacopeia, Chapter 711 Dissolution/Physical Tests, p. 2412-2414 (2005).
URL http://www.dow.com/dowexcipients/products/methocel.htm (Dec. 4, 2009).
U.S. Office Action dated Jan. 9, 2012 for U.S. Appl. No. 12/166,251 (169557-US-5).
U.S. Office Action dated Sep. 19, 2012 for U.S. Appl. No. 12/819,155 (169259-US-6).
U.S. Office Action dated Dec. 8, 2009 for U.S. Appl. No. 12/368,215.
U.S. Office Action dated Sep. 17, 2009 for U.S. Appl. No. 11/212,130.
U.S. Office Action dated Sep. 8, 2011 for U.S. Appl. No. 12/370,456 (059599-0211).
Wang et al., The Anti-Inflammatory Effect of Diazoxide in Coronary Artery Bypass Grafting, *Shock*, 22:23-28 (2004).
Wessberg et al., "Effects of Taurine and a Taurine Antagonist on some Respiratory and Cardiovascular Parameters", *Life Sciences*, vol. 33, No. 17, pp. 1649-1655 (1983).
Wigand et al., Downregulation of Insulin Receptors in Obese Man, *Diabetes* 28(4):287-291 (1979).
Xu et al., Antihypertensive drugs clonidine, diazoxide, hydralazine and furosemide regulate the production of cytokines by placentas and peripheral blood mononuclear cells in normal pregnancy,*J. Hypertension*, 24: 915-922 (2006).
Yarbrough et al., Neuropharmacological Characterization of a Taurine Antagonist, *Journal of Pharmacology and Experimental Therapeutics*, vol. 219, No. 3, pp. 604-613 (1981).
Yokoyama et al., Effect of KRN4884 on Lipid Metabolism in Hyperlipidemic Rats, *British Journal of Pharmacology*, 120: 1471-1476 (1997).

(56) References Cited

OTHER PUBLICATIONS

Yokoyama et al., Effects of KRN4884 a novel pyridinecarboxamidine type $K_{ATP}$ channel opener, on serum triglyceride levels in rats, J Gen Pharmacol 30(2):233-237 (1998).

Yoshinobu Nakai et al., Nanzando Co., Ltd. 1992, pp. 257-264 (Japanese language) (169560-JP-1).

Bedogni, G, et al. 2015. Does segmental body composition differ in women with Prader-Willi syndrome compared to women with essential obesity? J Endocrinol Invest DOI 10.1007/s40618-015-0266-y.

Bittel, DC, and Butler, MG. 2005. Prader-Willi syndrome: clinical genetics, cytogenetics and molecular biology. Expert Rev Mol Med 7(14):1-20.

Brambilla, P, et al. 1997. Peculiar body composition in patients with Prader-Labhart-Willi syndrome. Am J Clin Nutr 65(5):1369-1374.

Brambilla, P, et al. 2011. Metabolic syndrome in children with Prader-Willi syndrome: the effect of obesity. Nutr Metab Cardiovasc Dis 21(4):269-276.

Butler, MG, et al. 2007. Energy expenditure and physical activity in Prader-Willi syndrome: comparison with obese subjects. Am J Med Gent A 143A(5):449-459.

Cassidy, SB, and Driscoll, DJ. 2009. Prader-Willi syndrome. Eur J Hum Genet 17(1):3-13.

Cassidy, S.B., et al. 2012. Prader-Willi syndrome. Genet Med 14(1):10-26.

Davies, W, et al. 2008. Imprinted genes and neuroendocrine function. Front Neuroendocrinol 29:413-427.

de Lind van Wijngaarden, RF, et al. 2010. Cardiovascular and metabolic risk profile and acylation-stimulating protein levels in children with Prader-Willi syndrome and effects of growth hormone treatment. J Clin Endocrinol Metab 95(4):1758-1766.

Goldstone, AP, et al. 2002. Resting metabolic rate, plasma leptin concentrations, leptin receptor expression, and adipose tissue measured by whole-body magnetic resonance imaging in women with Prader-Willi syndrome. Am J Clin Nutr 75(3):468-475.

Goldstone, AP. 2004. Prader-Willi syndrome: Advances in genetics, patho-physiology and treatment. Trends Endocrinol Metab 15:12-120.

Lloret-Linares, C, et al. 2013. Comparison of body composition, basal metabolic rate and metabolic outcomes of adults with Prader-Willi syndrome ot lesional hypothalamic disease, with primary obesity. Int J Obes 37:1198-1203.

Miller, JL. 2011. Nutritional stages in Prader-Willi syndrome. Am J Med Genet A 155A(5):1-10.

Motaghedi, R, et al. 2011. Psychiatric adverse effects of Rimonobant in adults with Prader-Willi syndrome. Eur J Med Genet 54(1):14-18.

Sode-Carlsen, R, et al. 2010. Body composition, endocrine and metabolic profiles in adults with Prader-Willi syndrome. Growth hormone and IGF research 20:179-184.

Van Mil, EG, et al. 2000. Activity related energy expenditure in children and adolescents with Prader-Willi syndrome. Int J Obes Relat Metab Disord 24(4):429-434.

Bervini, S. et al., "Mouse models of Prader-Willi Syndrome: A systematic review," Frontiers in Neuroendocrinology, 2013, pp. 1-13.

Bush, J. R. et al., "Loss of the Prader-Willi obesity syndrome protein necdin promotes adipogenesis," Gene, 2012, 497:45-51.

Butler, M.G. et al., "Effects of growth hormone treatment in adults with Prader-Willi syndrome," Growth Hormone & IGF Research, 2013, pp. 1-7.

Dombret, C. et al., "Loss of Maged1 results in obesity, deficits of social interactions, impaired sexual behavior and severe alteration of mature oxytocin production in the hypothalamus," Human Molecular Genetics, 2012, 21(21):4703-4717.

Goldstone, AP et al., "Appetite hormones and the transition to hyperphagia in children with Prader-Willi syndrome," International Journal of Obesity, 2012, 36:1564-1570.

van Nieuwpoort, I.C. et al., "The relationship between IGF-I concentration, cognitive function and quality of life in adults with Prader-Willi syndrome," Hormones and Behavior, 2011, 59:444-450.

Zhang, Q. et al., "Hypothalamic expression of snoRNA Snord116 is consistent with a link to the hyperphagia and obesity symptoms of Prader-Willi syndrome," Int. J. Neuroscience, 2012, 30:479-485.

Guo, Z. et al., "Diazoxide prevents abdominal adiposity and fatty liver in obese OLETF rats at prediabetic stage," J. Diab. Complic., 2008, 22:46-55.

Wu, Q. et al., "Diazoxide Suppresses Hepatic Ischemia/Reperfusion Injury After Mouse Liver Transplantation by a BCL-2-Dependent Mechanism," J. Surg. Res., 2011, 169(2):e155-66.

Zeng, Z. et al., "Diazoxide attenuates ischemia/reperfusion injury via upregulation of heme oxygenase-1 after liver transplantation in rats," World J. Gastroenterol, 2012, 18(15):1765-1772.

Nakagawa, Y. et al., "Enhancement of Liver Regeneration by Adenosine Triphosphate-Sensitive K+ Channel Opener (Diazoxide) After Partial Hepatectomy," Transplantation, 2012, 93(11):1094-100.

Advisory Action dated Feb. 14, 2011, for U.S. Appl. No. 11/212,130, filed Aug. 25, 2005, 3 pages.

Berntson G.G., et al. (1993). "Pancreatic polypeptide infusions reduce food intake in Prader-Willi syndrome," Peptides 14:497-503.

Bray, G.A. (1977). "The Zucker-fatty rat: a review," Fed Proc 36(2):148-153.

Buch, A. et al. (1980). "Hyperlipidemia and pancreatitis," World J. Surg. 4:307-314.

Butler, M.G. et al. (1990). "Fasting plasma lipid, glucose, and insulin levels in Prader-Willi syndrome and obese individuals," Dysmorphol Clin Genet 4(1):23-36.

Calesnick, B. et al. (1965). "Importance of Dissolution Rates in Producing Effective Diazoxide Blood Levels in Man," Journal of Pharmaceutical Sciences 54:1277-1280.

Cassidy S.B. (1984). "Prader-Willi syndrome," Curr Probl Pediatr 14(1):3-55.

Chernykh et al. (1976). "Synthesis and Properties of 3-substituted 2H-1,2,4-Benzothiadiazine 1,1 Dioxide," Khimiya Geterotsiklicheskikh Soedineii (Chemistry of Heterocyclic Compounds), vol. 4, pp. 479-483. (with English Translation).

Communication pursuant to Article 94(3) EPC dated Apr. 6, 2010 for EP Application No. 06 847 875.9, 3 pages.

Communication under Rule 71(3) EPC dated Oct. 19, 2009, for EP Application No. 05 791 600.9, 7 pages.

Crimmins, E.M., Preston, S.H., Cohen, B. (2011). "Explaining divergent levels of longevity in high-income countries," Panel on Understanding Divergent Trends in Longevity in High-Income Countries, National Research Council of the National Academies Press, 194 total pages.

Cummings, D.E. et al. (2002). "Elevated plasma ghrelin levels in Prader-Willi syndrome," Nat. Med. 8:643-644.

Delparigi, A. et al. (2002). "High circulating ghrelin: a potential cause for hyperphagia and obesity in Prader-Willi syndrome," J Clin Endocrinol Metab 87:5461-5464.

Dimitropoulos, A. et al. (2000). "Appetitive behavior, compulsivity and neurochemistry in Prader-Willi syndrome," MRDD Res Reviews 6:125-130.

Eiholzer, U. et al. (1998). "Low insulin, IGF-I and IGFBP-3 levels in children with Prader-Labhart-Willi syndrome," Eur. J. Pediatr. 157:890-893.

European Examination Report dated Nov. 21, 2011, for EP Application No. 10 159 141.0, 4 pages.

Fieldstone, A. et al. (1998). "Food intake in Prader-Willi syndrome and controls with obesity after administration f a benzodiazepine receptor agonist," Obes Res 6(1):29-33.

Final Office Action dated Oct. 17, 2014, for U.S. Appl. No. 12/370,456, filed Feb. 12, 2009, 14 pages.

Final Office Action dated Mar. 8, 2012, for U.S. Appl. No. 12/370,456, filed Feb. 12, 2009, 13 pages.

Geuns, E. et al. (2003). "Methylation imprints of the imprint control region of the SRNPN-gene in human gametes and preimplantation embryos," Hum Mol Genet 12:2873-2879.

(56) References Cited

OTHER PUBLICATIONS

Goldstone A.P. et al. (2005). "Fasting and postprandial hyperghrelinemia in Prader-Willi syndrome is partially explained by hypoinsulinemia, and is not due to peptide YY3-36 deficiency or seen in hypothalamic obesity due to craniopharyngioma," *J Clin Endocrinol Metab* 90(5):2681-2690.

Goldstone, A.P. et al. (2002). "Hypothalamic NPY and agouti-related protein are increased in human illness but not in Prader-Willi syndrome and other obese subjects," *J. Clin. Endocrino. Metab.* 87:927-937.

Güçlü, F. et al. (2004). "Effects of a statin group drug, pravastatin, on the insulin resistance in patients with metabolic syndrome," Biomedicine & Pharmacotherapy 58:614-618.

Hall, B.D. et al. (1972). "Prader-Willi syndrome: A resumé of 32 cases including an instance of affected first cousins, one of whom is of normal stature and intelligence," J Pediatr 81:286-293.

Haqq, A.M. et al. (2003). "Serum ghrelin levels are inversely correlated with body mass index, age, and insulin concentrations in normal children and are markedly increased in Prader-Willi syndrome," J Clin Endocrinol Metab 88:174-178.

Heymsfield, S.B. et al. (2014). "Hyperphagia: Current Concepts and Future Directions Proceedings of the $2^{nd}$ International Conference on Hyperphagia," Obesity 22:S1-S17.

Holland, A.J. et al. (1993). "Measurement of excessive appetite and metabolic changes in Prader-Willi syndrome," Int J Obes Relat Metab Disord 17(9):527-532.

Holm, V.A. (1976). "Food and children with Prader-Willi syndrome," Am J Dis Child 130:1063-1067.

Honey et al., Clinical and hemodynamic effects of diazoxide in primary pulmonary hypertension, *Thorax* 35(4):269-276 (1980).

Höybye, C. (2004). "Endocrine and metabolic aspects of adult Prader-Willi syndrome with special emphasis on the effect of growth hormone treatment," *Growth Horm. IGF Res.* 14:1-15.

International Search Report dated Feb. 2, 2016, for PCT Application No. PCT/US2015/60455, filed on Nov. 12, 2015, 3 pp.

International Search Report dated Jun. 16, 2006, for PCT Application No. PCT/US2005/30481, filed on Aug. 25, 2005, 1 page.

International Search Report dated Jun. 21, 2013, for PCT Application No. PCT/US2013/027676, filed on Feb. 25, 2013, 4 pages.

Ishihara, A. et al. (2002). "Blockade of body weight gain and plasma corticosterone levels in Zucker fatty rats using an orally active neuropeptide Y Y1 antagonist," Br J Pharmacol 136:341-346.

Lindgren, A.C. et al. (2000). "Eating behavior in Prader-Willi syndrome, normal weight, and obese control groups," *J. Pediatr.* 137:50-55.

Lindgren, A.C. et al. (1999). "Growth hormone treatment of children with Prader-Willi syndrome: effects on glucose and insulin homeostasis," *Horm. Res.* 51:157-161.

Liu, R. (2000). "Water-Insoluble Drug Formulation", Chapter 11, CRC Press LLC, pp. 405-425.

Marugo et al., "Moderate dose diazoxide treatment on weight loss in obese patients", Boll Spec It Biol Sper 1977, vol. 53, pp. 1860-1866 (with English Translation).

McClain, C.J. et al. (2004). "Mechanisms of non-alcoholic steatohepatitis," Alcohol 34:67-79.

Non-Final Office Action dated Nov. 16, 2016, for U.S. Appl. No. 14/940,018, filed Nov. 12, 2015, 13 pages.

Non-Final Office Action dated Aug. 1, 2013, for U.S. Appl. No. 12/368,215, filed Feb. 9, 2009, 12 pages.

Non-Final Office Action dated May 28, 2014, for U.S. Appl. No. 12/370,456, filed Feb. 12, 2009, 17 pages.

Notice of Allowance dated Feb. 1, 2017, for U.S. Appl. No. 14/940,018, filed Nov. 12, 2015, 8 pages.

Raffa et al., "1,2,4-Benzothiadiazine Derivatives Research. Note XI. Reaction of 3-chloroalkyl-1,2,4-benzothiadiazine 1,1-dioxide with dialkylaminoalcohols," Farmaco Edizione Scientifica, 1960, vol. 15, pp. 655-667 (with English summary).

Raffa et al., "1,2,4-Benzothiadiazine Derivatives Research. Note XII. Action of diazomethane on 6-chloro-7-sulfamyl-3-oxodihydro-1,2,4-benzo-thiadiazine 1,1-dioxide," Farmaco Edizione Scientifica, 1960, vol. 15, PD. 668-679 (with English summary).

Raffa et al., "1,2,4-Benzothiadiazine Derivatives Research. Note )0.11. Relation between 3-oxodihydro-1,2,4-benzothiadiazine 1,1-dioxide or its Derivatives and Heterocyclic Bases in Presence of Arylsulfonyl Chlorides," Farmaco Edizione Scientifica, 1961, vol. 16, pp. 3-13 (with English summary).

Raffa et al., "Cardiovascular action of 1,2,4-benzothiadiazine 1,1-dioxides. II," Farmaco Edizione Scientifica, 1965, vol. 20(9), pp. 647-661 (with English summary).

Sekiya, M. et al. (2005). "Effects of the Long-Term Administration of Nicorandil on Vascular Encothelial Function and the Progression of Arteriosclerosis," J Cardiovsac Pharmacol. 46:63-67.

Shapira, N.A. et al. (2005). "Satiety dysfunction in Prader-Willi syndrome demonstrated by fMRI," J Neurol Neurosurg Psychiatry 76:260-262.

Spergel, G. et al. (1966). "Effects of Diazoxide Administration on Plasma Glucose, Insulin, and Lipids in Von Gierke's Disease," Diabetes 15:406-410.

Swaab, D.F. (1997). "Prader-Willi syndrome and the hypothalamus," Acta Paediatr Suppl 423:50-54.

Vansheidt, A.A. et al. (1961). "Polymerization of Cyclic trimer N-methyleneacrylamide in Solution and in the Crystalline State, and Plastics based on the Polymer," Department of Plastics Technology, Lensoviet Technological Institute, Translated from Zhurnal Prikladnoi Khimii 34(4):895-902 (7 total pages, 859-865).

Written Opinion of the International Searching Authority dated Feb. 2, 2016, for PCT Application No. PCT/US2015/60455, filed on Nov. 12, 2015, 8 pages.

Written Opinion of the International Searching Authority dated Jun. 16, 2006, for PCT Application No. PCT/US2005/30481, filed on Aug. 25, 2005, 3 pages.

Written Opinion of the International Searching Authority dated Dec. 6, 2007, for PCT Application No. PCT/US2006/48711, filed on Dec. 20, 2006, 8 pages.

Written Opinion of the International Searching Authority dated Sep. 30, 2008, for PCT Application No. PCT/US2008/68936, filed on Jul. 1, 2008, 7 pages.

Written Opinion of the International Searching Authority dated Jun. 21, 2013, for PCT Application No. PCT/US2013/027676, filed on Feb. 25, 2013, 6 pages.

Zellweger, H. (1968). "Syndrome of hypotonia-hypomentia-hypogonadism-obesity (HHHO) or Prader-Willi syndrome," Am J Disabled Child 115:588-598.

Zipf, W.B. et al. (1983). "Pancreatic polypeptide responses to protein meal challenges in obese but otherwise normal children and obese children with Prader-Willi syndrome," J Clin Endocrinol Metab 57:1074-1080.

Zucker, L.M., et al. (1961). "Fatty, a new mutation in the rat," J Heredit 52:275-278.

\* cited by examiner

PHARMACEUTICAL FORMULATIONS OF POTASSIUM ATP CHANNEL OPENERS AND USES THEREOF

CROSS REFERENCE TO RELATED APPLICATIONS

This application is a divisional application of U.S. Ser. No. 12/370,456, filed Feb. 12, 2009, which is a divisional application of U.S. Ser. No. 11/212,130, filed Aug. 25, 2005, which claims priority to U.S. Ser. No. 60/668,912, filed Apr. 6, 2005, U.S. Ser. No. 60/654,571, filed Feb. 22, 2005, U.S. Ser. No. 60/624,219, filed Nov. 3, 2004, and U.S. Ser. No. 60/604,085, filed Aug. 25, 2004, each of which is incorporated herein in its entirety. Also incorporated herein by reference is PCT International application serial number PCT/US2005/030481, filed Aug. 25, 2005.

FIELD OF THE INVENTION

The present invention relates to pharmaceutical formulations of potassium ATP ($K_{ATP}$) channel openers and their use for treatment of various diseases and conditions such as diabetes and obesity.

BACKGROUND OF THE INVENTION

The following description of the background of the invention is provided simply as an aid in understanding the invention and is not admitted to describe or constitute prior art to the invention.

ATP-sensitive potassium ($K_{ATP}$) channels play important roles in a variety of tissues by coupling cellular metabolism to electrical activity. The $K_{ATP}$ channel has been identified as an octameric complex of two unrelated proteins, which assemble in a 4:4 stoichiometry. The first is a pore forming subunit, Kir6.x, which forms an inwardly rectifying $K^+$ channel; the second is an ABC (ATP binding cassette) transporter, also known as the sulfonylurea receptor (SURx) (Babenko, et al., *Annu. Rev. Physiol.*, 60:667-687 (1998)). The Kir6.x pore forming subunit is common for many types of $K_{ATP}$ channels, and has two putative transmembrane domains (identified as TM1 and TM2), which are linked by a pore loop (H5). The subunit that comprises the SUR receptor includes multiple membrane-spanning domains and two nucleotide-binding folds.

According to their tissue localization, $K_{ATP}$ channels exist in different isoforms or subspecies resulting from the assembly of the SUR and Kir subunits in multiple combinations. The combination of the SUR1 with the Kir6.2 subunits (SUR1/Kir6.2) typically forms the adipocyte and pancreatic B-cell type $K_{ATP}$ channels, whereas the SUR2A/Kir6.2 and the SUR2B/Kir6.2 or Kir6.1 combinations typically form the cardiac type and the smooth muscle type $K_{ATP}$ channels, respectively (Babenko, et al., *Annu. Rev. Physiol.*, 60:667-687 (1998)). There is also evidence that the channel may include Kir2.x subunits. This class of potassium channels are inhibited by intracellular ATP and activated by intracellular nucleoside diphosphates. Such $K_{ATP}$ channels link the metabolic status of the cells to the plasma membrane potential and in this way play a key role in regulating cellular activity. In most excitatory cells, $K_{ATP}$ channels are closed under normal physiological conditions and open when the tissue is metabolically compromised (e.g. when the (ATP:ADP) ratio falls). This promotes K+ efflux and cell hyperpolarization, thereby preventing voltage-operated Ca2+ channels (VOCs) from opening. (*Prog Res Research*, (2001) 31:77-80).

Potassium channel openers (PCOs or KCOs) (also referred to as channel activators or channel agonists), are a structurally diverse group of compounds with no apparent common pharmacophore linking their ability to antagonize the inhibition of $K_{ATP}$ channels by intracellular nucleotides. Diazoxide is a PCO that stimulates $K_{ATP}$ channels in pancreatic β-cells (see Trube, et al., *Pfluegers Arch kEur J Physiol*, 407, 493-99 (1986)). Pinacidil and chromakalim are PCOs that activate sarcolemmal potassium channels (see Escande, et al., *Biochem Biophys Res Commun*, 154, 620-625 (1988); Babenko, et al., *J Biol Chem*, 275(2), 717-720 (2000)). Responsiveness to diazoxide has been shown to reside in the $6^{th}$ through $11^{th}$ predicted transmembrane domains (TMD6-11) and the first nucleotide-binding fold (NBF1) of the SUR1 subunit.

Diazoxide, which is a nondiuretic benzothiadiazine derivative having the formula 7-chloro-3-methyl-2H-1,2,4-benzothiadiazine 1,1-dioxide (empirical formula $C_8H_7ClN_2O_2S$), is commercialized in three distinct formulations to treat two different disease indications; 1) hypertensive emergencies and 2) hyperinsulinemic hypoglycemic conditions. Hypertensive emergencies are treated with Hyperstat IV, an aqueous formulation of diazoxide for intravenous use, adjusted to pH 11.6 with sodium hydroxide. Hyperstat IV is administered as a bolus dose into a peripheral vein to treat malignant hypertension or sulfonylurea overdose. In this use, diazoxide acts to open potassium channels in vascular smooth muscle, stabilizing the membrane potential at the resting level, and preventing vascular smooth muscle contraction.

Hyperinsulinemic hypoglycemic conditions are treated with Proglycem, an oral pharmaceutical version of diazoxide useful for administration to infants, children and adults. It is available as a chocolate mint flavored oral suspension, which includes 7.25% alcohol, sorbitol, chocolate cream flavor, propylene glycol, magnesium aluminum silicate, carboxymethylcellulose sodium, mint flavor, sodium benzoate, methylparaben, hydrochloric acid to adjust the pH, poloxamer 188, propylparaben and water. Diazoxide is also available as a capsule with 50 or 100 mg of diazoxide including lactose and magnesium stearate.

Several experimental formulations of diazoxide have been tested in humans and animals. These include an oral solution tested in pharmacodynamic and pharmacokinetic studies and a tablet formulation under development as an anti-hypertensive, but never commercialized (see Calesnick, et al., *J. Pharm. Sci.* 54:1277-1280 (1965); Reddy, et al., *AAPS Pharm Sci Tech* 4(4):1-98, 9 (2003); U.S. Pat. No. 6,361,795).

Current oral formulations of diazoxide are labeled for dosing two or three times per day at 8 or 12 hour intervals. Most patients receiving diazoxide are dosed three times per day. Commercial and experimental formulations of diazoxide are characterized by rapid drug release following ingestion with completion of release in approximately 2 hours.

Current oral formulations of diazoxide in therapeutic use result in a range of adverse side effects including dyspepsia, nausea, diarrhea, fluid retention, edema, reduced rates of excretion of sodium, chloride, and uric acid, hyperglycemia, vomiting, abdominal pain, ileus, tachycardia, palpitations, and headache (see current packaging insert for the Proglycem). Oral treatment with diazoxide is used in individuals experiencing serious disease where failing to treat results in significant morbidity and mortality. The adverse side effects from oral administration are tolerated because the benefits of treatment are substantial. The adverse side effects profile of oral diazoxide limit the utility of the drug in treating obese patients at doses within the labeled range of 3 to 8 mg/kg per day.

The effect of diazoxide in animal models of diabetes and obesity (e.g. obese and lean Zucker rats) has been reported. See e.g. Alemzadeh et al. (*Endocrinology* 133:705-712 (1993), Alemzadeh et al. (*Metabolism* 45:334-341 (1996)), Alemzadeh et al. (*Endocrinology* 140:3197-3202 (1999)), Stanridge et al. (FASEB J 14:455-460 (2000)), Alemzadeh et al. (Med Sci Monit 10(3): BR53-60 (2004)), Alemzadeh and Tushaus (*Endocrinology* 145(12):3476-3484 (2004)), Aizawa et al. (*J of Pharma Exp Ther* 275(1): 194-199 (1995)), and Surwit et al. (*Endocrinology* 141:3630-3637 (2000)).

The effect of diazoxide in humans with obesity or diabetes has been reported. See e.g., Wigand and Blackard (*Diabetes* 28(4):287-291 (1979); evaluation of diazoxide on insulin receptors), Ratzmann et al. (*Int J Obesity* 7(5):453-458 (1983); glucose tolerance and insulin sensitivity in moderately obese patients), Marugo et al. (*Boll Spec It Biol Sper* 53:1860-1866 (1977); moderate dose diazoxide treatment on weight loss in obese patients), Alemzadeh et al. (*J Clin Endocr Metab* 83:1911-1915 (1998); low dose diazoxide treatment on weight loss in obese hyperinsulinemic patients), Guldstrand et al. (*Diabetes and Metabolism* 28:448-456 (2002); diazoxide in obese type II diabetic patients), Ortqvist et al. (*Diabetes Care* 27(9):2191-2197 (2004); beta-cell function measured by circulating C-peptide in children at clinical onset of type 1 diabetes), Bjork et al. (*Diabetes Care* 21(3):427-430 (1998); effect of diazoxide on residual insulin secretion in adult type I diabetes patients), and Qvigstad et al., (*Diabetic Medicine* 21:73-76 (2004)).

U.S. Pat. No. 5,284,845 describes a method for normalizing blood glucose and insulin levels in an individual exhibiting normal fasting blood glucose and insulin levels and exhibiting in an oral glucose tolerance test, elevated glucose levels and at least one insulin level abnormality selected from the group consisting of a delayed insulin peak, an exaggerated insulin peak and a secondary elevated insulin peak. According to this reference, the method includes administering diazoxide in an amount from about 0.4 to about 0.8 mg/kg body weight before each meal in an amount effective to normalize the blood glucose and insulin levels.

U.S. Pat. No. 6,197,765 describes administration of diazoxide for treatment for syndrome-X, and resulting complications, that include hyperlipidemia, hypertension, central obesity, hyperinsulinemia and impaired glucose intolerance. According to this reference, diazoxide interferes with pancreatic islet function by ablating endogenous insulin secretion resulting in a state of insulin deficiency and high blood glucose levels equivalent to that of diabetic patients that depend on exogenous insulin administration for normalization of their blood glucose levels.

U.S. Pat. No. 2,986,573 describes diazoxide and alkali metal salts for the treatment of hypertension.

U.S. Pat. No. 5,629,045 describes diazoxide for topical ophthalmic administration.

WO 98/10786 describes use of diazoxide in the treatment of X-syndrome including obesity associated therewith.

U.S. Patent publication no. 2003/0035106 describes diazoxide containing compounds for reducing the consumption of fat-containing foods.

U.S. Patent publication no. 2004/0204472 describes the use of a Cox-2 inhibitor plus diazoxide in the treatment of obesity.

U.S. Patent publication no. 2002/0035106 describes use of $K_{ATP}$ channel openers including diazoxide and metal salts for reducing the consumption of fat containing food.

SUMMARY OF THE INVENTION

Provided herein are pharmaceutical formulations of $K_{ATP}$ channel openers and their use for treatment of various diseases and conditions including diabetes and obesity. Such formulations are characterized as being bioavailable. A $K_{ATP}$ channel opener as used herein has any one or more of the following properties: (1) opening SUR1/Kir6.2 potassium channels; (2) binding to the SUR1 subunit of $K_{ATP}$ channels; and (3) inhibiting glucose induced release of insulin following administration of the compound in vivo. Preferably, $K_{ATP}$ channel openers are $K_{ATP}$ channel openers with all three properties. $K_{ATP}$ channel openers as defined above preferably have the structure of compounds of Formulas I-VII as set forth below.

$K_{ATP}$ channel openers defined by Formulas I are as follows:

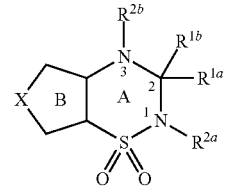

Formula I wherein:

$R^{1a}$ and $R^{1b}$, when present, are independently selected from the group consisting of hydrogen, lower alkyl, substituted lower alkyl, cycloalkyl, substituted cycloalkyl, amino, and substituted amino;

$R^{2a}$ and $R^{2b}$, when present, are independently selected from the group consisting of hydrogen, and lower alkyl;

X is a 1, 2 or 3 atom chain, wherein each atom is independently selected from carbon, sulfur and nitrogen, and each atom is optionally substituted with halogen, hydroxyl, lower alkyl, substituted lower alkyl, lower alkoxy, cycloalkyl, substituted cycloalkyl, substituted lower alkoxy, amino, and substituted amino;

wherein rings A and B are each independently saturated, monounsaturated, polyunsaturated or aromatic;

and all bioequivalents including salts, prodrugs and isomers thereof.

In particular embodiments, compounds of Formula I may include a double bond between either positions 1 and 2 or positions 2 and 3 of Ring A. When a double bond is present between positions 1 and 2 of Ring A, $R^{2a}$ is absent and one of $R^{1a}$ and $R^{1b}$ are absent. When a double bond is present between positions 2 and 3 of Ring A, $R^{2b}$ is absent and one of $R^{1a}$ and $R^{1b}$ are absent. In a preferred embodiment, $R^{1a}$ and $R^{1b}$ are not amino. In another preferred embodiment, Ring B does not include any heteroatoms.

$K_{ATP}$ channel openers defined by Formulas II being a subgenera of Formula I are as follows:

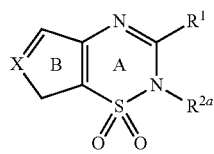

Formula II wherein:
- R[1] is selected from the group consisting of hydrogen, lower alkyl, substituted lower alkyl, cycloalkyl, substituted cycloalkyl, amino, and substituted amino;
- R[2a] is selected from the group consisting of hydrogen, and lower alkyl;
- X is a 1, 2 or 3 atom chain, wherein each atom is independently selected from carbon, sulfur and nitrogen, and each atom is optionally substituted with halogen, hydroxyl, lower alkyl, substituted lower alkyl, lower alkoxy, cycloalkyl, substituted cycloalkyl, substituted lower alkoxy, amino, and substituted amino;
- wherein ring B is saturated, monounsaturated, polyunsaturated or aromatic;
- and all bioequivalents including salts, prodrugs and isomers thereof.

In particular embodiments of Formula II, X is C(R$^a$)C(R$^b$), wherein R$^a$ and R$^b$ are independently selected from the group consisting of hydrogen, halogen, lower alkyl, substituted lower alkyl, cycloalkyl, substituted cycloalkyl, lower alkoxy, substituted lower alkoxy, amino, sulfonylamino, aminosulfonyl, sulfonyl, and the like. In further embodiments, R$^a$ and R$^b$ are independently selected from the group consisting of hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, and the like. In a preferred embodiment, R[1] is not amino. In another preferred embodiment, Ring B does not include any heteroatoms.

K$_{ATP}$ channel openers defined by Formulas III being a subgenera of Formula I are as follows:

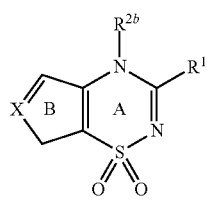

Formula III wherein:
- R[1] is selected from the group consisting of hydrogen, lower alkyl, substituted lower alkyl, cycloalkyl, substituted cycloalkyl, amino, and substituted amino;
- R[2b] is selected from the group consisting of hydrogen, and lower alkyl;
- X is a 1, 2 or 3 atom chain, wherein each atom is independently selected from carbon, sulfur and nitrogen, and each atom is optionally substituted with halogen, hydroxyl, lower alkyl, substituted lower alkyl, lower alkoxy, cycloalkyl, substituted cycloalkyl, substituted lower alkoxy, amino, and substituted amino;
- wherein ring B is saturated, monounsaturated, polyunsaturated or aromatic;
- and all bioequivalents including salts, prodrugs and isomers thereof.

In particular embodiments of Formula III, X is C(R$^a$)C(R$^b$), wherein R$^a$ and R$^b$ are independently selected from the group consisting of hydrogen, halogen, lower alkyl, substituted lower alkyl, cycloalkyl, substituted cycloalkyl, lower alkoxy, substituted lower alkoxy, amino, sulfonylamino, aminosulfonyl, sulfonyl, and the like. In further embodiments, R$^a$ and R$^b$ are independently selected from the group consisting of hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, and the like. In a preferred embodiment, R[1] is not amino. In another preferred embodiment, Ring B does not include any heteroatoms.

K$_{ATP}$ channel openers defined by Formulas IV being a subgenera of Formula I are as follows:

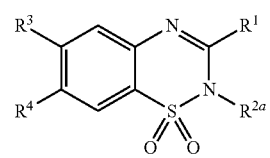

Formula IV wherein:
- R[1] is selected from the group consisting of hydrogen, lower alkyl, substituted lower alkyl, cycloalkyl, amino, and substituted lower amino;
- R[2a] is selected from the group consisting of hydrogen, lower alkyl, and substituted lower alkyl;
- R[3] is selected from the group consisting of hydrogen, halogen, lower alkyl, substituted lower alkyl, amino, and substituted amino;
- R[4] is selected from the group consisting of hydrogen, halogen, lower alkyl, substituted lower alkyl, amino, and substituted amino;
- and all bioequivalents including salts, prodrugs and isomers thereof.

In particular embodiments of Formula IV, R[1] is a lower alkyl, (preferably ethyl or methyl); R[2a] is hydrogen; and R[3] and R[4] are each independently halogen.

In a preferred embodiment of Formula IV, R[1] is not amino.

In another embodiment of Formula IV, R[1] is methyl; R[2a] is hydrogen; R[3] is selected from the group consisting of hydrogen, halogen, lower alkyl, substituted lower alkyl, amino, substituted amino, cycloalkyl, and substituted cycloalkyl; and R[4] is chlorine.

K$_{ATP}$ channel openers defined by Formulas V being a subgenera of Formula I are as follows:

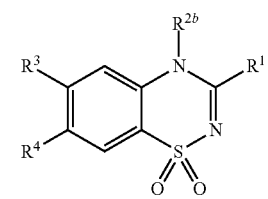

Formula V wherein:
R$^1$ is selected from the group consisting of hydrogen, lower alkyl, substituted lower alkyl, cycloalkyl, amino, and substituted lower amino;
R$^{2b}$ is selected from the group consisting of hydrogen, lower alkyl, and substituted lower alkyl;
R$^3$ is selected from the group consisting of hydrogen, halogen, lower alkyl, substituted lower alkyl, amino, and substituted amino;
R$^4$ is selected from the group consisting of hydrogen, halogen, lower alkyl, substituted lower alkyl, amino, and substituted amino;
and all bioequivalents including salts, prodrugs and isomers thereof.

In particular embodiments of Formula V, R$^1$ is a lower alkyl, (preferably ethyl or methyl); R$^{2b}$ is hydrogen; and R$^3$ and R$^4$ are each independently halogen.

In a preferred embodiment of Formula V, R$^1$ is not amino.

In another embodiment of Formula V, R$^1$ is methyl; R$^{2b}$ is hydrogen; R$^3$ is selected from the group consisting of hydrogen, halogen, lower alkyl, substituted lower alkyl, amino, substituted amino, cycloalkyl, and substituted cycloalkyl; and R$^4$ is chlorine.

K$_{ATP}$ channel openers defined by Formulas VI are as follows:

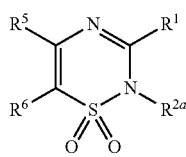

Formula VI wherein:
R$^1$ is selected from the group consisting of hydrogen, lower alkyl, substituted lower alkyl, cycloalkyl, substituted cycloalkyl, amino, and substituted lower amino, or R$^1$ can cooperate with R$^5$ or R$^6$ to form an additional ring;
R$^{2a}$ is selected from the group consisting of hydrogen, lower alkyl, and substituted lower alkyl;
R$^5$ is selected from the group consisting of hydrogen, halogen, hydroxyl, lower alkyl, substituted lower alkyl, amino, substituted amino, sulfonyl, aminosulfonyl, and sulfonylamino, or R$^5$ can cooperate with R$^1$ or R$^6$ to form an additional ring;
R$^6$ is selected from the group consisting of hydrogen, halogen, lower alkyl, substituted lower alkyl, amino, substituted amino, sulfonyl, aminosulfonyl, and sulfonylamino, or R$^6$ can cooperate with R$^1$ or R$^5$ to form an additional ring;
wherein the ring formed by the cooperation of R$^1$ and R$^5$, or R$^1$ and R6, or R$^5$ and R$^6$ is saturated, monounsaturated, polyunsaturated or aromatic;
wherein the ring formed by the cooperation of R$^1$ and R$^5$, or R$^1$ and R$^6$, or R$^5$ and R$^6$ is optionally substituted with halogen, hydroxyl, lower alkyl, substituted lower alkyl, amino, substituted amino, sulfonyl, aminosulfonyl, and sulfonylamino;
and all bioequivalents including salts, prodrugs and isomers thereof.

In a preferred embodiment, R$^1$ is not an amino substituent.

In another embodiment of Formula VI, R$^5$ and R$^6$ combine to form a 6 membered ring. In another embodiment, R$^5$ and R$^6$ combine to form a 6 membered ring wherein at least one nitrogen is present. Preferably, the ring formed by R$^5$ and R$^6$ does not include any heteroatoms.

K$_{ATP}$ channel openers defined by Formulas VII are as follows:

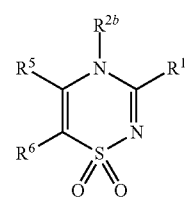

Formula VII wherein:
R$^1$ is selected from the group consisting of hydrogen, lower alkyl, substituted lower alkyl, cycloalkyl, substituted cycloalkyl, amino, and substituted lower amino, or R$^1$ can cooperate with R$^5$ or R$^6$ to form an additional ring;
R$^{2b}$ is selected from the group consisting of hydrogen, lower alkyl, and substituted lower alkyl;
R$^5$ is selected from the group consisting of hydrogen, halogen, hydroxyl, lower alkyl, substituted lower alkyl, amino, substituted amino, sulfonyl, aminosulfonyl, and sulfonylamino, or R$^5$ can cooperate with R$^1$ or R$^6$ to form an additional ring;
R$^6$ is selected from the group consisting of hydrogen, halogen, lower alkyl, substituted lower alkyl, amino, substituted amino, sulfonyl, aminosulfonyl, and sulfonylamino, or R6 can cooperate with R$^1$ or R$^5$ to form an additional ring;
wherein the ring formed by the cooperation of R$^1$ and R$^5$, or R$^1$ and R6, or R$^5$ and R$^6$ is saturated, monounsaturated, polyunsaturated or aromatic;
wherein the ring formed by the cooperation of R$^1$ and R$^5$, or R$^1$ and R$^6$, or R$^5$ and R$^6$ is optionally substituted with halogen, hydroxyl, lower alkyl, substituted lower alkyl, amino, substituted amino, sulfonyl, aminosulfonyl, and sulfonylamino;
and all bioequivalents including salts, prodrugs and isomers thereof.

In a preferred embodiment, R$^1$ is not an amino substituent.

In another embodiment of Formula VI, R$^5$ and R$^6$ combine to form a 6 membered ring. In another embodiment, R$^5$ and R$^6$ combine to form a 6 membered ring wherein at least one nitrogen is present. Preferably, the ring formed by R$^5$ and R$^6$ does not include any heteroatoms.

Unless otherwise indicated, reference in this application to K$_{ATP}$ channel openers should be understood to refer to a K$_{ATP}$ channel openers having one or more and preferably all three of the following properties: (1) opening SUR1/Kir6.2 potassium channels; (2) binding to the SUR1 subunit of K$_{ATP}$ channels; and (3) inhibiting glucose induced release of insulin following administration of the compound in vivo. Such K$_{ATP}$ channel openers preferably have the structure of any of the compounds of Formula I-VII, or more preferably Formula I-VII where R$^1$ is not amino and also where ring B or its equivalent does not include any heteroatoms, or more preferably, any of the compounds of Formula II or III, or more preferably, any of the compounds of Formula II or III where R$^1$ is not amino and also where ring B or its equivalent does not include any heteroatoms, or more preferably, the structure is diazoxide. Structural variants or bioequivalents of the compounds of any of Formula I-VII such as derivatives, salts, prodrugs or isomers are also contemplated. Other $K_{ATP}$ channel openers that are contemplated for use herein include BPDZ62, BPDZ 73, NN414, BPDZ 154.

In vitro analysis of glucose induced release of insulin via $K_{ATP}$ channel openers can be determined using rat islets as provided by De Tullio, et al., *J. Med. Chem.*, 46:3342-3353 (2003) or by using human islets as provided by Bjorklund, et al., *Diabetes*, 49:1840-1848 (2000).

Provided herein are formulations, such as controlled release pharmaceutical formulations, of $K_{ATP}$ channel openers and bioquivalents thereof. In one embodiment, the controlled release formulations are formulated for oral administration. Such formulations contain in a single administration dosage between 10 and 100 mg, between 25 and 100 mg, between 100 and 200 mg, between 200 and 300 mg, between 300 and 500 mg or between 500 and 2000 mg of the $K_{ATP}$ channel openers. In certain embodiments, the dosage of the $K_{ATP}$ channel openers contained in a formulation may be determined based on the weight of the patient for which it is to be administered, i.e., the formulation may contain in a single administration dosage between 0.1-20 mg of the $K_{ATP}$ channel opener per kg of the patient's body weight, or between 0.1-0.5 mg of the $K_{ATP}$ channel opener per kg of the patient's body weight; or between 0.5-1 mg of the $K_{ATP}$ channel opener per kg of the patient's body weight; or between 1-2 mg of the $K_{ATP}$ channel opener per kg of the patient's body weight, or between 2-5 mg of the $K_{ATP}$ channel opener per kg of the patient's body weight, or between 5-10 mg of the $K_{ATP}$ channel opener per kg of the patient's body weight, or between 10-15 mg of the $K_{ATP}$ channel opener per kg of the patient's body weight, or between 15-20 mg of the $K_{ATP}$ channel opener per kg of the patient's body weight.

Also provided herein are controlled release pharmaceutical formulations containing $K_{ATP}$ channel openers obtained by at least one of the following: (a) particle size reduction involving comminution, spray drying, or other micronising techniques, (b) use of a pharmaceutical salt of the $K_{ATP}$ channel opener, (c) use of an ion exchange resin, (d) use of inclusion complexes, for example cyclodextrin, (e) compaction of the $K_{ATP}$ channel opener with a solubilizing agent including a low viscosity hypromellose, low viscosity metylcellulose or similarly functioning excipient or combinations thereof, (f) associating the $K_{ATP}$ channel opener with a salt prior to formulation, (g) use of a solid dispersion of the $K_{ATP}$ channel opener, (h) use of a self emulsifying system, (i) addition of one or more surfactants to the formulation, (j) use of nanoparticles, or (k) combinations of these approaches.

Further provided herein are controlled release pharmaceutical formulations containing $K_{ATP}$ channel openers which include at least one component that substantially inhibits release of the $K_{ATP}$ channel activator from the formulation until after gastric transit. As used herein, "substantially inhibits" means less than 15% release, more preferably at least less than 10% release, or more preferably at least less than 5% release of the drug from the formulation during gastric transport. Release can be measured in a standard USP based in-vitro gastric dissolution assay in a calibrated dissolution apparatus. (U.S. Pharmacopeia, Chapter 711 (2005)).

Also provided are oral pharmaceutical formulations of $K_{ATP}$ channel openers which include at least one component $K_{ATP}$ channel openers which include at least one component that substantially inhibits release of the $K_{ATP}$ channel opener from the formulation until after gastric transit. Substantial inhibition of drug release during gastric transit is achieved by inclusion of a component in the formulation selected from the group consisting of: (a) a pH sensitive polymer or co-polymer applied as a compression coating on a tablet, (b) a pH sensitive polymer or co-polymer applied as a thin film on a tablet, (c) a pH sensitive polymer or co-polymer applied as a thin film to an encapsulation system, (d) a pH sensitive polymer or co-polymer applied to encapsulated microparticles, (e) a non-aqueous-soluble polymer or copolymer applied as a compression coating on a tablet, (f) a non-aqueous-soluble polymer or co-polymer applied as a thin film on a tablet, (g) a non-aqueous soluble polymer applied as a thin film to an encapsulation system, (h) a non-aqueous soluble polymer applied to microparticles, (i) incorporation of the formulation in an osmotic pump system, (j) use of systems controlled by ion exchange resins, and (k) combinations of these approaches, wherein the pH sensitive polymer or co-polymer is resistant to degradation under acid conditions.

Also provided herein are controlled release pharmaceutical formulations of $K_{ATP}$ channel openers, wherein the formulation includes at least one component that contributes to sustained release of a $K_{ATP}$ channel opener over a period of 2-4 hours following administration, or over a period of 4-8 hours following administration, or over a period of more than 8-24 hours following administration. These formulations are characterized in having one of the following components: (a) a pH sensitive polymeric coating, (b) a hydrogel coating, (c) a film coating that controls the rate of diffusion of the drug from a coated matrix, (d) an erodable matrix that controls rate of drug release, (e) polymer coated pellets, granules or microparticles of drug which can be further encapsulated or compressed into a tablet, (f) an osmotic pump system containing the drug, (g) a compression coated tablet form of the drug, or (h) combinations of these approaches.

As used herein, an erodable matrix is the core of a tablet formulation that, upon exposure to an aqueous environment, begins a process of disintegration which facilitates the release of drug from the matrix. The rate of release of drug from the tablet is controlled both by the solubility of the drug and the rate of disintegration of the matrix.

The above formulations may further comprise one or more additional pharmaceutically active agents (other than $K_{ATP}$ channel openers) useful for the treatment of a condition selected from the group consisting of obesity, prediabetes, diabetes, hypertension, depression, elevated cholesterol, fluid retention, other obesity associated comorbidities, ischemic and reperfusion injury, epilepsy, schizophrenia, mania, or other psychotic diseases.

Further provided is a controlled release pharmaceutical formulation of a $K_{ATP}$ channel opener wherein administration to an obese, overweight or obesity prone individual results in at least one of the following: (a) inhibition of fasting insulin secretion (b) inhibition of stimulated insulin secretion, (c) elevation of energy expenditure, (d) elevation of beta oxidation of fat, or (e) inhibition of hyperphagia for about 24 hours.

Additionally provided is a controlled release pharmaceutical formulation of a $K_{ATP}$ channel opener wherein administration to an obese, overweight or obesity prone individual results in at least one of the following: (a) inhibition of fasting insulin secretion (b) inhibition of glucose stimulated insulin secretion, (c) elevation of energy expenditure, (d) elevation of beta oxidation of fat, or (e) inhibition of hyperphagia for about 18 hours.

Still further provided is a controlled release pharmaceutical formulation of a $K_{ATP}$ channel opener which upon administration to an obese, overweight or obesity prone individual results in at least one of the following: (a) inhibition of fasting insulin secretion (b) inhibition of glucose stimulated insulin secretion, (c) elevation of energy expenditure, (d) elevation of beta oxidation of fat, or (e) inhibition of hyperphagia for about 24 hours.

Additionally provided is a controlled release pharmaceutical formulation of a $K_{ATP}$ channel opener that upon administration to an obese, overweight or obesity prone individual results in at least one of the following: (a) inhibition of fasting insulin secretion (b) inhibition of glucose stimulated insulin secretion, (c) elevation of energy expenditure, (d) elevation of beta oxidation of fat, or (e) inhibition of hyperphagia for about 18 hours.

Provided herein is a method of treating hypoglycemia, the method comprising orally administering a controlled release formulation of a $K_{ATP}$ channel opener.

Further provided herein is a method of treating obesity associated co-morbidities in an obese, overweight or obesity prone individual, the method comprising administering a therapeutically effective amount of a solid oral dosage form of a $K_{ATP}$ channel opener, or controlled release pharmaceutical formulation of a $K_{ATP}$ channel opener. In a preferred embodiment, administration is no more than two times per 24 hours, or once per 24 hours.

Yet further provided herein is a method of achieving weight loss in an obese overweight, or obesity prone individual, the method comprising administering a therapeutically effective amount of a solid oral dosage form of a $K_{ATP}$ channel opener or controlled release pharmaceutical formulation of a $K_{ATP}$ channel opener. In a preferred embodiment, administration is no more than two times per 24 hours, or once per 24 hours. The daily dosage administered is preferably between 50 and 180 mg. In certain embodiments, the obese individual has a body mass index greater than 30 kg/m², or greater than 35 kg/m², or greater than 40 kg/m², or greater than 50 kg/m², or greater than 60 kg/m² at the time the method commences.

Also provided is a method of maintaining a weight loss in an obese overweight, or obesity prone individual, the method comprising administering a therapeutically effective amount of a solid oral dosage form of a $K_{ATP}$ channel opener or controlled release pharmaceutical formulation of a $K_{ATP}$ channel opener. It is preferable to maintain weight in an obese individual once some weight loss has occurred when the alternative is to regain weight. In a preferred embodiment, administration is no more than two times per 24 hours, or once per 24 hours.

Further provided is a method of elevating energy expenditure in an overweight, obese or obesity prone individual, the method comprising administering an effective amount of a solid oral dosage form of a $K_{ATP}$ channel opener or controlled release pharmaceutical formulation of a $K_{ATP}$ channel opener. In a preferred embodiment, administration is no more than two times per 24 hours, or once per 24 hours. In certain embodiments, the individual has a body mass index greater than 20 kg/m2, or greater than 25 kg/m2, or greater than 30 kg/m2, or greater than 35 kg/m², or greater than 40 kg/m2, or greater than 50 kg/m2, or greater than 60 kg/m2 at the time the method commences.

Additionally provided is a method of elevating beta oxidation of fat in an overweight, obese or obesity prone individual, the method comprising administering an effective amount of a solid oral dosage form of a $K_{ATP}$ channel opener or controlled release pharmaceutical formulation of a $K_{ATP}$ channel opener. In a preferred embodiment, administration is no more than two times per 24 hours, or once per 24 hours. In certain embodiments, the individual has a body mass index greater than 20 kg/m2, or greater than 25 kg/m2, or greater than 30 kg/m2, or greater than 35 kg/m², or greater than 40 kg/m2, or greater than 50 kg/m2, or greater than 60 kg/m2 at the time the method commences.

Yet further provided is a method of reducing visceral fat in an overweight, obese or obesity prone individual, the method comprising administering an effective amount of a solid oral dosage form of a $K_{ATP}$ channel opener or controlled release pharmaceutical formulation of a $K_{ATP}$ channel opener. In a preferred embodiment, administration is no more than two times per 24 hours, or once per 24 hours.

Still further provided is a method of delaying or preventing the transition to diabetes of a prediabetic individual comprising administering an effective amount of a $K_{ATP}$ channel opener or controlled release pharmaceutical formulation of a $K_{ATP}$ channel opener. In a preferred embodiment, administration is no more than two times per 24 hours, or once per 24 hours.

Additionally provided is a method of restoring normal glucose tolerance in a prediabetic individual comprising administering an effective amount of a $K_{ATP}$ channel opener or controlled release pharmaceutical formulation of a $K_{ATP}$ channel opener. In a preferred embodiment, administration is no more than two times per 24 hours, or once per 24 hours.

Further provided is a method of restoring normal glucose tolerance in a diabetic individual comprising administering an effective amount of a $K_{ATP}$ channel opener or controlled release pharmaceutical formulation of a $K_{ATP}$ channel opener. In a preferred embodiment, administration is no more than two times per 24 hours, or once per 24 hours.

Still further provided is a method of delaying or preventing progression of diabetes in an individual comprising administering an effective amount of a $K_{ATP}$ channel opener or controlled release pharmaceutical formulation of a $K_{ATP}$ channel opener. In a preferred embodiment, administration is no more than two times per 24 hours, or once per 24 hours.

Also provided is a method to prevent or treat weight gain, impaired glucose tolerance or dyslipidemia associated with the use of anti-psychotics to treat patients comprising the co-administration of an effective amount of a $K_{ATP}$ channel opener or controlled release pharmaceutical formulation of a $K_{ATP}$ channel opener. In a preferred embodiment, administration is no more than two times per 24 hours, or once per 24 hours.

Further provided is a method to treat obesity, or hyperphagia in a Prader-Willi Syndrome patient, a Froelich's Syndrome patient, in a Cohen Syndrome patient, in a Summit Syndrome patient, in an Alstrom Syndrome patient, in a Borjeson Syndrome patient or in a Bardet-Biedl Syndrome patient comprising the administration of an effective amount of a $K_{ATP}$ channel opener or controlled release pharmaceutical formulation of a $K_{ATP}$ channel opener. In a preferred embodiment, administration is no more than two times per 24 hours, or once per 24 hours.

Still further provided is a method to treat obesity or elevated triglycerides in a patient suffering hyperlipoproteinemia type I, type II, type III or type IV comprising administering an effective amount of a $K_{ATP}$ channel opener or controlled release pharmaceutical formulation of a $K_{ATP}$ channel opener. In a preferred embodiment, administration is no more than two times per 24 hours, or once per 24 hours.

Also provided is a method of reducing the incidence of adverse effects from administration of a $K_{ATP}$ channel opener in the treatment of diseases of a subject achieved by any of the following: (a) use of a dosage form that on administration reduces $C_{max}$ relative to the current Proglycem oral suspension or capsule products in order to reduce the incidence of adverse side effects that are associated with peak drug levels, (b) use of a dosage form that delays release until gastric transit is complete in order to reduce the incidence of adverse side effects that are associated with the release of drug in the stomach, (c) initiating dosing at subtherapeutic levels and in a stepwise manner increasing dose daily until the therapeutic dose is achieved wherein the number of steps is 2 to 10 to reduce the incidence of adverse side effects that occur transiently at the initiation of treatment, (d) use of the lowest effective dose to achieve the desired therapeutic effect in order to reduce the incidence of adverse side effects that are dose dependent, or (e) optimizing the timing of administration of dose within the day and relative to meals.

Further provided is a method of preventing weight gain, dyslipidemia or impaired glucose tolerance in a subject treated with an anti-psychotic drug, the method comprising administering a pharmaceutical formulation of a $K_{ATP}$ channel opener.

Yet further provided is a method of treating weight gain, dyslipidemia or impaired glucose tolerance in a subject treated with an anti-psychotic drug, the method comprising administering a pharmaceutical formulation of a $K_{ATP}$ channel opener.

Also provided is a method of treating diseases characterized by obesity, hyperphagia, dyslipidemia, or decreased energy expenditure including (a) Prader Willi Syndrome, (b) Froelich's syndrome, (c) Cohen syndrome, (d) Summit Syndrome, (e) Alstrom, Syndrome, (f) Borjesen Syndrome, (g) Bardet-Biedl Syndrome, or (h) hyperlipoproteinemia type I, II, III, and IV comprising administering a pharmaceutical formulation of a $K_{ATP}$ channel opener.

Further provided is a pharmaceutical formulation of a $K_{ATP}$ channel opener further comprising a pharmaceutically active agent other than the $K_{ATP}$ channel opener. In this formulation, the other pharmaceutically active agent is an agent useful for the treatment of a condition selected from the group consisting of obesity, prediabetes, diabetes, hypertension, depression, elevated cholesterol, fluid retention, or other obesity associated comorbidities, ischemic and reperfusion injury, epilepsy, schizophrenia, mania, and other psychotic condition.

The formulations containing $K_{ATP}$ channel openers described herein provide for improved compliance, efficacy and safety, and for co-formulations with other agents. Included are co-formulations of $K_{ATP}$ channel openers with one or more additional pharmaceutically active agents that have complementary or similar activities or targets. Other pharmaceutical active agents that can be combined with $K_{ATP}$ channel openers to treat obesity or to maintain weight loss in an obesity prone individual include, but are not limited to: sibutramine, orlistat, phentermine, rimonabant, a diuretic, an antiepileptic, or other pharmaceutical active whose therapeutic utility includes weight loss. It is preferable to maintain weight in an obese individual once some weight loss has occurred when the alternative is to regain weight. Other pharmaceutically active agents that may be combined with $K_{ATP}$ channel openers to treat type II diabetes, or prediabetes include acarbose, miglitol, metformin, repaglinide, nateglinide, rosiglitizone, proglitizone, ramipril, metaglidasen, or any other pharmaceutical active that improves insulin sensitivity or glucose utilization or glycemic control where the mode of action is not enhanced insulin secretion. Other pharmaceutical active agent that can be combined with $K_{ATP}$ channel openers to treat obesity associated co-morbidities include a drug active used to lower cholesterol, a drug active used to lower blood pressure, an anti-inflammatory drug that is not a cox-2 inhibitor, a drug that is an antidepressant, a drug used to treat urinary incontinence, or other drug routinely used to treat disease conditions the incidence of which is elevated in overweight or obese patients as compared to normal weight individuals including, but not limited to, drugs to treat atherosclerosis, osteoarthritis, disc herniation, degeneration of knees and hips, breast, endometrium, cervical, colon, leukemia and prostate cancers, hyperlipidemia, asthma/reactive airway disease, gallstones, GERD, obstructive sleep apnea, obesity hypoventilation syndrome, recurrent ventral hernias, menstrual irregularity and infertility.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

The term "pharmaceutically acceptable" indicates that the identified material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

As used herein, the term "composition" refers to a formulation suitable for administration to an intended animal subject for therapeutic purposes that contains at least one pharmaceutically active compound and at least one pharmaceutically acceptable carrier or excipient. Other terms as used herein are defined below.

Adipocyte: An animal connective tissue cell specialized for the synthesis and storage of fat.

Agonist: A chemical compound that has affinity for and stimulates physiological activity at cell receptors normally stimulated by naturally occurring substances, triggering a biochemical response. An agonist of a receptor can also be considered an activator of the receptor.

About: is used herein to mean in quantitative terms plus or minus 10%.

Adipose tissue: Tissue comprised principally of adipocytes.

Adolescent: A person between 10 and 19 years of age.

Adiponectin: A protein hormone produced and secreted exclusively by adipocytes that regulates the metabolism of lipids and glucose. Adiponectin influences the body's response to insulin. Adiponectin also has anti-inflammatory effects on the cells lining the walls of blood vessels.

Amelioration of the symptoms of a particular disorder by administration of a particular pharmaceutical composition: refers to any lessening, whether permanent or temporary, lasting or transient that can be attributed to or associated with administration of the composition.

Analog: a compound that resembles another in structure but differs by at least one atom.

Antagonist: A substance that tends to nullify the action of another, as a drug that binds to a cell receptor without eliciting a biological response.

Atherosclerotic Plaque: A buildup of cholesterol and fatty material within a blood vessel due to the effects of atherosclerosis Bariatric Surgery: a range of surgical procedures which are designed to aid in the management or treatment of obesity and allied diseases.

Beta cell rest: Temporarily placing beta cells in a condition in which there is reduced metabolic stress due to suppressed secretion of insulin.

Bilaminate: A component of a pharmaceutical dosage form that consists of the lamination of two distinct materials.

Bioavailability: Refers to the amount or extent of therapeutically active substance that is released from the drug product and becomes available in the body at the intended site of drug action. The amount or extent of drug released can be established by the pharmacokinetic-parameters, such as the area under the blood or plasma drug concentration-time curve (AUC) and the peak blood or plasma concentration ($C_{max}$) of the drug.

Bioequivalent: Two formulations of the same active substance are bioequivalent when there is no significant difference in the rate and extent to which the active substance becomes available at the site of drug action when administered at the same molar dose under similar conditions. "Formulation" in this definition may include the free base of the active substance or different salts of the active substance. Bioequivalence may be demonstrated through several in vivo and in vitro methods. These methods, in descending order of preference, include pharmacokinetic, pharmacodynamic, clinical and in vitro studies. In particular, bioequivalence is demonstrated using pharmacokinetic measures such as the area under the blood or plasma drug concentration-time curve (AUC) and the peak blood or plasma concentration (Cmax) of the drug, using statistical criteria.

Cannabinoid Receptor: Receptors in the endocannabinoid (EC) system associated with the intake of food and tobacco dependency. Blocking the cannabinoid receptor may reduce dependence on tobacco and the craving for food.

Combination: refers to any association between or among two or more items. The combination can be two or more separate items, such as two compositions or two collections. It can be a mixture thereof, such as a single mixture of the two or more items, or any variation thereof.

Composition: refers to any mixture. It can be a solution, a suspension, liquid, powder, a paste, aqueous, non-aqueous or any combination thereof.

Compression tablet: Tablet formed by the exertion of pressure to a volume of tablet matrix in a die.

Compression coated tablet: A tablet formed by the addition of a coating by compression to a compressed core containing the pharmaceutical active.

Derivative: a chemical substance derived from another substance by modification or substitution.

Daily dosage: the total amount of a drug taken in a 24 hour period whether taken as a single dose or taken in multiple doses.

Diazoxide: 7-chloro-3-methyl-2-H-1,2,4-benzothiadiazine 1,1 dioxide with the empirical formula C8H7ClN2O2S and a molecular weight of 230.7.

Encapsulation system: a structural feature that contains drug within such as a pharmaceutical capsule. A gel into which drug is incorporated also is considered an encapsulation system.

Equivalent amount: an amount of a derivative of a drug that in assays or upon administration to a subject produces an equal effect to a defined amount of the non-derivatized drug.

Fatty acid synthase: The central enzyme of a multienzyme complex that catalyses the formation of palmitate from acetylcoenzyme A, malonylcoenzyme A, and NADPH.

Gastric Lipase: An enzyme secreted into the gastrointestinal tract that catalyzes the hydrolysis of dietary triglycerides.

Glidant: An inactive component of a pharmaceutical formulation that prevents caking of the matrix during processing steps.

Hyperinsulemia: Excessively high blood insulin levels, which is differentiated from hyperinsulinism, excessive secretion of insulin by the pancreatic islets. Hyperinsulinemia may be the result of a variety of conditions, such as obesity and pregnancy.

Hyperinsulinism: Excessive secretion of insulin by the pancreatic islets.

Hyperlipidemia: A general term for elevated concentrations of any or all of the lipids in the plasma, such as cholesterol, triglycerides and lipoproteins.

Hyperphagia: Ingestion of a greater than optimal quantity of food.

Ingredient of a pharmaceutical composition: refers to one or more materials used in the manufacture of a pharmaceutical composition. Ingredient can refer to an active ingredient (an agent) or to other materials in the compositions. Ingredients can include water and other solvents, salts, buffers, surfactants, water, non-aqueous solvents, and flavorings.

Insulin resistance: A condition in which the tissues of the body are diminished in their response to insulin.

Ischemic injury: injury to tissue that results from a low oxygen state usually due to obstruction of the arterial blood supply or inadequate blood flow leading to hypoxia in the tissue.

Ketoacidosis: Acidosis accompanied by the accumulation of ketone bodies (ketosis) in the body tissue and fluids, as in diabetic acidosis.

Kit: refers to a packaged combination. A packaged combination can optionally include a label or labels, instructions and/or reagents for use with the combination.

Kir: Pore forming subunit of the $K_{ATP}$ channel. Also known as the inwardly rectifying subunit of the $K_{ATP}$ channel. Typically existing as Kir6.x and infrequently as Kir2.x subspecies.

$K_{ATP}$ channel: An ATP sensitive potassium ion channel across the cell membrane formed by the association of 4 copies of a sulfonylurea receptor and 4 copies of a pore forming subunit Kir. Agonizing the channel can lead to membrane hyperpolarization.

Leptin: Product (16 kD) of the ob (obesity) locus. It is found in plasma of mammals and exerts a hormonal action, which reduces food uptake and increases energy expenditure.

Lipogenesis: The generation of new lipids, primarily triacylglycerides. It is dependent on the action of multiple distinct enzymes and transport molecules.

Lipolysis: The breakdown of fat by the coordinated action of multiple enzymes.

Lipoprotein lipase: An enzyme of the hydrolase class that catalyses the reaction of triacyglycerol and water to yield diacylglyerol and a fatty acid anion. The enzyme hydrolyses triacylglycerols in chylomicrons, very-low-density lipoproteins, low-density lipoproteins, and diacylglycerols.

Lubricant: An inactive component of a pharmaceutical formulation that provides for the flow of materials in various processing steps, particularly tableting.

Microparticle: A small particulate formed in the process of developing pharmaceutical formulations that may be coated prior to producing the final dosage from.

Obesity: An increase in body weight beyond the limitation of skeletal and physical requirement, as the result of an excessive accumulation of fat in the body. Formally defined as having a body mass index greater than 30 kg/m2.

Obesity Prone: Individuals who because of genetic predisposition or prior history of obesity are at above average risk of becoming obese.

Obesity related co-morbidities: any disease or condition of animals or humans that are increased incidence in obese or overweight individuals. Examples of such conditions include hypertension, prediabetes, type 2 diabetes, osteoarthritis and cardiovascular conditions.

Osmotically controlled release: A pharmaceutical dosage form in which the release of the active drug is principally achieved by the hydration of a swellable component of the formulation.

Overweight: an individual whose weight is above that which is ideal for their height but who fails to meet the criteria for classification as obese. In humans using Body Mass Index (kg/m2) an overweight individuals has a BMI between 25 and 30.

Oxidation of Fat: A series of reactions involving acyl-coenzyme A compounds, whereby these undergo beta oxidation and thioclastic cleavage, with the formation of acetylcoenzyme A; the major pathway of fatty acid catabolism in living tissue.

Pharmaceutical composition: refers a composition that contains an agent and one or more other ingredients that is formulated for administration to a subject. An agent refers to an active ingredient of a pharmaceutical composition. Typically active ingredients are active for treatment of a disease or condition. For example, agents that can be included in pharmaceutical compositions include agents for treating obesity or diabetes. The pharmaceutically active agent can be referred to as "a pharmaceutical active."

Pharmaceutical effect: refers to an effect observed upon administration of an agent intended for treatment of a disease or disorder or for amelioration of the symptoms thereof.

Pharmacodynamic: An effect mediated by drug action.

Pharmacokinetic: Relating to the absorption, distribution, metabolism and elimination of the drug in the body.

Polymorph: A compound that shares the same chemistry but a different crystal structure.

Preadipocyte: A progenitor cell to adipocytes.

Prediabetic: A condition that precedes diagnosis of type II diabetes. Type II diabetes is a form of diabetes mellitus which is characterized by insulin insensitivity or resistance.

Prodrug: refers to a compound which, when metabolized, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

Prolonged Administration (prolonged basis): Administration of a pharmaceutically acceptable formulation of a drug for 7 or more days. Typically, prolonged administration is for at least two weeks, preferably at least one month, and even more preferably at least two months (i.e. at least 8 weeks).

Quick dissolving formulation: a pharmaceutical formulation which upon oral administration may release substantially all of the drug active from the formulation within 10 minutes.

Release formulation (sustained), (or "sustained release formulation"): A formulation of pharmaceutical product that, upon administration to animals, provides for release of the active pharmaceutical over an extended period of time than provided by formulations of the same pharmaceutical active that result in rapid uptake. Similar terms are extended-release, prolonged-release, and slow-release. In all cases, the preparation, by definition, has a reduced rate of release of active substance.

Release formulation (delayed), (or "delayed release formulation"): Delayed-release products are modified-release, but are not extended-release. They involve the release of discrete amount(s) of drug some time after drug administration, e.g. enteric-coated products, and exhibit a lag time during which little or no absorption occurs.

Release formulation (controlled), (or "controlled release formulation"): A formulation of pharmaceutical product that may include both delay of release of pharmaceutical active upon administration and control of release in the manner described for sustained release.

Salt: the neutral, basic or acid compound formed by the union of an acid or an acid radical and a base or basic radical.

Solid oral dosage form: pharmaceutical formulations designed for oral administration including capsules and tablets.

Subject: refers to animals, including mammals, such as human beings.

Sulfonylurea receptor: A component of the $K_{ATP}$ channel responsible for interaction with sulfonylurea, other $K_{ATP}$ channel antagonists, diazoxide and other $K_{ATP}$ channel agonists.

Tablet: Pharmaceutical dosage form that is produced by forming a volume of a matrix containing pharmaceutical active and excipients into a size and shape suitable for oral administration.

Thermogenesis: The physiological process of heat production in the body.

Threshold Concentration: The minimum circulating concentration of a drug required to exert a specific metabolic, physiological or compositional change in the body of a treated human or animal.

Treatment: means any manner in which the symptoms of a condition, disorder or disease or other indication, are ameliorated or otherwise beneficially altered.

Triglyceride: Storage fats of animal and human adipose tissue principally consisting of glycerol esters of saturated fatty acids.

Type I diabetes: A chronic condition in which the pancreas makes little or no insulin because the beta cells have been destroyed.

Uncoupling protein: A family of proteins that allow oxidation in mitochondria to proceed without the usual concomitant phosphorylation to produce ATP.

Visceral fat: Human adipose tissues principally found below the subcutaneous fat and muscle layer in the body.

DETAILED DESCRIPTION OF THE INVENTION

Provided herein are pharmaceutical formulations of particular $K_{ATP}$ channel openers that when administered to subjects achieve novel pharmacodynamic, pharmacokinetic, therapeutic, physiological, and metabolic outcomes. Also provided are pharmaceutical formulations, methods of administration and dosing of particular $K_{ATP}$ channel openers that achieve therapeutic outcomes while reducing the incidence of adverse effects.

In particular, pharmaceutical formulations formulated for oral administration exhibit advantageous properties including: facilitating consistency of absorption, pharmacokinetic and pharmacodynamic responses across treated patients, contributing to patient compliance and improving the safety profile of the product, such as by reducing the frequency of serious adverse effects. Method of treatment of metabolic and other diseases of humans and animals by administering the formulations are also provided.

Compounds of formulas II and III, formulas IV and V, and formulas VI and VII, such as for example, diazoxide (shown below) can be proton tautomers. Proton tautomers are isomers that differ from each other only in the location of a hydrogen atom and a double bond. The hydrogen atom and double bond switch locations between a carbon atom and a heteroatom, such as for example N. Thus, when the nitrogen substituent is hydrogen, the two isomeric chemical structures may be used interchangeably.

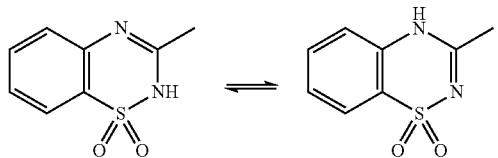

The particular $K_{ATP}$ channel openers that can be used in the invention formulations include any of those within formula I to VII. Exemplary such compounds include diazoxide, BPDZ62, BPDZ 73, NN414 and BPDZ 154 (see, for example, Schou, et al., *Bioorg. Med. Chem.*, 13, 141-155 (2005)). Compound BPDZ 154 also is an effective $K_{ATP}$ channel activator in patients with hyperinsulinism and in patients with pancreatic insulinoma. The synthesis of BPDZ compound is provided in Cosgrove, et al., *J. Clin. Endocrinol. Metab.*, 87, 4860-4868 (2002).

Analogs of diazoxide include 3-isopropylamino-7-methoxy-4H-1,2,4,-benzothiadiazine 1,1-dioxide, which is a selective Kir6.2/SUR1 channel opener (see Dabrowski, et al., *Diabetes*, 51, 1896-1906 (2002)). 2-alkyl substituted diazoxides are included (see, for example, Ouedraogo, et al., *Biol. Chem.*, 383, 1759-1768 (2002)); these channel openers show decreased activity in the inhibition of insulin release and increased activity in vascular smooth muscle tissue. Furthermore, 2-alkyl substituted diazoxides generally do not function as traditional potassium channel activators, but instead show potential as $Ca^{2+}$ blockers.

Other diazoxide analogs include described in Schou, et al., *Bioorg. Med. Chem.*, 13, 141-155 (2005), are shown below.

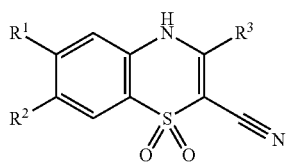

$R^1$, $R^2$ and $R^3$ are:
a) H, Cl, NHCH(CH$_3$)$_2$
b) CF$_3$, H, NHCH(CH$_3$)$_2$
c) H, Cl, NHCH$_2$CH$_2$CH(CH$_3$)$_2$
d) H, Cl, NH-cyclobutyl Diazoxide analogs having different alkyl substituents at the 3 position of the molecule (identified as R3 shown below) are described in Bertolino, et al., Receptors and Channels, 1, 267-278 (1993).

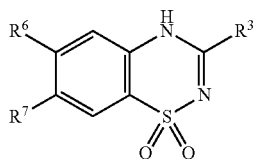

$R^3$, $R^6$ and $R^7$ are:
a) H, H, CH$_3$
b) H, H, Cl
c) CH$_3$, Cl, H
d) CH$_2$Cl, H, Cl
e) NH$_2$, H, H
f) CH$_2$CH$_2$Cl, H, Cl
g) nC$_4$H$_9$, H, Cl
h) nC$_5$H$_{11}$, H, Cl
i) nC$_7$H$_{15}$, H, Cl
j) nC$_3$H$_7$, Cl, H
k) nC$_4$H$_9$, Cl, H
l) nC$_5$H$_{11}$, Cl, H
m) nC$_7$H$_{15}$, Cl, H
n) nC$_3$H$_7$, Cl, Cl
o) nC$_4$H$_9$, Cl, Cl
p) nC$_5$H$_{11}$, Cl, Cl
q) nC$_7$H$_{15}$, Cl, Cl
r) H, Cl, H $K_{ATP}$ channel activity of formula I-VII and related compounds can be measured by membrane potential studies as described in Schou, et al., *Bioorg. Med. Chem.*, 13, 141-155 (2005) and Dabrowski, et al., *Diabetes*, 51, 1896-1906 (2002).

Measurement of the inhibition of glucose-stimulated insulin release from βTC6 cells is described in Schou, et al., *Bioorg. Med. Chem.*, 13, 141-155 (2005). The ability of particular $K_{ATP}$ channel openers to inhibit release of insulin from incubated rat pancreatic islets can be performed a described by Ouedraogo, et al., *Biol. Chem.*, 383, 1759-1768 (2002).

Activation of recombinant $K_{ATP}$ channels by $K_{ATP}$ channel openers can be examined by monitoring macroscopic currents inside-out membrane patches from *Xenopus oocytes* coexpressing Kir6.2 and either SUR1, SUR2A or SUR2B. SUR expressing membranes can be prepared by known methods. See, for example, Dabrowski, et al., *Diabetes*, 51, 1896-1906 (2002).

Binding experiments can be used to determine the ability of $K_{ATP}$ channel openers to bind SUR1, SUR2A and SUR2B. See, for example, Schwanstecher, et al., *EMBO J.*, 17, 5529-5535 (1998).

Preparation of SUR1 and SUR2A chimeras, as described by Babenko et al., allows for comparison of pharmacologic profiles (i.e. sulfonyl sensitivity and responsiveness to diazoxide or other potassium channel openers) of the SUR1/Kir6.2 and SUR2A/Kir6.2 potassium channels. See Babenko, et al., *J. Biol. Chem.*, 275(2), 717-720 (2000). The cloning of a sulfonylurea receptor and an inwardly rectifying $K^+$ channel is described by Isomoto, et al., *J. Biol. Chem.*, 271 (40), 24321-24324 (1996); D'hahan, et al., *PNAS*, 96(21), 12162-12167 (1999).

Differences between the human SUR1 and human SUR2 genes are described and shown in Aguilar-Bryan, et al., *Physiological Review*, 78(1), 227-245 (1998).

"Halo" and "halogen" refer to all halogens, that is, chloro (Cl), fluoro (F), bromo (Br), or iodo (I).

"Hydroxyl" and "hydroxy" refer to the group —OH.

"Substituted oxy" refers to the group —OR$^f$, where R$^f$ is alkyl, substituted alkyl, aryl, substituted aryl, heteroaryl, substituted heteroaryl, aralkyl, substituted aralkyl, cycloalkyl, substituted cycloalkyl, heterocyclyl, or substituted heterocyclyl.

"Substituted thiol" refers to the group —SR, where R is alkyl, substituted alkyl, acyl, substituted acyl, aryl, substituted aryl, heteroaryl, substituted heteroaryl, aralkyl, substituted aralkyl, cycloalkyl, substituted cycloalkyl, heterocyclyl, or substituted heterocyclyl.

"Alkyl" refers to an alkane-derived radical containing from 1 to 10, preferably 1 to 6, carbon atoms. Alkyl includes straight chain alkyl, branched alkyl and cycloalkyl, such as methyl, ethyl, propyl, isopropyl, butyl, t-butyl, and the like. Straight chain or branched alkyl groups contain from 1-10, preferably 1 to 6, more preferably 1-4, yet more preferably 1-2, carbon atoms. The alkyl group is attached at any available point to produce a stable compound.

A "substituted alkyl" is an alkyl group independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound. In particular, "fluro substituted" refers to substitution by 1 or more, e.g., 1, 2, or 3 fluorine atoms. "Optionally fluro substituted" means that substitution, if present, is fluoro.

"Lower alkyl" refers to an alkyl group having 1-6 carbon atoms.

A "substituted lower alkyl" is a lower alkyl which is substituted with 1 or more, e.g., 1, 2, or 3, groups or substituents as defined above, attached at any available point to produce a stable compound.

"Cycloalkyl" refers to saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like. "Cycloalkylene" is a divalent cycloalkyl.

"Alkoxy" denotes the group —OR$^f$, where R$^f$ is lower alkyl.

"Substituted alkoxy" denotes the group —OR$^f$, where R$^f$ is substituted lower alkyl.

"Alkylthio" or "thioalkoxy" refers to the group —S—R, where R is lower alkyl.

"Substituted alkylthio" or "substituted thioalkoxy" refers to the group —S—R, where R is substituted lower alkyl.

"Sulfinyl" denotes the group —S(O)—.

"Sulfonyl" denotes the group —S(O)$_2$—.

"Substituted sulfinyl" denotes the group —S(O)—R, where R is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Substituted sulfonyl" denotes the group —S(O)$_2$—R, where R is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Sulfonylamino" denotes the group —NRS(O)$_2$— where R is hydrogen or lower alkyl.

"Substituted sulfonylamino" denotes the group —NR$^a$S(O)$_2$—R$^b$, where R$^a$ is hydrogen or lower alkyl and R$^b$ is lower alkyl, substituted lower alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl or substituted aralkyl.

"Amino" or "amine" denotes the group —NH$_2$. A "divalent amine" denotes the group —NH—. A "substituted divalent amine" denotes the group —NR— wherein R is lower alkyl, substituted lower alkyl, aryl, substituted aryl, heteroaryl, substituted heteroaryl, acyl, substituted acyl, sulfonyl or substituted sulfonyl.

"Substituted amino" or "substituted amine" denotes the group —NR$^i$R$^j$, wherein R$^i$ and R$^j$ are independently hydrogen, lower alkyl, substituted lower alkyl, aryl, substituted aryl, heteroaryl, substituted heteroaryl, acyl, substituted acyl, sulfonyl, substituted sulfonyl, or cycloalkyl provided, however, that at least one of R$^i$ and R$^j$ is not hydrogen. R$^i$R$^j$ in combination with the nitrogen may form an optionally substituted heterocyclic or heteroaryl ring.

"Alkylsulfinyl" denotes the group —S(O)R$^p$, wherein R$^p$ is optionally substituted alkyl.

"Alkylsulfonyl" denotes the group —S(O)$_2$R$^p$, wherein R$^p$ is optionally substituted alkyl.

"Alkylsulfonylamino" denotes the group —NR$^q$S(O)$_2$R$^p$, wherein R$^p$ is optionally substituted alkyl, and R$^q$ is hydrogen or lower alkyl.

Pharmaceutical formulations containing K$_{ATP}$ channel openers include the free base of the drug or a salt of the drug. Such salts may have one or more of the following characteristics: (1) stablity in solution during synthesis and formulation, (2) stability in a solid state, (3) compatibility with excipients used in the manufacture of tablet formulations, (4) quantitatively yield the K$_{ATP}$ channel opener upon exposure to simulated or actual gastric and duodenal conditions, (5) release K$_{ATP}$ channel opener from sufficiently small particles that are readily dissolved and absorbed, (6) provide, when incorporated into a pharmaceutical formulation, for absorption of greater than 80% of the administered dose, (7) present no elevated toxicological risk as compared to the free base of the K$_{ATP}$ channel opener, (8) can be formulated into acceptable pharmaceutical formulations to treat obesity and other diseases of humans, (9) are acceptable to the FDA as the basis of a drug product, (10) can be recrystallized to improve purity, (11) can be used to form co-crystals of two or more salts of the K$_{ATP}$ channel opener, (12) have limited hygroscopicity to improve stability, or (13) synthetic and crystallization conditions under which the salt is formed can be varied resulting in different crystal structures (polymorphs) can be controlled in the synthesis of the salt.

K$_{ATP}$ channel openers can be formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering lower effective doses of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared, for example, by dissolving the free-base form of a compound in a suitable solvent, such as an aqueous or aqueous-alcohol in solution containing the appropriate acid and then isolated by evaporating the solution. In another example, a salt is prepared by reacting the free base and acid in an organic solvent.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Salts of $K_{ATP}$ channel openers, and particular salts of diazoxide, may include, but are not limited to acetate, acetonide, acetyl, adipate, aspartate, besylate, biacetate, bitartrate, bromide, butoxide, butyrate, calcium, camsylate, caproate, carbonate, citrate, cyprionate, decaroate, diacetate, dimegulumine, dinitrate, dipotassium, dipropionate, disodium, disulfide, edisylate, enanthate, estolate, etabonate, ethylsuccinate, fumarate, furoate, gluceptate, gluconate, hexacetonide, hippurate, hyclate, hydrobromide, hydrochloride, isethionate, lactobionate, malate, maleate, meglumine, methylbromide, methylsulfate, metrizoate, nafate, napsylate, nitrate, oleate, palmitate, pamoate, phenpropionate, phosphate, pivalate, polistirex, polygalacturonate, probutate, propionate, saccharate, sodium glycinate, sodium phosphate, podium succinate, state, succinate, sulfate, sulfonate, sulfosalicylate, tartrate, tebutate, terephalate, terephthalate, tosylate, triflutate, trihydrate, trisilicate, tromethamine, valerate, or xinafolate.

Formulations provided herein exhibit some or all the following characteristics: (1) they are stable at ambient temperatures for a minimum of one year; (2) they provide for ease of oral administration; (3) they facilitate patient compliance with dosing; (4) upon administration, they consistently facilitate high levels of absorption of the pharmaceutical active; (5) upon once or twice daily oral administration they allow release of the $K_{ATP}$ channel opener over a sustained time frame such that the circulating concentration of the $K_{ATP}$ channel opener or its metabolically active metabolites does not fall below a therapeutically effective concentration; (6) they achieve these results independent of the pH of the gastrointestinal tract of treated individuals, and (7) they delay release until gastric transit is complete or nearly complete.

Formulations designed for oral administration can be provided, for example, as capsules or tablets. Capsule or tablet formulations include a number of distinguishing components. One is a component to improve absorption of the $K_{ATP}$ channel opener. Another sustains release of the drug over more than 2 hours. A third delays substantial release of the drug until gastric transit is completed.

The formulations disclosed herein exhibit improved solubility and absorption of the $K_{ATP}$ channel opener compared to previous formulations of these drugs. These advantageous properties are achieved by any one or more of the following approaches: (1) reducing particle size of the formulation by comminution, spray drying, or other micronising techniques, (2) using a pharmaceutical salt of the $K_{ATP}$ channel opener, (3) using an ion exchange resin in the formulation, (4) using inclusion complexes, for example using a cyclodextrin, (5) compaction of the $K_{ATP}$ channel opener with a solubilizing agent including low viscosity hypromellose, low viscosity metylcellulose or similarly functioning excipient and combinations thereof, (6) associating the $K_{ATP}$ channel opener with a salt prior to formulation, (7) using a solid dispersion of the $K_{ATP}$ channel opener, (8) using a self emulsifying system, (9) adding one or more surfactants to the formulation, (10) using nanoparticles in the formulation, or (11) combinations of these approaches. Preferably, when the $K_{ATP}$ channel opener is a salt of diazoxide, the salt is not a sodium salt.

Release of $K_{ATP}$ channel opener over a sustained period of time (2-24 hours) is achieved by the use of one or more approaches including, but not limited to: (1) the use of pH sensitive polymeric coatings, (2) the use of a hydrogel, (3) the use of a film coating that controls the rate of diffusion of the drug from a coated matrix, (4) the use of an erodable matrix that controls rate of drug release, (5) the use of polymer coated pellets, granules, or microparticles which can be further encapsulated or compressed into a tablet, (6) the use of an osmotic pump system, or (7) the use of a compression coated tablet, or (8) combinations of these approaches.

Delay of release of $K_{ATP}$ channel openers from the formulation until gastric transit is complete is achieved in the formulations provided herein by any of several mechanisms. A pH sensitive polymer or co-polymer is used which when applied around the drug matrix functions as an effective barrier to release of active at pH 3.0 or lower and is unstable at pH 5.5 and above. This provides for control of release of the active compound in the stomach but rapidly allows release once the dosage form has passed into the small intestine. An alternative to a pH sensitive polymer or co-polymer is a polymer or co-polymer that is non-aqueous-soluble. The extent of resistance to release in the gastric environment can be controlled by coating with a blend of the non-aqueous-soluble and a aqueous soluble polymer. In this approach neither of the blended polymers or co-polymers are pH sensitive. One example of a pH sensitive co-polymer is the Eudragit methacrylic co-polymers, including Eudragit L100, S100 or L100-55 solids, L30 D-55 or FS 30D dispersions, or the L12.5 or S12.5 organic solutions.

Polymers that delay release can be applied to a tablet either by spray coating (as a thin film) or by compression coating. If a capsule is used, then the polymer(s) may be applied over the surface of the capsule or applied to microparticles of the drug, which may then be encapsulated such as in a capsule or gel. If the capsule is coated, then it will resist disintegration until after gastric transit. If microparticles are coated, then the capsule may disintegrate in the stomach but little to no drug will be released until after the free microparticles complete gastric transit. Finally, an osmotic pump system that uses e.g., a swellable hydrogel can be used to delay drug release in the stomach. The swellable hydrogel takes up moisture after administration. Swelling of the gel results in displacement of the drug from the system for absorption. The timing and rate of release of the drug depend on the gel used, and the rate at which moisture reaches the gel, which can be controlled by the size of the opening in the system through which fluid enters. See Drug Delivery Technologies online article Dong et al. "L-OROS® SOFTCAP™ for Controlled Release of Non-Aqueous Liquid Formulations."

Accordingly, delay of release of $K_{ATP}$ channel openers from the invention formulations until after gastric transit is complete is achieved in the formulations provided herein by any of several mechanisms, including, but not limited to: (a) a pH sensitive polymer or co-polymer applied as a compression coating on a tablet; (b) a pH sensitive polymer or co-polymer applied as a thin film on a tablet; (c) a pH sensitive polymer or co-polymer applied as a thin film to an encapsulation system; (d) a pH sensitive polymer or co-polymer applied to encapsulated microparticles, (e) a non-aqueous-soluble polymer or copolymer applied as a compression coating on a tablet; (f) a non-aqueous-soluble polymer or co-polymer applied as a thin film on a tablet; (g) a non-aqueous soluble polymer applied as a thin film to an encapsulation system; (h) a non-aqueous soluble polymer applied to microparticles; (i) incorporation of the formulation in an osmotic pump system, or (j) use of systems controlled by ion exchange resins, or (k) combinations of these approaches, wherein the pH sensitive polymeror co-polymer is resistant to degradation under acid conditions.

Formulations are provided that are designed for administration once daily (per 24 hours). These can contain between 25 and 500 mg of $K_{ATP}$ channel openers. Formulations intended for administration twice daily (per 24 hours) are also provided. These can contain between 25 and 250 mg of $K_{ATP}$ channel openers.

The formulations provided herein exhibit improved safety of the administered drug product. This improvement in safety occurs by at least two mechanisms. First, delay of release of active drug until gastric transit is complete can reduce the incidence of a range of gastrointestinal adverse side effects including nausea, vomiting, dyspepsia, abdominal pain, diarrhea and ileus. Second, by sustaining release of the active drug over 2 or more hours to as long as 24 hours, peak drug levels are reduced relative to the peak drug levels observed for the same administered dose using any oral formulation that does not have sustained or controlled release. This reduction in peak drug levels can contribute to reductions in adverse effects that are partially or completely determined by peak drug levels. These adverse effects include: fluid retention with the associated reduced rates of excretion of sodium, chloride and uric acid, edema, hyperglycemia and the associated potential for progression to ketoacidosis, cataracts and non-ketotic hyperosmolar coma, headaches, tachycardia and palpitations.

Also provided herein are controlled release formulations of $K_{ATP}$ channel openers, which have one feature from each of A-D as shown in Table 1.

TABLE 1

Controlled Release Formulation Characteristics and Properties

| | |
|---|---|
| A. Unit Form: | Tablet or Capsule |
| B. Dosage/unit: | 10-100 mg |
| | 100-200 mg |
| | 200-300 mg |
| | 300-500 mg |
| | 500-2000 mg |
| C. Dosing | Once daily (24 hours) |
| | Twice daily (24 hours) |

TABLE 1-continued

Controlled Release Formulation Characteristics and Properties

| | |
|---|---|
| D. Release time: | 2-4 hrs |
| | 4-8 hrs |
| | 8-24 hours |

For example, a controlled release composition can be a tablet containing 25-100 mg of a $K_{ATP}$ channel opener, such tablet administered once daily to achieve a controlled release time of 2-4 hours. All of these formulations can further include the feature of substantially delaying pharmaceutical active release until after gastric transit is complete.

In addition, any of the above formulations from Table 1 can include at least one feature that improves the solubility or absorption of the $K_{ATP}$ channel opener.

The controlled release formulations provided herein comprise the active compound ($K_{ATP}$ channel opener) and a matrix which comprises a gelling agent that swells upon contact with aqueous fluid. The active compound entrapped within the gel is slowly released into the body upon dissolution of the gel. The active compound can be evenly dispersed within the matrix or can be present as pockets of drug in the matrix. For example, the drug can be formulated into small granules which are dispersed within the matrix. In addition, the granules of drug also can include a matrix, thus, providing a primary and a secondary matrix as described in U.S. Pat. No. 4,880,830 to Rhodes.

The gelling agent preferably is a polymeric material, which can include, for example, any pharmaceutically acceptable water soluble or water insoluble slow releasing polymer such as xantham gum, gelatin, cellulose ethers, gum arabic, locust bean gum, guar gum, carboxyvinyl polymer, agar, acacia gum, tragacanth, veegum, sodium alginate or alginic acid, polyvinylpyrrolidone, polyvinyl alcohol, or film forming polymers such as methyl cellulose (MC), carboxymethyl cellulose (CMC), hydroxypropyl methylcellulose, hyroxypropyl methyl cellulose (HPMC), hydroxypropyl cellulose (HPC), hydroxyethyl cellulose (HEC), ethylcellulose (EC), acrylic resins or mixtures of the above (see e.g., U.S. Pat. No. 5,415,871).

The gelling agent of the matrix also can be a heterodisperse gum comprising a heteropolysaccharide component and a homopolysaccharide component which produces a fast-forming and rigid gel as described in U.S. Pat. No. 5,399,359. The matrix also can include a crossing agent such as a monovalent or multivalent metal cations to further add rigidity and decrease dissolution of the matrix, thus further slowing release of drug. The amount of crosslinking agent to add can be determined using methods routine to the ordinary skilled artisan.

The matrix of the controlled release composition also can include one or more pharmaceutically acceptable excipients recognized by those skilled in the art, i.e. formulation excipients. Such excipients include, for example, binders: polyvinylpyrrolidone, gelatin, starch paste, microcrystalline cellulose; diluents (or fillers): starch, sucrose, dextrose, lactose, fructose, xylitol, sorbitol, sodium chloride, dextrins, calcium phosphate, calcium sulphate; and lubricants: stearic acid, magnesium stearate, calcium stearate, Precirol (trade mark) and flow aids for example talc or colloidal silicon dioxide.

The matrix of the controlled release composition can further include a hydrophobic material which slows the hydration of the gelling agent without disrupting the hydrophilic nature of the matrix, as described in U.S. Pat. No.

5,399,359. The hydrophobic polymer can include, for example, alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, waxes and waxy substances such as carnauba wax, spermaceti wax, candellila wax, cocoa butter, cetosteryl alcohol, beeswax, ceresin, paraffin, myristyl alcohol, stearyl alcohol, cetylalcohol and stearic acid, and any other pharmaceutically acceptable hydrophobic material known to those skilled in the art.

The amount of hydrophobic material incorporated into the controlled release composition is that which is effective to slow the hydration of the gelling agent without disrupting the hydrophilic matrix formed upon exposure to an environmental fluid. In certain preferred embodiments, the hydrophobic material is included in the matrix in an amount from about 1 to about 20 percent by weight and replaces a corresponding amount of the formulation excipient. A solvent for the hydrophobic material may be an aqueous or organic solvent, or mixtures thereof.

Examples of commercially available alkylcelluloses are Aquacoat® (aqueous dispersion of ethylcellulose available from FMC) and Surelease® (aqueous dispersion of ethylcellulose available from Colorcon). Examples of commercially available acrylic polymers suitable for use as the hydrophobic material include Eudragit® RS and RL (copolymers of acrylic and methacrylic acid esters having a low content (e.g., 1:20 or 1:40) of quaternary ammonium compounds).

The controlled release composition also can be coated to retard access of liquids to the active compound and/or retard release of the active compound through the film-coating. The film-coating can provide characteristics of gastroresistance and enterosolubility by resisting rapid dissolution of the composition in the digestive tract. The film-coating generally represents about 5-15% by weight of the controlled release composition. Preferably, the core by weight represents about 90% of the composition with the remaining 10% provided by the coating. Such coating can be a film-coating as is well known in the art and include gels, waxes, fats, emulsifiers, combination of fats and emulsifiers, polymers, starch, and the like.

Polymers and co-polymers are useful as thin film coatings. Solution coatings and dispersion coatings can be used to coat the active compound, either alone or combined with a matrix. The coating is preferably applied to the drug or drug and matrix combination as a solid core of material as is well known in the art.

A solution for coating can include polymers in both organic solvent and aqueous solvent systems, and typically further including one or more compounds that act as a plasticizer. Polymers useful for coating compositions include, for example, methylcellulose (Methocel® A; Dow Chemical Co.), hydroxypropylmethylcellulose with a molecular weight between 1,000 and 4,000,000 (Methocel® E; Dow Chemical Co. or Pharmacoat®; Shin Etsu), hydroxypropyl cellulose with a molecular weight between 2,000 and 2,000,000, ethyl cellulose, cellulose acetate, cellulose triacetate, cellulose acetate butyrate, cellulose acetate phthalate, cellulose acetate trimellitate (Eastman Kodak), carboxymethylethyl cellulose (Duodcel®), hydroxypropyl methylcellulose phthalate, ethylcellulose, methylcellulose and, in general, cellulosic derivatives, olymethacrylic acid-methacrylic acid copolymer (Type A 1:1 Eudragit L100; Type B 1:2 Eudragit S100; and Type C 1:1 Eudragit L100-55, aqueous dispersion 30% solids, Eudragit L30D), poly (meth)acryl ester: poly(ethyl acrylate, methyl methacrylate 2:1), Eudragit NE30D aqueous dispersion 30% solids, polyaminomethacrylate Eudragit E100, poly(trimethylammonioethyl methacrylate chloride)ammoniomethacrylate copolymer, Eudragit RL30D and Eudragit RS30D, carboxyvinyl polymers, polyvinylalcohols, glucans scleroglucans, mannans, and xanthans.

Aqueous polymeric dispersions include Eudragit L30D and RS/RL30D, and NE30D, Aquacoat brand ethyl cellulose, Surelease brand ethyl cellulose, EC brand N-10F ethyl cellulose, Aquateric brand cellulose acetate phthalate, Coateric brand Poly(vinyl acetate phthalate), and Aqacoat brand hydroxypropyl methylcellulose acetate succinate. Most of these dispersions are latex, pseudolatex powder or micronized powder mediums.

A plasticizing agent may be included in the coating to improve the elasticity and the stability of the polymer film and to prevent changes in the polymer permeability over prolonged storage. Such changes may affect the drug release rate. Suitable conventional plasticizing agents include, for example, diethyl phthalate, glycerol triacetate, acetylated monoglycerides, acetyltributylcitrate, acetyltriethyl citrate, castor oil, citric acid esters, dibutyl phthalate, dibutyl sebacate, diethyloxalate, diethyl malate, diethylfumarate, diethylphthalate, diethylsuccinate, diethylmalonate, diethyltartarate, dimethylphthalate, glycerin, glycerol, glyceryl triacetate, glyceryltributyrate, mineral oil and lanolin alcohols, petrolatum and lanolin alcohols, phthalic acid esters, polyethylene glycols, propylene glycol, rape oil, sesame oil, triacetin, tributyl citrate, triethyl citrate, and triethyl acetyl citrate, or a mixture of any two or more of the foregoing. Plasticizers which can be used for aqueous coatings include, for example, propylene glycol, polyethylene glycol (PEG 400), triacetin, polysorbate 80, triethyl citrate, and diethyl d-tartrate.

A coating solution comprising a mixture of hydroxypropylmethylcellulose and aqueous ethylcellulose (e.g. Aquacoat brand) as the polymer and dibutyl sebacate as plasticizer can be used for coating microparticles. (Aquacoat is an aqueous polymeric dispersion of ethylcellulose and contains sodium lauryl sulfate and cetyl alcohol). Preferably, the plasticizer represents about 1-2% of the composition.

In addition to the polymers, the coating layer can include an excipient to assist in formulation of the coating solution. Such excipients may include a lubricant or a wetting agent. Suitable lubricants as excipients for the film coating include, for example, talc, calcium stearate, colloidal silicon dioxide, glycerin, magnesium stearate, mineral oil, polyethylene glycol, and zinc stearate, aluminum stearate or a mixture of any two or more of the foregoing. Suitable wetting agents include, for example, sodium lauryl sulfate, acacia, benzalkonium chloride, cetomacrogol emulsifying wax, cetostearyl alcohol, cetyl alcohol, cholesterol, diethanolamine, docusate sodium, sodium stearate, emulsifying wax, glyceryl monostearate, hydroxypropyl cellulose, lanolin alcohols, lecithin, mineral oil, onoethanolamine, poloxamer, polyoxyethylene alkyl ethers, polyoxyethylene castor oil derivatives, polyoxyethylene sorbitan fatty acid esters, polyoxyethylene stearates, propylene glycol alginate, sorbitan esters, stearyl alcohol and triethanolamine, or a mixture of any two or more of the foregoing.

The specified tablet or capsule formulations of Table 1 may include co-formulation with an obesity treating drug (in addition to the $K_{ATP}$ channel opener). Obesity treating drugs that may be used include, but are not limited to, sibutramine hydrochloride (5-30 mg/unit), orlistat (50-360 mg/unit), phentermine hydrochloride or resin complex (15 to 40 mg/unit), zonisamide (100 to 600 mg/unit) topiramate (64 to 400 mg/unit), naltrexone hydrochloride (50 to 600 mg/unit), rimonabant (5 to 20 mg/unit), ADP356 (5 to 25 mg/unit), ATL962 (20 to 400 mg/unit), or AOD9604 (1 to 10 mg/unit). These formulations are preferably used once daily. For a twice daily dosing, the amount of $K_{ATP}$ channel opener is one half the amount included in the once daily formulation and the coformulated obesity treating drug is half of the amount specified. Alternative obesity treating drugs may include: selective serotonin 2c receptor agonists, dopamine antagonists, cannabinoid-1 receptor antagonists, leptin analogues, leptin transport and/or leptin receptor promoters, neuropeptide Y and agouti-related peptide antagonists, proopiomelanocortin and cocaine and amphetamine regulated transcript promoters, melanocyte-stimulating hormone analogues, melanocortin-4 receptor agonists, and agents that affect insulin metabolism/activity, which include protein-tyrosine phosphatase-1B inhibitors, peroxisome proliferator activated receptor-receptor antagonists, short-acting bromocriptine (ergoset), somatostatin agonists (octreotide), and adiponectin, gastrointestinal-neural pathway agents, including those that increase cholecystokinin activity, increase glucagon-like peptide-1 activity (extendin 4, liraglutide, dipeptidyl peptidase IV inhibitors), and increase protein YY3-36 activity and those that decrease ghrelin activity, as well as amylin analogues, agents that may increase resting metabolic rate ("selective" β-3 stimulators/agonist, uncoupling protein homologues, and thyroid receptor agonists), melanin concentrating hormone antagonists, phytostanol analogues, amylase inhibitors, growth hormone fragments, synthetic analogues of dehydroepiandrosterone sulfate, antagonists of adipocyte 11Bhydroxysteroid dehydrogenase type 1 activity, corticotropin releasing hormone agonists, inhibitors of fatty acid synthesis, carboxypeptidase inhibitors, indanones/indanols, aminosterols, and other gastrointestinal lipase inhibitors.

The specified tablet or capsule formulations of Table 1 may include co-formulation with a diabetes treating drug (in addition to the $K_{ATP}$ channel opener). Diabetes treating drugs that may be used include, but are not limited to acarbose (50 to 300 mg/unit), miglitol (25 to 300 mg/unit), metformin hydrochloride (300 to 2000 mg/unit), repaglinide (1-16 mg/unit), nateglinide (200 to 400 mg/unit), rosiglitizone (5 to 50 mg/unit), metaglidasen (100 to 400 mg/unit) or any drug that improves insulin sensitivity, or improves glucose utilization and uptake. These formulations are preferably used once daily. For a twice daily dosing, the amount of the $K_{ATP}$ channel opener is half the amount included in the once daily formulation and the co-formulated diabetes treating drug is half of the amount specified.

The specified tablet or capsule formulations of Table 1 may include co-formulation with a cholesterol lowering drug. Cholesterol lowering drugs that may be used include, but are not limited to pravastatin or simvastatin or atorvastatin or fluvastatin or rosuvastatin or lovastatin (all at 10 to 80 mg/unit). These formulations are preferably used once daily. For a twice daily dosing, the amount of $K_{ATP}$ channel opener is preferably 25 to 200 mg/unit and the coformulated cholesterol lowering drug is half of the amount specified.

The specified tablet or capsule formulations of Table 1 may include co-formulation with a depression treating drug. Depression treating drugs that may be used include, but are not limited to citalopram hydrobromide (10 to 80 mg/unit), escitalopram hydrobromide (5 to 40 mg/unit), fluvoxamine maleate (25 to 300 mg/unit), paroxetine hydrochloride (12.5 to 75 mg/unit), fluoxetine hydrochloride (30 to 100 mg/unit), setraline hydrochloride (25 to 200 mg/unit), amitriptyline hydrochloride (10 to 200 mg/unit), desipramine hydrochloride (10 to 300 mg/unit), nortriptyline hydrochloride (10 to 150 mg/unit), duloxetine hydrochloride (20 to 210 mg/unit), venlafaxine hydrochloride (37.5 to 150 mg/unit), phenelzine sulfate (10 to 30 mg/unit), bupropion hydrochloride (200 to 400 mg/unit), or mirtazapine (7.5 to 90 mg/unit). These formulations are preferably used once daily. For a twice daily dosing, the amount of $K_{ATP}$ channel opener is preferably half the amount included in the once daily formulation and the coformulated depression treating drug is half of the amount specified.

The specified tablet or capsule formulations of Table 1 may include co-formulation with a hypertension treating drug. Hypertension treating drugs that may be used include, but are not limited to enalapril maleate (2.5 to 40 mg/unit), captopril (2.5 to 150 mg/unit), lisinopril (10 to 40 mg/unit), benzaepril hydrochloride (10 to 80 mg/unit), quinapril hydrochloride (10 to 80 mg/unit), peridopril erbumine (4 to 8 mg/unit), ramipril (1.25 to 20 mg/unit), trandolapril (1 to 8 mg/unit), fosinopril sodium (10 to 80 mg/unit), moexipril hydrochloride (5 to 20 mg/unit), losartan potassium (25 to 200 mg/unit), irbesartan (75 to 600 mg/unit), valsartan (40 to 600 mg/unit), candesartan cilexetil (4 to 64 mg/unit), olmesartan medoxamil (5 to 80 mg/unit), telmisartan (20 to 160 mg/unit), eprosartan mesylate (75 to 600 mg/unit), atenolol (25 to 200 mg/unit), propranolol hydrochloride (10 to 180 mg/unit), metoprolol tartrate, succinate or fumarate (all at 25 to 400 mg/unit), nadolol (20 to 160 mg/unit), betaxolol hydrochloride (10 to 40 mg/unit), acebutolol hydrochloride (200 to 800 mg/unit), pindolol (5 to 20 mg/unit), bisoprolol fumarate (5 to 20 mg/unit), nifedipine (15 to 100 mg/unit), felodipine (2.5 to 20 mg/unit), amlodipine besylate (2.5 to 20 mg/unit), nicardipine (10 to 40 mg/unit), nisoldipine (10 to 80 mg/unit), terazosin hydrochloride (1 to 20 mg/unit), doxasoxin mesylate (4 to 16 mg/unit), prazosin hydrochloride (2.5 to 10 mg/unit), or alfuzosin hydrochloride (10 to 20 mg/unit). These formulations are preferably used once daily. For a twice daily dosing, the amount of $K_{ATP}$ channel opener is preferably half the amount included in the once daily formulation and the coformulated hypertension treating drug is half of the amount specified.

The specified tablet or capsule formulations of Table 1 may include co-formulation with a diuretic to treat edema. Diuretics that may be used include, but are not limited to amiloride hydrochloride (1 to 10 mg/unit), spironolactone (10 to 100 mg/unit), triamterene (25 to 200 mg/unit), bumetanide (0.5 to 4 mg/unit), furosemide (10 to 160 mg/unit), ethacrynic acid or ethacrynate sodium (all at 10 to 50 mg/unit), tosemide (5 to 100 mg/unit), chlorthalidone (10 to 200 mg/unit), indapamide (1 to 5 mg/unit), hydrochlorothiazide (10 to 100 mg/unit), chlorothiazide (50 to 500 mg/unit), bendroflumethiazide (5 to 25 mg/unit), hydroflumethiazide (10 to 50 mg/unit), mythyclothiazide (1 to 5 mg/unit), or polythiazide (1 to 10 mg/unit). These formulations are preferably used once daily. For a twice daily dosing, the amount of $K_{ATP}$ channel opener is preferably half the amount included in the once daily formulation and the coformulated diuretic is half of the amount specified.

The specified tablet or capsule formulations of Table 1 may include co-formulation with a drug to treat inflammation or pain. Drugs for treating inflammation or pain that may be used include, but are not limited to aspirin (100 to 1000 mg/unit), tramadol hydrochloride (25 to 150 mg/unit), gabapentin (100 to 800 mg/unit), acetominophen (100 to 1000 mg/unit), carbamazepine (100 to 400 mg/unit), ibuprofen (100 to 1600 mg/unit), ketoprofen (12 to 200 mg/unit), fenprofen sodium (100 to 600 mg/unit), flurbiprofen sodium or flurbiprofen (both at 50 to 200 mg/unit), or combinations of any of these with a steroid or aspirin. These formulations are preferably used once daily. For a twice daily dosing, the amount of $K_{ATP}$ channel opener is preferably half the amount included in the once daily formulation and the coformulated diuretic is half of the amount specified.

The specified tablet or capsule formulations of Table 1 may include co-formulation with a drug to treat obesity associated comorbidities include those specified above for treating diabetes, cholesterol, depression, hypertension and edema, or drugs to treat atherosclerosis, osteoarthritis, disc herniation, degeneration of knees and hips, breast, endometrial, cervical, colon, leukemia and prostate cancers, hyperlipidemia, asthma/reactive airway disease, gallstones, GERD, obstructive sleep apnea, obesity hypoventilation syndrome, recurrent ventral hernias, menstrual irregularity and infertility.

The specified tablet or capsule formulations of Table 1 may include co-formulation with an anti-psychotic drug the combination used to treat the psychotic condition and to treat or prevent weight gain, dyslipidemia or impaired glucose tolerance in the treated individual. Drugs for treating various psychotic conditions that may be used include, but are not limited to, lithium or a salt thereof (250 to 2500 mg/unit), carbamazepine or a salt thereof (50 to 1200 mg/unit), valproate, valproic acid, or divalproex (125 to 2500 mg/unit), lamotrigine (12.5 to 200 mg/unit), olanzapine (5 to 20 mg/unit), clozapine (12.5 to 450 mg/unit), or risperidone (0.25 to 4 mg/unit). These coformulations are preferably intended for once per day administration. For a twice daily dosing, the amount of $K_{ATP}$ channel opener is preferably half the amount included in the once daily formulation and the coformulated anti-psychotic is half of the amount specified.

The specified tablet or capsule formulations of Table 1 may include co-formulation with a drug to treat or prevent ischemic or reperfusion injury. Drugs for treating or preventing ischemic or reperfusion injury that may be used include, but are not limited to: low molecular weight heparins (dalteparin, enoxaparin, nadroparin, tinzaparin or danaparoid), ancrd, pentoxifylline, nimodipine, flunarizine, ebselen, tirilazad, clomethiazole, an AMPA agonist (GYKI 52466, NBQX, YM90K, zonampanel, orMPQX), SYM 2081, selfotel, Cerestat, CP-101,606, dextrophan, dextromethorphan, MK-801, NPS 1502, remacemide, ACEA 1021, GV150526, eliprodil ifenprodil, lubeluzole, naloxone, nalfemene citicoline, acetyl-1-carnitine, nifedipine, resveratrol, a nitrone derivative, clopidogrel, dabigatram, prasugrel, troxoprodil, AGY-94806, or KAI-9803.

Provided are formulations administered once or twice daily to an obese or overweight subject continuously result in a circulating concentration of $K_{ATP}$ channel opener sufficient to induce weight loss. Weight loss occurs by the preferential loss of body fat. Additional weight loss can occur when the formulation is administered in combination with a reduced calorie diet.

Provided are formulations of $K_{ATP}$ channel openers administered as a single dose to an obese, overweight or obesity-prone subject that result in the inhibition of fasting or glucose stimulated insulin secretion for about 24 hours or for about 18 hours.

Provided are formulations of $K_{ATP}$ channel openers administered as a single dose to an obese, overweight or obesity-prone subject that result in the elevation of energy expenditure for about 24 hours or for about 18 hours.

Provided are formulations of $K_{ATP}$ channel openers administered as a single dose to an obese, overweight or obesity-prone subject that result in the elevation of beta oxidation of fat for about 24 hours or for about 18 hours.

Provided are formulations of $K_{ATP}$ channel openers administered as a single dose to an obese, overweight or obesity-prone hyperphagic subject that result in the inhibition of hyperphagia for about 24 hours or for about 18 hours.

Provided are formulations administered once or twice daily (per 24 hours) to a subject continuously result in a circulating concentration of $K_{ATP}$ channel opener sufficient to induce either beta-cell rest or improved insulin sensitivity or both. Such beta-cell rest and improvements in insulin sensitivity can contribute to effective treatment of type I diabetes, type II diabetes and prediabetes. Such beta-cell rest and improvements in insulin sensitivity can contribute to effective restoration of normal glucose tolerance in type II diabetic and prediabetic subjects.

The various pharmaceutical $K_{ATP}$ channel opener formulations have a variety of applications, including, but not limited to: (1) treatment of obesity; (2) prevention of weight gain in individuals who are predisposed to obesity; (3) treatment of hyperinsulemia or hyperinsulinism; (4) treatment of hypoglycemia; (5) treatment of hyperlipidemia, (6) treatment of type II diabetes, (7) preservation of pancreatic function in type I diabetics; (8) treatment of metabolic syndrome (or syndrome X); (9) prevention of the transition from prediabetes to diabetes, (10) correction of the defects in insulin secretion and insulin sensitivity contributing to prediabetes and type II diabetes, (11) treatment of polycystic ovary syndrome, (12) prevention of ischemic or reperfusion injury, (13) treat weight gain, dyslipidemia, or impairment of glucose tolerance in subjects treated with antipsychotics drugs, (14) prevent weight gain, dyslipidemia, or impairment of glucose tolerance in subjects treated with antipsychotics drugs and (15) treatment of any disease where hyperlipidemia, hyperinsulemia, hyperinsulinism, hyperlipidemia, hyperphagia or obesity are contributing factors to the severity or progression of the disease, including but not limited to, Prader Willi Syndrome, Froelich's syndrome, Cohen syndrome, Summit Syndrome, Alstrom, Syndrome, Borjesen Syndrome, Bardet-Biedl Syndrome, or hyperlipoproteinemia type I, II, III, and IV.

In one embodiment, a $K_{ATP}$ channel opener is administered to an overweight or obese individual as a solid oral dosage once per 24 hours to induce weight loss. In further embodiments, the individual (a) is not a type I diabetic, (b) is not a type II diabetic, (c) is not experiencing chronic, recurrent or drug-induced hypoglycemia, (d) does not have metabolic syndrome, or (e) is not experiencing malignant hypertension.

In one embodiment, a $K_{ATP}$ channel opener is administered to an overweight or obese individual as a solid oral dosage twice per 24 hours to induce weight loss. This treatment can be the sole treatment to induce weight loss. In further embodiments, the overweight or obese individual (a) does not have an insulin secreting tumor, (b) is not suffering from Poly Cystic Ovary Syndrome, (c) is not a type I diabetic, (d) is not a type II diabetic, (e) does not have metabolic syndrome, (f) is not experiencing chronic recurrent or drug-induced hypoglycemia, (g) has not been treated for schizophrenia with haloperidol, or (h) is not experiencing malignant hypertension. In further embodiments, the overweight or obese adolescent (a) has not been diagnosed as being type I or type II diabetic, (b) is not experiencing chronic, recurrent or drug-induced hypoglycemia, or (c) has not been diagnosed as having metabolic syndrome.

In another embodiment, a $K_{ATP}$ channel opener is administered to an overweight or obese individual as a solid oral dosage form three times per 24 hours to induce weight loss. This treatment can be the sole treatment to induce weight loss. In further embodiments, the overweight or obese individual (a) does not have an insulin-secreting tumor, (b) is not suffering from Poly Cystic Ovary Syndrome, (c) is not a type I diabetic, (d) is not a type II diabetic, (e) does not have metabolic syndrome, or (f) is not experiencing chronic, recurrent or drug-induced hypoglycemia.

In another embodiment, a $K_{ATP}$ channel opener is administered to an overweight or obese adolescent as a solid oral dosage form three times per 24 hours to induce weight loss. This treatment can be the sole treatment to induce weight loss. In further embodiments, the overweight or obese adolescent is (a) is a type I or type II diabetic, (b) is not experiencing chronic, recurrent or drug-induced hypoglycemia or (c) does not have metabolic syndrome.

In another embodiment, a $K_{ATP}$ channel opener is administered as a solid oral dosage form three times per 24 hours to induce weight loss to an overweight or obese adult who (a) is not simultaneously receiving glucagon injections, triiodothyroxin or furosemide, (b) is not being treated for schizophrenia with haloperidol, or (c) is not experiencing malignant hypertension.

In another embodiment, a $K_{ATP}$ channel opener is administered to an overweight or obese individual as a solid oral dosage form four times per 24 hours to induce weight loss.

In another embodiment, a $K_{ATP}$ channel opener is administered to an overweight or obese individual as a solid oral dosage form administered from one, two, three or four times per 24 hours to induce weight loss at a daily dose of 50 to 275 mg. In a further embodiment, the overweight or obese individual individual (a) is not type I diabetic, (b) is not type II diabetic, (c) is not suffering chronic, recurrent or drug-induced hypoglycemia, or (d) does not have metabolic syndrome.

In another embodiment, a $K_{ATP}$ channel opener is administered to an overweight or obese individual as a solid oral dosage form administered from one, two, three or four times per 24 hours to induce weight loss at a daily dose of 130 to 275 mg. In a further embodiment, the overweight or obese individual (a) is not type I diabetic, (b) is not type II diabetic, (c) is not suffering chronic, recurrent or drug-induced hypoglycemia, or (d) does not have metabolic syndrome.

In other embodiment, a $K_{ATP}$ channel opener is administered to an overweight or obesity prone individual as a solid oral dosage form one, two, three or four times per 24 hours to maintain a weight loss, as it is preferable to maintain weight in an obese individual once some weight loss has occurred when the alternative is to regain weight. In a further embodiment, the administered daily dose of the $K_{ATP}$ channel opener is 50 to 275 mg.

In other embodiments, a $K_{ATP}$ channel opener is administered as a solid oral dosage form to an overweight, obese, or obesity prone individual to (a) elevate energy expenditure, (b) elevate beta oxidation of fat, or (c) reduce circulating triglyceride concentrations.

In other embodiments, a solid oral dosage of a $K_{ATP}$ channel opener is administered on a prolonged basis to an individual in need thereof to induce the loss of 25%, 50%, or 75% of initial body fat.

In another embodiment, a solid oral dosage of a $K_{ATP}$ channel opener is administered on a prolonged basis to an individual in need thereof to induce (a) the preferential loss of body fat or (b) the preferential loss of visceral body fat.

In additional embodiments, a solid oral dosage of a $K_{ATP}$ channel opener is administered on a prolonged basis one, two or three times per 24 hours at daily doses of 50 to 275 mg to an individual to (a) induce the loss of 25%, 50% or 75% of initial body fat, (b) induce the preferential loss of body fat, or (c) induce the preferential loss of visceral fat.

In another embodiment, a solid oral dosage of a $K_{ATP}$ channel opener is administered to an individual to induce the preferential loss of body fat and to induce reduction in circulating triglycerides.

In another embodiment, a solid oral dosage of a $K_{ATP}$ channel opener is co-administered with sibutramine, orlistat, rimonabant, an appetite suppressant, an anti-depressant, an anti-epileptic, a diuretic that is not furosemide, a drug that induces weight loss by a mechanism that is distinct from a $K_{ATP}$ channel opener, a drug that induces weight loss by a mechanism that is distinct from a $K_{ATP}$ channel opener but is not metformin, furosemide or triiodothyroxin, or a drug that lowers blood pressure, to induce weight loss and/or treat obesity associated comorbidities in an overweight, obese, or obesity prone individual. In further embodiments, the overweight, obese, or obesity prone individual (a) is a type I diabetic, (b) is not a type II diabetic, (c) is not suffering from chronic, recurrent or drug-induced hypoglycemia, or (d) does not have metabolic syndrome.

In another embodiment a solid oral dosage of a $K_{ATP}$ channel opener is co-administered with an anti-depressant, a drug that lowers blood pressure, a drug that lowers cholesterol, a drug that raises HDL, an anti-inflammatory that is not a Cox-2 inhibitor, a drug that lowers circulating triglycerides, to an overweight, obese, or obesity prone individual to induce weight loss and/or treat obesity associated comorbidities. In further embodiments, the overweight, obese, or obesity prone individual (a) is not a type I diabetic, (b) is not a type II diabetic, (c) is not suffering from chronic, recurrent or drug-induced hypoglycemia, or (d) does not have metabolic syndrome.

In another embodiment, a solid oral dosage of a $K_{ATP}$ channel opener is co-administered with a drug that lowers blood pressure, a drug that lowers cholesterol, a drug that raises HDL, an anti-inflammatory that is not a Cox-2 inhibitor, a drug that lowers circulating triglycerides, to maintain weight and/or treat obesity associated comorbidities in an overweight, obese, or obesity prone individual, as it is preferable to maintain weight in an obese individual once some weight loss has occurred when the alternative is to regain weight. In further embodiments, the overweight, obese, or obesity prone individual (a) is not a type I diabetic, (b) is not a type II diabetic, (c) is not suffering from chronic, recurrent or drug-induced hypoglycemia, or (d) does not have metabolic syndrome.

In additional embodiments, a tablet formulation of a $K_{ATP}$ channel opener is used to administer a therapeutically effective dose of a $K_{ATP}$ channel opener to an obese, overweight or obesity prone individual in need thereof to treat obesity, to (a) provide beta cell rest, (b) treat type I or type II diabetes, or (c) prevent the occurrence of diabetes.

In additional embodiments, a solid oral dosage form or tablet formulation of a $K_{ATP}$ channel opener is co-administered with Phentermine or a derivative thereof to an obese adult or adolescent to induce weight loss and/or treat obesity and obesity-associated co-morbidities. In further embodiments, a solid oral dosage form or tablet formulation of a $K_{ATP}$ channel opener is co-administered with Phentermine or a derivative thereof to an obese adult or adolescent to treat metabolic syndrome in a patient in need thereof.

In further embodiments, a pharmaceutically acceptable formulation of a $K_{ATP}$ channel opener at doses of 50 to 275 mg/day is co-administered with Phentermine or a derivative thereof at daily doses of 15 to 37.5 mg to an overweight or obese individual to induce weight loss, to treat metabolic syndrome, or to induce weight loss and treat obesity-associated co-morbidities. In another embodiment, a tablet formulation is co-administered with Phentermine or a derivative thereof to treat metabolic syndrome in a patient.

In another embodiment, a quick dissolving formulation of a $K_{ATP}$ channel opener is used to provide a therapeutically effective dose to a patient in need thereof.

In further embodiments, a $K_{ATP}$ channel opener is administered once per 24 hours at doses of 125 mg to 275 mg to an overweight or obese individual who is not type II diabetic and is not being treated for nighttime hypoglycemia.

In further embodiments, a $K_{ATP}$ channel opener is formulated as a tablet or capsule for oral administration. The tablet or capsule may be co-formulated with metformin. In another embodiment, a $K_{ATP}$ channel opener is formulated as an oral suspension, and the oral suspension may be further encapsulated in another embodiment.

In another embodiment, a pharmaceutical salt of a $K_{ATP}$ channel opener is formulated as a tablet or capsule for oral administration, or as an oral suspension or as an oral solution, or as an oral solution that is encapsulated. If the opener is diazoxide, the salt, is preferably not a sodium salt.

In another embodiment a $K_{ATP}$ channel opener is co-formulated with hydrochlorothiazide, chlorothiazide, cyclothiazide, benzthiazide, metyclothiazide, bendroflumethiazide, hydroflumethiazide, trichlormethiazide, or polythiazide in a pharmaceutical formulation suitable for oral administration.

Upon administration of the formulations provided herein to humans or animals, some or all of the following effects are observed: (1) the production of lipoprotein lipase by adipocytes is reduced; (2) enhanced lipolysis by adipocytes; (3) expression of fatty acid synthase by adipocytes is reduced; (4) glyceraldehydes phosphate dehydrogenase activity of adipocytes is reduced; (5) little or no new triglycerides are synthesized and stored by adipocytes; (6) enhanced expression of $\beta_3$ Adrenergic Receptor ($\beta_3$AR) an improvement in the adrenergic function in adipocytes; (7) reduced glucose stimulated secretion of insulin by pancreatic B-cells; (8) decreased insulinemia; (9) enhanced blood glucose levels; (10) increased expression of Uncoupling Protein 1 in adipocytes; (11) enhanced thermogenesis in white and brown adipose tissue; (12) reduction of plasma triglyceride concentration; (13) decrease in circulating leptin concentrations; (14) up-regulation of insulin receptors; (15) enhanced glucose uptake; (16) reduced adipocyte hyperplasia; (17) reduced adipocyte hypertrophy; (18) reduced rates of conversion of preadipocytes to adipocytes; (19) reduced rates of hyperphagia, (20) increased protection of CNS, cardiac and other tissues from ischemic or reperfusion injury, (21) improved insulin sensitivity, (22) elevated CSF insulin concentrations, (23) elevated circulating adiponectin concentrations, (25) reduced circulating triglyceride concentrations, (26) enhancement of beta-cell rest.

Threshold concentrations of the current invention include those circulating concentrations of $K_{ATP}$ channel openers resulting from the administration of the drug as an i.v. formulation, an immediate release oral formulation, a controlled release formulation, a transdermal formulation, or an intranasal formulation to an overweight or obese individual which results in (1) measurable suppression of fasting insulin levels, (2) suppression of fasting insulin levels by at least 20% from the baseline measurement in the same individual prior to treatment with a $K_{ATP}$ channel openers, (3) suppression of fasting insulin levels by at least 30% from the baseline measurement in the same individual prior to treatment with a $K_{ATP}$ channel openers, (4) suppression of fasting insulin levels by at least 40% from the baseline measurement in the same individual prior to treatment with a $K_{ATP}$ channel openers, (5) suppression of fasting insulin levels by at least 50% from the baseline measurement in the same individual prior to treatment with a $K_{ATP}$ channel openers, (6) suppression of fasting insulin levels by at least 60% from the baseline measurement in the same individual prior to treatment with a $K_{ATP}$ channel openers, (7) suppression of fasting insulin levels by at least 70% from the baseline measurement in the same individual prior to treatment with a $K_{ATP}$ channel openers, (8) suppression of fasting insulin levels by at least 80% from the baseline measurement in the same individual prior to treatment with a $K_{ATP}$ channel openers, (9) loss of weight, (10) elevation of resting energy expenditure, or (11) elevation of the oxidation of fat or fatty acids. Threshold effects of the current invention include those circulating concentrations of $K_{ATP}$ channel openers resulting from the administration of an i.v. formulation of the drug, or an immediate release oral formulation of the drug, or a controlled release formulation of the drug, or a sustained release formulation, or a transdermal formulation, or an intranasal formulation of the drug to an obesity prone individual which result in (1) the loss of weight, and (2) the maintenance of weight. Threshold effects of the current invention include those circulating concentrations of $K_{ATP}$ channel openers resulting from the administration of an i.v. formulation of the drug, or an immediate release oral formulation of the drug, or a controlled release formulation of the drug, or a sustained release formulation, or a transdermal formulation, or an intranasal formulation of the drug to a prediabetic individual which result in prevention of the transition to diabetes. Threshold effects of the current invention include those circulating concentrations of $K_{ATP}$ channel openers resulting from the administration of an i.v. formulation of the drug, or an immediate release oral formulation of the drug, or a controlled release formulation of the drug, or a sustained release formulation, or a transdermal formulation, or an intranasal formulation of the drug to a individual with type 1 diabetes which result in beta cell rest.

The mode of action by which weight is maintained or lost resulting from the prolonged administration of $K_{ATP}$ channel openers to overweight, obese or obesity prone individuals as provided herein includes, but is not limited to one or more of (1) enhanced energy expenditure, (2) enhanced oxidation of fat and fatty acids, (3) the enhancement of lipolysis in adipose tissue, (4) enhanced glucose uptake by tissues, enhanced insulin sensitivity, and (5) improved beta adrenergic response. The mode of action by which weight is maintained or lost resulting from the prolonged administration of $K_{ATP}$ channel openers to obese or obesity prone individuals as provided herein may also include the suppression of appetite.

Prolonged administration of pharmaceutical formulations of $K_{ATP}$ channel openers to overweight or obese humans or animals results in substantial and sustained weight loss including some or all of the following effects: (1) preferential loss of body fat; (2) loss of greater than 25% of initial body fat mass; (3) loss of greater than 50% of initial body fat mass; (4) loss of greater than 75% of initial body fat mass; (5) significant increase in resting energy expenditure; (6) increase in the oxidation of fat and fatty acids; (7) reduction in blood pressure; (8) production of lipoprotein lipase by adipocytes is reduced; (9) enhanced lipolysis by adipocytes; (10) expression of fatty acid synthase by adipocytes is reduced; (11) glyceraldehydes phosphate dehydrogenase activity of adipocytes is reduced; (12) little or no new triglycerides are synthesized and stored by adipocytes; (13) enhanced expression of $\beta_3$ Adrenergic Receptor ($\beta_3$AR) and an improvement in the adrenergic function in adipocytes; (14) reduced glucose stimulated secretion of insulin by pancreatic B-cells; (15) decreased insulinemia; (16) enhanced blood glucose levels; (17) increased expression of Uncoupling Protein 1 in adipocytes; (18) enhanced thermogenesis in white and brown adipose tissue; (19) reduction of plasma triglyceride concentration; (20) decrease in circulating leptin concentrations; (21) up-regulation of insulin receptors; (22) enhanced glucose uptake; (23) reduced adipocyte hyperplasia; (24) reduced adipocyte hypertrophy; (25) reduced rates of conversion of preadipocytes to adipocytes; (26) reduced rates of hyperphagia; (27) the sequential loss first of the metabolically most active adipose tissue (visceral), followed by the loss of less metabolically active adipose tissue, (28) elevation of circulating adiponectin concentrations, (29) elevation of cerebrospinal fluid insulin levels, (30) enhanced islet insulin mRNA and insulin content, or (31) enhanced metabolic efficiency of insulin.

Prolonged administration of formulations of $K_{ATP}$ channel openers to obesity prone humans or animals, including individuals who have undergone various types of bariatric surgery, results in sustained maintenance of weight including some or all of the following effects: (1) increased resting energy expenditure; (2) increase in the oxidation of fat and fatty acids; (3) reduction in blood pressure; (4) production of lipoprotein lipase by adipocytes is reduced; (5) enhanced lipolysis by adipocytes; (6) expression of fatty acid synthase by adipocytes is reduced; (7) glyceraldehyde phosphate dehydrogenase activity of adipocytes is reduced; (8) little or no new triglycerides are synthesized and stored by adipocytes; (9) enhanced expression of $\beta_3$ Adrenergic Receptor ($\beta_3$AR) and improvement in the adrenergic function in adipocytes; (10) reduced glucose stimulated secretion of insulin by pancreatic B-cells; (11) decreased insulinemia; (12) enhanced blood glucose levels; (13) increased expression of Uncoupling Protein 1 in adipocytes; (14) enhanced thermogenesis in white and brown adipose tissue; (15) reduction of plasma triglyceride concentration; (16) decreased circulating leptin concentration; (17) up-regulation of insulin receptors; (18) enhanced glucose uptake; (19) reduced adipocyte hyperplasia; (20) reduced adipocyte hypertrophy; (21) reduced rates of conversion of preadipocytes to adipocytes; and (22) reduced rates of hyperphagia, (23) elevated circulating adiponectin concentration, (24) elevated cerebrospinal fluid insulin levels, (25) enhanced islet insulin mRNA and insulin content, or (26) enhanced metabolic efficiency of insulin.

Immediate or prolonged administration of formulations of $K_{ATP}$ channel openers to prediabetic or type I diabetic humans or animals results in the prevention of beta cell failure, improved glycemic control, and prevention of the transition from prediabetes to diabetes including some or all of the following effects: (1) increase in resting energy expenditure; (2) increase in the oxidation of fat and fatty acids; (3) reduction in blood pressure; (4) production of lipoprotein lipase by adipocytes is reduced; (5) enhanced lipolysis by adipocytes; (6) expression of fatty acid synthase by adipocytes is reduced; (7) glyceraldehyde phosphate dehydrogenase activity of adipocytes is reduced; (8) little or no new triglycerides are synthesized and stored by adipocytes; (9) enhanced expression of $\beta_3$ Adrenergic Receptor ($\beta_3$AR) and an improvement in the adrenergic function in adipocytes; (10) reduced glucose stimulated secretion of insulin by pancreatic B-cells; (11) decreased insulinemia; (12) enhanced blood glucose levels; (13) increased expression of Uncoupling Protein 1 in adipocytes; (14) enhanced thermogenesis in white and brown adipose tissue; (15) reduction of plasma triglyceride concentration; (16) decreased circulating leptin concentrations; (17) up-regulation of insulin receptors; (18) enhanced glucose uptake; (19) reduced adipocyte hyperplasia; (20) reduced adipocyte hypertrophy; (21) reduced rates of conversion of preadipocytes to adipocytes; (22) reduced rates of hyperphagia, (23) elevated circulating adiponectin concentrations, (24) elevated cerebrospinal fluid insulin levels, (25) enhanced islet insulin mRNA and insulin content, or (26) enhanced metabolic efficiency of insulin.

Immediate or prolonged administration of formulations of $K_{ATP}$ channel openers to humans or animals that are at risk for myocardial infarct, or stroke or undergoing surgical procedure that restores blood flow to heart or brain results in improved therapeutic outcomes post-surgically, or following the occurrence of myocardial infarct or stroke by improving the survival of tissue after blood flow is restored, reduced stunning of tissue, and altering the nature of the inflammatory responses.

Pharmaceutical formulations as provided herein are designed to be used in the treatment of obesity, hyperlipidemia, hypertension, weight maintenance, type I diabetes, prediabetes, type II diabetes, or any condition where weight loss, reduction in circulating triglycerides or beta cell rest contributes to therapeutic outcomes provide for a range of critical changes in pharmacodynamic and pharmacokinetic responses to administered doses of $K_{ATP}$ channel openers which changes include one or more of the following: (1) extending the pharmacodynamic effect of an administered dose to greater than 24 hours as measured by the suppression of insulin secretion, (2) providing for substantial uptake of the active pharmaceutical ingredient in the small intestine, (3) providing for substantial uptake of the active pharmaceutical ingredient in the large intestine, (4) result in lowered Cmax versus current oral suspension or capsule products for the same administered dose of active pharmaceutical ingredient, (5) provide for circulating concentrations of unbound active pharmaceutical ingredient above threshold concentrations for 24 or more hours from a single administered dose, and (6) provide for more consistent drug absorption by treated individuals as compared to existing capsule formulations.

Pharmaceutical co-formulations of the current invention designed to treat a range of conditions in humans and animals include the combination of $K_{ATP}$ channel openers with: (1) a diuretic, (2) a drug that lowers blood pressure, (3) a drug that suppresses appetite, (4) a cannabinoid receptor antagonist, (5) a drug that suppresses that action of gastric lipases, (6) any drug that is used to induce weight loss, (7) a drug that lowers cholesterol, (8) a drug that lowers LDL bound cholesterol, (9) a drug that improves insulin sensitivity, (10) a drug that improves glucose utilization or uptake, (11) a drug that reduces incidence of atherosclerotic plaque, (12) a drug that reduces inflammation, (13) a drug that is antidepressant, (14) a drug that is an anti-epileptic, or (15) a drug that is an anti-psychotic.

Treatment of humans or animals of the current invention using pharmaceutical formulations of $K_{ATP}$ channel openers result in reduced incidence of adverse side effects including but not limited to edema, fluid retention, reduced rates of excretion of sodium, chloride, and uric acid, hyperglycemia, ketoacidosis, nausea, vomiting, dyspepsia, ileus and headaches. These reductions in frequency of adverse side effects are achieved by: (1) initiating dosing of individuals at subtherapeutic doses and in a step wise manner increasing the dose daily until the therapeutic dose is achieved where the number of days over which the step up in dose is effected is 2 to 10, (2) use of the lowest effective dose to achieve the desired therapeutic effect, (3) use of a pharmaceutical formulation that delays release of active until gastric transit is complete, (4) use of a pharmaceutical formulation that delays release of active until gastric transit is complete, (5) use of a pharmaceutical formulation that results in lower circulating peak drug levels as compared to an immediate release oral suspension or capsule formulation for the same administered dose, and (6) optimizing the timing of administration of dose within the day and relative to meals.

Treatment of patients suffering from Prader Willi Syndrome, Froelich's syndrome, Cohen syndrome, Summit Syndrome, Alstrom, Syndrome, Borjesen Syndrome, Bardet-Biedl Syndrome, and hyperlipoproteinemia type I, II, III, and IV with the current invention using pharmaceutical formulations of $K_{ATP}$ channel openers result in some or all of the following therapeutic outcomes: (1) weight loss, (2) reduced rates of weight gain, (3) inhibition of hyperphagia, (4) reduced incidence of impaired glucose tolerance, prediabetes or diabetes, (5) reduced incidence of congestive heart failure, (6) reduced hypertension, and (7) reduced rates of all cause mortality.

Treatment of prediabetic subjects with the current invention using pharmaceutical formulations of $K_{ATP}$ channel openers result in some or all of the following therapeutic outcomes: (1) weight loss, (2) restoration of normal glucose tolerance, (3) delayed rates of progression to diabetes, (4) reduced hypertension, and (5) reduced rates of all cause mortality.

Treatment of diabetic subjects with the current invention using pharmaceutical formulations of $K_{ATP}$ channel openers result in some or all of the following therapeutic outcomes: (1) weight loss, (2) restoration of normal glucose tolerance, (3) delayed rates of progression of diabetes, (4) improvements in glucose tolerance, (5) reduced hypertension, and (6) reduced rates of all cause mortality.

Co-administration of drugs with formulations of $K_{ATP}$ channel openers in the treatment of diseases of overweight, obese or obesity prone human and animal subjects involves the co-administration of a pharmaceutically acceptable formulation of $K_{ATP}$ channel openers with an acceptable formulation of: (1) Sibutramine, (2) orlistat, (3) Rimonabant, (4) a drug that is an appetite suppressant, (5) any drug used to induce weight loss in an obese or overweight individual, (6) a non-thiazide diuretic, (7) a drug that lowers cholesterol, (8) a drug that raises HDL cholesterol, (9) a drug that lowers LDL cholesterol, (10) a drug that lowers blood pressure, (11) a drug that is an anti-depressant, (12) a drug that improves insulin sensitivity, (13) a drug that improves glucose utilization and uptake (14) a drug that is an anti-epileptic, (15) a drug that is an anti-inflammatory, or (16) a drug that lowers circulating triglycerides.

Co-administration of drugs with formulations of $K_{ATP}$ channel openers in the treatment or prevention of weight gain, dyslipidemia, or impaired glucose tolerance in subjects treated with antipsychotics drugs involve the co-administration of a pharmaceutically acceptable formulation of $K_{ATP}$ channel openers with an acceptable formulation of: lithium, carbamazepine, valproic acid and divalproex, and lamotrigine, antidepressants generally classified as monoamine oxidase inhibitors including isocarboxazid, phenelzine sulfate and tranylcypromine sulfate, tricyclic antidepressants including doxepin, clomipramine, amitriptyline, maproiline, desipromine, nortryptyline, desipramine, doxepin, trimipramine, imipramine and protryptyline, tetracyclic antidepressants including mianserin, mirtazapine, maprotiline, oxaprotline, delequamine, levoprotline, triflucarbine, setiptiline, lortalaline, azipramine, aptazapine maleate and pirlindole, and major tranquilizers and atypical antipsychotics including paloproxidol, perphenazine, thioridazine, risperidone, clozapine, olanzapine and chlorpromazine.

In one embodiment, a $K_{ATP}$ channel opener is administered to an overweight or obese individual as an oral suspension, or an immediate release capsule or tablet or a controlled release formulation or a transdermal formulation or an intranasal formulation to reach and maintain the threshold concentration required to measurably reduce fasting insulin levels for a prolonged period. Preferably the $K_{ATP}$ channel opener formulation reduces fasting insulin levels by at least 20%, more preferably by at least 30%, more preferably by at least by 40%, more preferably by at least 50%, more preferably by at least by 60% more preferably by at least by 70%, and more preferably by at least 80%. Fasting insulin levels are commonly measured using the glucose tolerance test (OGTT). After an overnight fast, a patient ingests a known amount of glucose. Initial glucose levels are determined by measuring pre-test glucose levels in blood and urine. Blood insulin levels are measured by a blood is draw every hour after the glucose is consumed for up to three hours. In a fasting glucose assay individuals with plasma glucose values greater than 200 mg/dl at 2 hours post-glucose load indicate an impaired glucose tolerance.

In another embodiment, a $K_{ATP}$ channel opener is administered to an overweight or obese individual as an oral suspension, or an immediate release capsule or tablet or a controlled release formulation or a transdermal formulation or an intranasal formulation to reach and maintain the threshold concentration required to induce weight loss for a prolonged period.

In another embodiment, a $K_{ATP}$ channel opener is administered to an overweight or obese individual as an oral suspension, or an immediate release capsule or tablet or a controlled release formulation or a transdermal formulation or an intranasal formulation to reach and maintain the threshold concentration required to elevate resting energy expenditure for a prolonged period.

In another embodiment, a $K_{ATP}$ channel opener is administered to an overweight or obese individual as an oral suspension, or an immediate release capsule or tablet or a controlled release formulation or a transdermal formulation or an intranasal formulation to reach and maintain the threshold concentration required to elevate fat and fatty acid oxidation for a prolonged period.

In another embodiment, a $K_{ATP}$ channel opener is administered to an obesity prone individual as an oral suspension, or an immediate release capsule or tablet or a controlled release formulation or a transdermal formulation or an intranasal formulation to reach and maintain the threshold concentration required to induce weight loss for a prolonged period.

In another embodiment, a $K_{ATP}$ channel opener is administered to an obesity prone individual as an oral suspension, or an immediate release capsule or tablet or a controlled release formulation or a transdermal formulation or an intranasal formulation to reach and maintain the threshold concentration required to maintain weight for a prolonged period.

In another embodiment, a $K_{ATP}$ channel opener is administered to an overweight or obese individual as an oral suspension, or an immediate release capsule or tablet or a controlled release formulation or a transdermal formulation or an intranasal formulation to reach and maintain a drug concentration above the threshold concentration required to induce weight loss for a prolonged period.

In another embodiment, a $K_{ATP}$ channel opener is administered to an overweight or obese individual as an oral suspension, or an immediate release capsule or tablet or a controlled release formulation or a transdermal formulation or an intranasal formulation for a prolonged period of time to reduce body fat by more than 25%, more preferably by at least 50%, and more preferably by at least 75%.

In another embodiment, a $K_{ATP}$ channel opener is administered to an overweight or obese individual as an oral suspension, or an immediate release capsule or tablet or a controlled release formulation or a transdermal formulation or an intranasal formulation for a prolonged period of time to preferentially reduce visceral fat deposits.

In another embodiment, a $K_{ATP}$ channel opener is administered to an overweight or obese individual as an oral suspension, or an immediate release capsule or tablet or a controlled release formulation or a transdermal formulation or an intranasal formulation for a prolonged period of time to reduce visceral fat depots and other fat deposits.

In another embodiment, a $K_{ATP}$ channel opener is administered to a normoinsulemic overweight or obese individual as an oral suspension, or an immediate release capsule or tablet or a controlled release formulation or a transdermal formulation or an intranasal formulation to reach and maintain a drug concentration above the threshold concentration required to induce weight loss for a prolonged period.

In another embodiment, a $K_{ATP}$ channel opener is administered to a prediabetic individual as an oral suspension, or an immediate release capsule or tablet or a controlled release formulation or a transdermal formulation or an intranasal formulation to reach and maintain a drug concentration above the threshold concentration required to prevent the transition to diabetes for a prolonged period.

In another embodiment, a $K_{ATP}$ channel opener is administered to a type 1 diabetic individual as an oral suspension, or an immediate release capsule or tablet or a controlled release formulation or a transdermal formulation or an intranasal formulation to reach and maintain a drug concentration above the threshold concentration required to induce beta cell rest for a prolonged period.

In another embodiment, a single dose of a pharmaceutically acceptable formulation of a $K_{ATP}$ channel opener is administered to an individual in need thereof that results in circulating concentration of active drug sufficient to diminish the secretion of insulin for 24 or more hours.

In another embodiment, a pharmaceutically acceptable formulation of a $K_{ATP}$ channel opener is administered over a prolonged basis to an individual in need thereof no more than once per 24 hours that results in circulating concentration of active drug sufficient to diminish the secretion of insulin on a continuous basis.

In another embodiment, a single dose of a pharmaceutically acceptable formulation of a $K_{ATP}$ channel opener is administered to an individual in need thereof that results in circulating concentration of active drug sufficient to elevate non-esterified fatty acids in circulation for 24 or more hours.

In another embodiment, a pharmaceutically acceptable formulation of a $K_{ATP}$ channel opener is administered over a prolonged basis to an individual in need thereof no more than once per 24 hours that results in circulating concentration of active drug sufficient to elevate non-esterified fatty acids in circulation on a continuous basis.

In another embodiment, a single dose of a pharmaceutically acceptable formulation of a $K_{ATP}$ channel opener is administered to an individual in need thereof that results in circulating concentration of active drug sufficient to treat hypoglycemia in circulation for 24 or more hours.

In another embodiment, a pharmaceutically acceptable formulation of a $K_{ATP}$ channel opener is administered over a prolonged basis to an individual in need thereof no more than once per 24 hours that results in circulating concentration of active drug sufficient to treat hypoglycemia on a continuous basis.

In another embodiment, a pharmaceutically acceptable formulation of a $K_{ATP}$ channel opener is administered over a prolonged basis to an individual in need thereof no more than once per 24 hours that results in circulating concentration of active drug sufficient to induce weight loss on a continuous basis.

In another embodiment, a pharmaceutically acceptable formulation of a $K_{ATP}$ channel opener is administered over a prolonged basis to an individual in need thereof no more than once per 24 hours that results in circulating concentration of active drug sufficient to maintain weight on a continuous basis, as it is preferable to maintain weight in an obese individual once some weight loss has occurred when the alternative is to regain weight.

In another embodiment, a pharmaceutically acceptable formulation of a $K_{ATP}$ channel opener is administered over a prolonged basis to an individual in need thereof no more than once per 24 hours that results in circulating concentration of active drug sufficient to reduce circulating triglyceride levels on a continuous basis.

In another embodiment, a single dose of a pharmaceutically acceptable formulation of a $K_{ATP}$ channel opener is administered to an individual in need thereof that results in circulating concentration of active drug sufficient to reduce or prevent ischemic or reperfusion injury in circulation for 24 or more hours.

In another embodiment, a pharmaceutically acceptable formulation of a $K_{ATP}$ channel opener is administered over a prolonged basis to an individual in need thereof no more than once per 24 hours that results in circulating concentration of active drug sufficient reduce or prevent ischemic or reperfusion injury on a continuous basis.

In another embodiment, the adverse effects frequency of treatment with a $K_{ATP}$ channel opener is reduced using a pharmaceutically acceptable formulation of diazoxide or its derivatives that is administered to an individual in need thereof on a daily basis in which the first dose is known to be subtherapeutic and daily dose is subsequently increased stepwise until the therapeutic dose is reached.

In another embodiment, the adverse effects frequency of treatment with a $K_{ATP}$ channel opener is reduced using a pharmaceutically acceptable formulation of a $K_{ATP}$ channel opener that is administered to an individual in need thereof on a daily basis in which the active ingredient is not release from the formulation until gastric transit is complete.

In another embodiment, the adverse effects frequency of treatment with a $K_{ATP}$ channel opener is reduced using a pharmaceutically acceptable formulation of a $K_{ATP}$ channel opener that is administered to an individual in need thereof on a daily basis in which the active ingredient is not release from the formulation until gastric transit is complete.

In another embodiment, the adverse effects frequency of treatment with a $K_{ATP}$ channel opener is reduced using a pharmaceutically acceptable formulation of a $K_{ATP}$ channel opener that is administered to an individual in need thereof on a daily basis in which the maximum circulating concentration of active ingredient is lower than what would be realized by the administration of the same dose using an oral suspension or capsule formulation.

In another embodiment, the adverse effects frequency of treatment with a $K_{ATP}$ channel opener is reduced using a pharmaceutically acceptable formulation of a $K_{ATP}$ channel opener that is administered to an individual in need thereof on a daily basis in which the first dose is known to be subtherapeutic and daily dose is subsequently increased stepwise until the therapeutic dose is reached, the active ingredient is not release from the formulation until gastric transit is complete and in which the maximum circulating concentration of active ingredient is lower than what would be realized by the administration of the same dose using an oral suspension or capsule formulation.

In another embodiment, the adverse effects frequency of treatment with a $K_{ATP}$ channel opener is reduced using a pharmaceutically acceptable formulation of a $K_{ATP}$ channel opener that is administered to an overweight or obese individual in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 2.5 mg/kg/day.

In another embodiment, the adverse effects frequency of treatment with a $K_{ATP}$ channel opener is reduced using a pharmaceutically acceptable formulation of a $K_{ATP}$ channel opener that is administered to an overweight or obese individual in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 1.75 mg/kg/day.

In another embodiment, the treatment of an overweight or obese individual is optimized for weight loss by administration of a pharmaceutically acceptable formulation of a $K_{ATP}$ channel opener once per 24 hours in which the release of the active ingredient from the formulation has been modified to provide near zero order release for at least 12 hours.

In another embodiment, the treatment of an overweight or obese individual is optimized for weight loss by administration of a pharmaceutically acceptable formulation of a $K_{ATP}$ channel opener once per 24 hours in which the release of the active ingredient from the formulation has been modified to provide near zero order release for at least 18 hours.

In another embodiment, the treatment of an overweight or obese individual is optimized for weight loss by administration of a pharmaceutically acceptable formulation of a $K_{ATP}$ channel opener once per 24 hours in which the release of the active ingredient from the formulation has been modified to provide a rising drug concentration in circulation for at least 12 hours.

In another embodiment, the treatment of an overweight or obese individual is optimized for weight loss by administration of a pharmaceutically acceptable formulation of a $K_{ATP}$ channel opener once per 24 hours in which the release of the active ingredient from the formulation has been modified to provide a rising drug concentration in circulation for at least 18 hours.

In another embodiment, the treatment of an overweight or obese individual is optimized for weight loss by administration of a pharmaceutically acceptable formulation of a $K_{ATP}$ channel opener once per 24 hours in which the release of the active ingredient from the formulation has been modified to match the pattern of basal insulin secretion.

In another embodiment, the adverse effects frequency of treatment with a $K_{ATP}$ channel opener is reduced using a pharmaceutically acceptable formulation of a $K_{ATP}$ channel opener that is administered to an obesity prone individual in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 2.5 mg/kg/day.

In another embodiment, the adverse effects frequency of treatment with a $K_{ATP}$ channel opener is reduced using a pharmaceutically acceptable formulation of a $K_{ATP}$ channel opener that is administered to an obesity prone individual in need thereof on a daily basis in which the first dose is known to be subtherapeutic and daily dose is subsequently increased stepwise until the therapeutic dose is reached, the active ingredient is not release from the formulation until gastric transit is complete, in which the maximum circulating concentration of active ingredient is lower than what would be realized by the administration of the same dose using an oral suspension or capsule formulation, and in which the maximum dose is less than 1.75 mg/kg/day.

In another embodiment, the treatment of an obesity prone individual is optimized for weight maintenance by administration of a pharmaceutically acceptable formulation of a $K_{ATP}$ channel opener once per 24 hours in which the release of the active ingredient from the formulation has been modified to provide near zero order release for at least 12 hours.

In another embodiment, the treatment of an obesity prone individual is optimized for weight maintenance by administration of a pharmaceutically acceptable formulation of a $K_{ATP}$ channel opener once per 24 hours in which the release of the active ingredient from the formulation has been modified to provide near zero order release for at least 18 hours.

In another embodiment, the treatment of an obesity prone individual is optimized for weight maintenance by administration of a pharmaceutically acceptable formulation of a $K_{ATP}$ channel opener once per 24 hours in which the release of the active ingredient from the formulation has been modified to provide a rising drug concentration in circulation for at least 12 hours.

In another embodiment, the treatment of an obesity prone individual is optimized for weight maintenance by administration of a pharmaceutically acceptable formulation of a $K_{ATP}$ channel opener once per 24 hours in which the release of the active ingredient from the formulation has been modified to provide a rising drug concentration in circulation for at least 18 hours.

In another embodiment, the treatment of an obesity prone individual is optimized for weight maintenance by administration of a pharmaceutically acceptable formulation of a $K_{ATP}$ channel opener once per 24 hours in which the release of the active ingredient from the formulation has been modified to match the pattern of basal insulin secretion.

In another embodiment, a pharmaceutically acceptable formulation of a $K_{ATP}$ channel opener is co-administered with sibutramine to an overweight or obese individual to induce weight loss.

In another embodiment, a pharmaceutically acceptable formulation of a $K_{ATP}$ channel opener is co-administered with orlistat to an overweight or obese individual to induce weight loss.

In another embodiment, a pharmaceutically acceptable formulation of a $K_{ATP}$ channel opener is co-administered with rimonabant to an overweight or obese individual to induce weight loss.

In another embodiment, a pharmaceutically acceptable formulation of a $K_{ATP}$ channel opener is co-administered with an appetite suppressant to an overweight or obese individual to induce weight loss.

In another embodiment, a pharmaceutically acceptable formulation of a $K_{ATP}$ channel opener is co-administered with an anti-depressant to an overweight or obese individual to induce weight loss.

In another embodiment, a pharmaceutically acceptable formulation of a $K_{ATP}$ channel opener is co-administered with anti-epileptic to an overweight or obese individual to induce weight loss.

In another embodiment, a pharmaceutically acceptable formulation of a $K_{ATP}$ channel opener is co-administered with a non-thiazide diuretic to an overweight or obese individual to induce weight loss.

In another embodiment, a pharmaceutically acceptable formulation of a $K_{ATP}$ channel opener is co-administered with a drug that induces weight loss by a mechanism that is distinct from diazoxide to an overweight or obese individual to induce weight loss.

In another embodiment, a pharmaceutically acceptable formulation of a $K_{ATP}$ channel opener is co-administered with a drug that lowers blood pressure to an overweight, obesity prone or obese individual to induce weight loss and treat obesity associated comorbidities.

In another embodiment, a pharmaceutically acceptable formulation of a $K_{ATP}$ channel opener is co-administered with a drug a drug that lowers cholesterol to an overweight, obesity prone or obese individual to induce weight loss and treat obesity associated comorbidities.

In another embodiment, a pharmaceutically acceptable formulation of a $K_{ATP}$ channel opener is co-administered with a drug that raises HDL associated cholesterol to an overweight, obesity prone or obese individual to induce weight loss and treat obesity associated comorbidities.

In another embodiment, a pharmaceutically acceptable formulation of a $K_{ATP}$ channel opener is co-administered with a drug that improves insulin sensitivity to an overweight, obesity prone or obese individual to induce weight loss and treat obesity associated comorbidities.

In another embodiment, a pharmaceutically acceptable formulation of a $K_{ATP}$ channel opener is co-administered with a an anti-inflammatory to an overweight, obesity prone or obese individual to induce weight loss and treat obesity associated comorbidities.

In another embodiment, a pharmaceutically acceptable formulation of a $K_{ATP}$ channel opener is co-administered with a drug that lowers circulating triglycerides to an overweight, obesity prone or obese individual to induce weight loss and treat obesity associated comorbidities.

In another embodiment, $K_{ATP}$ channel openers are co-formulated with sibutramine in a pharmaceutically acceptable formulation that is administered to an overweight, obesity prone or obese individual to induce weight loss and treat obesity-associated co-morbidities.

In another embodiment, $K_{ATP}$ channel openers are co-formulated with orlistat or other active that suppresses the action of gastric lipases in a pharmaceutically acceptable formulation that is administered to an overweight, obesity prone or obese individual to induce weight loss and treat obesity-associated co-morbidities.

In another embodiment, $K_{ATP}$ channel openers are co-formulated with a non-thiazide diuretic in a pharmaceutically acceptable formulation that is administered to an overweight, obesity prone or obese individual to induce weight loss and treat obesity-associated co-morbidities.

In another embodiment, $K_{ATP}$ channel openers are co-formulated with an appetite suppressant in a pharmaceutically acceptable formulation that is administered to an overweight, obesity prone or obese individual to induce weight loss and treat obesity-associated co-morbidities.

In another embodiment, $K_{ATP}$ channel openers are co-formulated with a cannabinoid receptor antagonist in a pharmaceutically acceptable formulation that is administered to an overweight, obesity prone or obese individual to induce weight loss and treat obesity-associated co-morbidities.

In another embodiment, $K_{ATP}$ channel openers are co-formulated with an anti-cholesteremic active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an antihypertensive active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an insulin sensitizing active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an anti-inflammatory active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an anti-depressant active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an anti-epileptic active in a pharmaceutically acceptable formulation that is administered to an overweight, obesity prone or obese individual to induce weight loss and treat obesity-associated co-morbidities.

In another embodiment, $K_{ATP}$ channel openers are co-formulated with an active that reduces the incidence of atherosclerotic plaque in a pharmaceutically acceptable formulation that is administered to an overweight, obesity prone or obese individual to induce weight loss and treat obesity-associated co-morbidities.

In another embodiment, $K_{ATP}$ channel openers are co-formulated with an active that lowers circulating concentrations of triglycerides in a pharmaceutically acceptable formulation that is administered to an overweight, obesity prone or obese individual to induce weight loss and treat obesity-associated co-morbidities.

The reduction of circulating triglycerides in an overweight, obese or obesity prone individual is achieved by the administration of an effective amount of a solid oral dosage form of a $K_{ATP}$ channel opener.

A solid oral dosage form of $K_{ATP}$ channel opener can be used to administer a therapeutically effective dose of $K_{ATP}$ channel opener to an overweight or obesity prone individual in need thereof to maintain weight, as it is preferable to maintain weight in an obese individual once some weight loss has occurred when the alternative is to regain weight.

A method of inducing loss of greater than 25% of initial body fat in an overweight or obese individual can be achieved by the prolonged administration of a solid oral dosage form of a $K_{ATP}$ channel opener.

A method of inducing loss of greater than 50% of initial body fat in an overweight or obese individual can be achieved by the prolonged administration of a solid oral dosage form of a $K_{ATP}$ channel opener A method of inducing loss of greater than 75% of initial body fat in an overweight or obese individual can be achieved by the prolonged administration of a solid oral dosage form of a $K_{ATP}$ channel opener.

A method of inducing preferential loss of visceral fat in an overweight or obese individual can be achieved by the prolonged administration of a solid oral dosage form of a $K_{ATP}$ channel opener.

A method of inducing loss of body fat and reductions in circulating triglycerides in an overweight or obese individual can be achieved by the prolonged administration of a solid oral dosage form of a $K_{ATP}$ channel opener.

The invention will now be described with reference to the following non-limiting examples.

EXAMPLES

A. Potassium ATP Channel Activator Containing Formulations

1. Compressed Tablet Formulations

Diazoxide or a derivative thereof at about 15-30% by weight is mixed with hydroxypropyl methylcellulose at about 55-80% by weight, ethylcellulose at about 3-10 wt/vol % and magnesium stearate (as lubricant) and talc (as glidant) each at less than 3% by weight. The mixture is used to produce a compressed tablet as described in Reddy et al., *AAPS Pharm Sci Tech* 4(4):1-9 (2003). The tablet may be coated with a thin film as discussed below for microparticles.

A tablet containing 100 mg of diazoxide or a derivative thereof will also contain approximately 400 mg of hydroxypropyl cellulose and 10 mg of ethylcellulose. A tablet containing 50 mg of diazoxide or a derivative thereof will also contain approximately 200 mg of hydroxypropyl cellulose and 5 mg of ethylcellulose. A tablet containing 25 mg of diazoxide or a derivative thereof will also contain approximately 100 mg of hydroxypropyl cellulose and 2.5 mg of ethylcellulose.

2. Encapsulated Coated Microparticle Formulation of Diazoxide

Diazoxide or a derivative thereof is encapsulated into microparticles in accordance with well known methods (see, e.g. U.S. Pat. No. 6,022,562). Microparticles of between 100 and 500 microns in diameter containing diazoxide or derivative, alone or in combination with one or more suitable excipient, is formed with the assistance of a granulator and then sieved to separate microparticles having the appropriate size. Micriparticles are coated with a thin film by spray drying using commercial instrumentation (e.g. Uniglatt Spray Coating Machine). The thin film comprises ethylcellulose, cellulose acetate, polyvinylpyrrolidone and/or polyacrylamide. The coating solution for the thin film may include a plasticizer which may be castor oil, diethyl phthalate, triethyl citrate and salicylic acid. The coating solution may also include a lubricating agent which may be magnesium stearate, sodium oleate, or polyoxyethylenated sorbitan laurate. The coating solution may further include an excipient such as talc, colloidal silica or of a mixture of the two added at 1.5 to 3% by weight to prevent caking of the film coated particles.

3. Formulation of a Tableted Form of Diazoxide or a Derivative for Controlled Release Prior to mixing, both the active ingredient and hydroxypropyl methylcellulose (Dow Methocel K4M P) are passed through an ASTM 80 mesh sieve. A mixture is formed from 1 part diazoxide or a derivative thereof to 4 parts hydroxypropyl methylcellulose. After thorough mixing, a sufficient volume of an ethanolic solution of ethylcellulose as a granulating agent is added slowly. The quantity of ethylcellulose per tablet in the final formulation is about ⅒th part. The mass resulting from mixing the granulating agent is sieved through 22/44 mesh. Resulting granules are dried at 40° C. for 12 hours and thereafter kept in a desiccator for 12 hours at room temperature. Once dry the granules retained on 44 mesh are mixed with 15% fines (granules that passed through 44 mesh). Talc and magnesium stearate are added as glidant and lubricant at 2% of weight each. A colorant is also added. The tablets are compressed using a single punch tablet compression machine.

4. Formulation of a Compression Tableted Form of Diazoxide or a Derivative Thereof that Provides for Controlled Release.

Diazoxide or a derivative thereof at 20-40% weight is mixed with 30% weight hydroxypropyl methylcellulose (Dow Methocel K100LV P) and 20-40% weight impalpable lactose. The mixture is granulated with the addition of water. The granulated mixture is wet milled and then dried 12 hours at 110° C. The dried mixture is dry milled. Following milling, 25% weight ethylcellulose resin is added (Dow Ethocel 10FP or Ethocel 100FP) followed by 0.5% weight magnesium stearate. A colorant is also added. The tablets are compressed using a single punch tablet compression machine (Dasbach, et al, Poster at AAPS Annual Meeting Nov. 10-14 (2002)).

5. Formulation of a Compression Coated Tableted Form of Diazoxide or a Derivative Thereof That Provides for Controlled Release.

The core tablet is formulated by mixing either 100 mg of diazoxide or a derivative thereof with 10 mg of ethylcellulose (Dow Ethocel 10FP), or by mixing 75 mg of diazoxide or a derivative thereof with 25 mg lactose and 10 mg of ethylcellulose (Dow Ethocel 10FP), or by mixing 50 mg of diazoxide or a derivative thereof with 50 mg of lactose and 10 mg of ethylcellulose (Dow Ethocel 10FP). The core tablets are formed on an automated press with concave tooling. The compression coating consisting of 400 mg of ethylene oxide (Union Carbide POLYOX WSR Coagulant) is applied and compressed to 3000 psi (Dasbach, et al., Poster at AAPS Annual Meeting Oct. 26-30 (2003)).

6. A Controlled Release Dosage Form of Diazoxide or a Derivative Thereof Using an Osmotically Controlled Release System.

Diazoxide or a derivative thereof is formulated as an osmotically regulated release system. In general, two components, and expandable hydrogel that drives release of the active drug is assembled with diazoxide or a derivative thereof into a semipermeable bilaminate shell. Upon assembly a hole is drilled in the shell to facilitate release of active upon hydration of the hydrogel.

A dosage form adapted, designed and shaped as an osmotic delivery system is manufactured as follows: first, a diazoxide or a derivative thereof composition is provided by blending together into a homogeneous blend of polyethylene oxide, of diazoxide or a derivative thereof and hydroxypropyl methylcellulose. Then, a volume of denatured anhydrous ethanol weighing 70% of the dry mass is added slowly with continuous mixing over 5 minutes. The freshly prepared wet granulation is screened through a 20 mesh screen through a 20 mesh screen, dried at room temperature for 16 hours, and again screened through a 20 mesh screen. Finally, the screened granulation is mixed with 0.5% weight of magnesium stearate for 5 minutes.

A hydrogel composition is prepared as follows: first, 69% weight of polyethylene oxide weight, 25% weight of sodium chloride and 1% weight ferric oxide separately are screened through a 40 mesh screen. Then, all the screened ingredients are mixed with 5% weight of hydroxypropyl methylcellulose to produce a homogeneous blend. Next, a volume of denatured anhydrous alcohol equal to 50% of the dry mass is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 0.5% weight of magnesium stearate 5 minutes (see U.S. Pat. No. 6,361,795 by Kuczynski, et al.).

The diazoxide or a derivative thereof composition and the hydrogel composition are compressed into bilaminate tablets. First the diazoxide or a derivative thereof composition is added and tamped, then, the hydrogel composition is added and the laminae are pressed under a pressure head of 2 tons into a contacting laminated arrangement.

The bilaminate arrangements are coated with a semipermeable wall (i.e. thin film). The wall forming composition comprises 93% cellulose acetate having a 39.8% acetyl content, and 7% polyethylene glycol. The wall forming composition is sprayed onto and around the bilaminate.

Finally an exit passageway is drilled through the semipermeable wall to connect the diazoxide or a derivative thereof drug lamina with the exterior of the dosage system. The residual solvent is removed by drying at 50° C. and 50% humidity. Next, the osmotic systems are dried at 50° C. to remove excess moisture (see U.S. Pat. No. 6,361,795 by Kuczynski, et al.).

7. Preparation of a Salt of Diazoxide.

A hydrochloride salt of diazoxide is prepared by dissolving one mole of diazoxide (230.7 g) in 500 ml of Et2O. Dry HCl is passed into the solution until the weight of the container is increased by 36 g. During the addition of the HCl, the HCl salt of diazoxide precipitates as a powder. The salt is filtered off and washed with dry Et20.

B. In Vivo Obesity Testing

1. Obesity Animal Model

Formulations of diazoxide or derivatives prepared as described herein can be tested for efficacy in an animal model of obesity as described by Surwit et al. (*Endocrinology* 141:3630-3637 (2000)). Briefly, 4-week-old B6 male mice are housed 5/cage in a temperature-controlled (22° C.) room with a 12-h light, 12-h dark cycle. The high fat (HF) and low fat (LF) experimental diets contain 58% and 11% of calories from fat, respectively. A group of mice are fed the HF diet for the first 4 weeks of the study; the remaining 15 mice are fed the LF diet. The mice assigned to the LF diet are maintained on this diet throughout the study as a reference group of lean control mice. At week 4, all HF-fed mice a reassigned to 2 groups of mice. The first group remains on the HF diet throughout the study as the obese control group. The remaining 3 groups of mice are fed the HF diet and administered the controlled release formulation of diazoxide or derivative at about 150 mg of active per kg per day as a single dose administered by oral gavage. Animals are weighed weekly, and food consumption is measured per cage weekly until the diets are changed at week 4, whereupon body weight and food intake are determined daily. The feed efficiency (grams of body weight gained per Cal consumed) is calculated on a per cage basis. Samples for analysis of insulin, glucose, and leptin are collected on day 24 (4 days before the diets are changed), on day 32 (4 days after the change), and biweekly thereafter. In all cases food is removed 8 h before samples are collected. Glucose is analyzed by the glucose oxidase method. Insulin and leptin concentrations are determined by double antibody RIA. The insulin assay is based on a rat standard, and the leptin assay uses a mouse standard. At the termination of the study, a postprandial plasma sample is collected and analyzed for triglyceride and nonesterified fatty acid concentrations. After 4 weeks of drug treatment, a subset of 10 animals from each group is killed. The epididymal white adipose tissue (EWAT), retroperitoneal (RP) fat, interscapular brown adipose tissue (IBAT) fat pads, and gastrocnemius muscle are removed, trimmed, and weighed. The percent body fat is estimated from the weight of the epididymal fat pad. A subset of five animals from each group is injected ip with 0.5 g/kg glucose. At 30 min postinjection, a plasma sample is collected and analyzed for glucose content by the glucose oxidase method.

2. Treatment of Obesity in Humans

Formulations of diazoxide or derivatives prepared as described herein can be tested for efficacy in obese humans. The study is conducted as described by Alemzadeh (Alemzadeh, et al., *J Clin Endocr Metab* 83:1911-1915 (1998)). Subjects consist of moderate-to-morbidly obese adults with a body mass index (BMI) greater than or equal to 30 kg/m2. Each subject undergoes a complete physical examination at the initial evaluation, body weight being measured on a standard electronic scale and body composition by DEXA.

Before the initiation of the study, all subjects are placed on a hypocaloric diet for a lead-in period of 1 week. This is designed to exclude individuals who are unlikely to be compliant and to ensure stable body weight before treatment. Up to 50 patients are tested at each dosage of drug. Daily dosage is set at 100, 200, and 300 mg/day. The daily dose is divided into 2 doses for administration. The dose is administered as either one, two or three 50 mg capsules or tablets at each time of administration. Individual patients are dosed daily for up to 12 months. Patients are reviewed weekly, weighed, and asked about any side effects or concurrent illnesses.

Twenty-four-hour dietary recall is obtained from each patient. The dietary recalls are analyzed using a standard computer software program. All patients are placed on a hypocaloric diet and encouraged to participate in regular exercise.

Before commencing, and after completion of the study, the following laboratory tests are obtained: blood pressure fasting plasma glucose, insulin, cholesterol, triglycerides, free fatty acids (FFA), and glycohemoglobin and measures of rate of appearance and oxidation of plasma derived fatty acids. Additionally, routine chemistry profiles and fasting plasma glucose are obtained weekly to identify those subjects with evidence of glucose intolerance and/or electrolyte abnormalities. Glucose is analyzed in plasma, by the glucose oxidase method.

Insulin concentration is determined by RIA using a double-antibody kit. Cholesterol and triglycerides concentrations are measured by an enzymatic method. Plama FFA is determined by an enzymatic colorimetric method. SI was assessed by an iv glucose tolerance test (IVGTT) using the modified minimal model. After an overnight fast, a glucose bolus (300 mg/kg) was administered iv, followed (20 min later) by a bolus of insulin. Blood for determination of glucose and insulin is obtained from a contra lateral vein at −30, −15, 0, 2, 3, 4, 5, 6, 8, 10, 19, 22, 25, 30, 40, 50, 70, 100, 140, and 180 min. SI and glucose effectiveness (SG) are calculated using Bergman's modified minimal-model computer program before and after the completion of the study. Acute insulin response to glucose is determined over the first 19 min of the IVGTT, and the glucose disappearance rate (Kg) is determined from 8-19 min of the IVGTT. Body composition is measured by bioelectrical impedance before and at the completion of the study. Resting energy expenditure (REE) is measured by indirect calorimetry after an overnight 12-h fast, with subjects lying supine for a period of 30 min. Urine is collected over the corresponding 24 h, for measurement of total nitrogen and determination of substrate use, before and after the study.

3. Treatment of Obesity in Humans by Co-administering Diazoxide and Phentermine

Evaluation of a prolonged co-administration of solid oral dosage form of diazoxide or a derivative thereof and phentermine in obese humans with a moderate-to-morbidly and a body mass index (BMI) greater than or equal to 30 kg/m2. Each subject undergoes a complete physical examination at the initial evaluation, body weight being measured on a standard electronic scale and body composition by DEXA.

Before the initiation of the study, all subjects are placed on a hypocaloric diet for a lead-in period of 1 week. This is designed to exclude individuals who are unlikely to be compliant and to ensure stable body weight before treatment. Up to 100 patients are tested. Daily dosage of diazoxide is set at 200 mg. The daily dose is divided into 2 doses for administration. The dose is administered as either a 100 mg capsule or a 100 mg tablet at each time of administration. Individual patients are dosed daily for up to 12 months. Phentermine is administered as a single daily dose of 15 mg. Patients are reviewed every two weeks, weighed, and asked about any side effects or concurrent illnesses.

All patients are continued on a hypocaloric diet and encouraged to participate in regular exercise. Before commencing, and after completion of the study, laboratory tests as described in the example above are obtained.

4. Prevention of Diabetes in Prediabetic Humans

The example describes use of diazoxide in a prediabetic individual to prevent the occurrence of diabetes. Individuals included in the study all have elevated risk of developing diabetes as measured by one of two methods. In a fasting glucose assay they have plasma glucose values between 100 and 125 mg/dl indicating impaired fasting glucose, or in an oral glucose tolerance test they have plasma glucose values between 140 and 199 mg/dl at 2 hours post-glucose load indicating they have impaired glucose tolerance. Treatment is initiated in any individual meeting either criteria. Treated individuals receive either 200 mg diazoxide per day as a 100 mg capsule or tablet twice per day or as two 100 mg capsules or tablets once per day. Placebo treated individuals receive either one placebo capsule or tablet twice per day or two placebo capsules or tablets once per day.

Treatment is continued for once year with OGTT or fasting glucose measured monthly.

5. A Sustained Release Coformulation of Diazoxide HCl and Metformin HCl Use to Treat Diabetic Patients A sustained release co-formulation of diazoxide HCl and metformin HCl is produced by forming a compressed tablet matrix that includes 750 mg of metformin HCl and 100 mg of diazoxide HCl. These active ingredients are blended with sodium carboxymethyl cellulose (about 5% (w/w)), hypromellose (about 25% (w/w), and magnesium stearate (<2% (w/w)). The compressed tablet is further coated with a combination of ethylcellulose (80% (w/w)) and methyl cellulose (20% (w/w)) as a thin film to control rate of hydration and drug release.

Type II diabetic patients are treated with the oral dosage form by administration of two tablets once per day or one tablet every 12 hours. Treatment of the patient with the drug is continued until one of two therapeutic endpoints is reached, or for so long as the patient derives therapeutic benefit from administration. The two therapeutic endpoints that would serve as the basis for the decision to cease treatment include the patient reaching a Body Mass Index (BMI (kg/m$^2$)) between 18 and 25 or the re-establishment of normal glucose tolerance in the absence of treatment. The patient is monitored periodically for (a) glucose tolerance using an oral glucose tolerance test, (b) glycemic control using a standard blood glucose assay, (c) weight gain or loss, (d) progression of diabetic complications, and (e) adverse effects associated with the use of these active ingredients.

6. Prevention or Treatment of Weight Gain in a Patient Treated with Olanzapine

Pharmacotherapy for schizophrenia is initiated for a patient meeting DSM III-R criteria for schizophrenia. The patient is administered 10 mg of olanzapine (Zyprexa, Lilly) once per day. Adjunctive therapy to the patient for schizophrenia includes 250 mg equivalent of valproic acid as divalproex sodium (Depakote, Abbott Labs). Weight gain, dyslipidemia and impaired glucose tolerance, and metabolic syndrome are high frequency adverse events in patients treated with this combination of anti-psychotics. Weight gain, dyslipidemia, impaired glucose tolerance or metabolic syndrome are treated by the co-administration of a therapeutically effective dose of a $K_{ATP}$ channel opener. The patient is treated with administration of 200 mg/day of diazoxide as a once daily tablet formulation. Diazoxide administration continues until the weight gain, dyslipidemia, impaired glucose tolerance or metabolic syndrome is corrected or until treatment of the patient with olanzapine is discontinued. Dyslipidemia is detected by measuring circulating concentrations of total, HDL, and LDL cholesterol, triglycerides and non-esterified fatty acids. Impaired glucose tolerance is detected through the use of oral or IV glucose tolerance tests. Metabolic syndrome is detected by measuring its key risk factors including central obesity, dyslipidemia, impaired glucose tolerance, and circulating concentrations of key proinflammatory cytokines.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope. Changes therein and other uses will occur to those skilled in the art, which are encompassed within the spirit of the invention, are defined by the scope of the claims.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method of treating hyperphagia associated with Prader Willi Syndrome, said method comprising administering a pharmaceutical formulation of diazoxide to a subject in need thereof.

2. The method of claim 1, wherein the pharmaceutical formulation is orally administered.

3. The method of claim 2, wherein the pharmaceutical formulation includes at least one excipient which affects the rate of release of diazoxide.

4. The method of claim 2, wherein the pharmaceutical formulation includes at least one excipient that delays release of diazoxide.

5. The method of claim 1, wherein the pharmaceutical formulation includes at least one other active ingredient.

6. The method of claim 2, wherein the pharmaceutical formulation includes at least one other active ingredient.

7. The method of claim 3, wherein the pharmaceutical formulation includes at least one other active ingredient.

8. The method of claim 4, wherein the pharmaceutical formulation includes at least one other active ingredient.

9. The method of claim 2, wherein the pharmaceutical formulation is administered twice per day.

10. The method of claim 2, wherein the pharmaceutical formulation is administered once per day.

* * * * *